US011667784B2

United States Patent
Reineke et al.

(10) Patent No.: US 11,667,784 B2
(45) Date of Patent: Jun. 6, 2023

(54) COPOLYMERS INCLUDING CINCHONA ALKALOID COMPONENTS AND ONE OR MORE ACRYLAMIDE OR ACRYLATE CONTAINING COMPONENTS, COMPLEXES CONTAINING THE SAME, AND METHODS OF USING THE

(71) Applicant: REGENTS OF THE UNIVERSITY OF MINNESOTA, Minneapolis, MN (US)

(72) Inventors: Theresa Reineke, Vadnais Heights, MN (US); Craig Van Bruggen, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 1071 days.

(21) Appl. No.: 16/043,992

(22) Filed: Jul. 24, 2018

(65) Prior Publication Data
US 2019/0153212 A1 May 23, 2019

Related U.S. Application Data

(60) Provisional application No. 62/536,427, filed on Jul. 24, 2017.

(51) Int. Cl.
*C08L 39/00* (2006.01)
*A61K 47/50* (2017.01)
(Continued)

(52) U.S. Cl.
CPC .............. *C08L 39/00* (2013.01); *A61K 31/49* (2013.01); *A61K 47/32* (2013.01); *A61K 47/50* (2017.08);
(Continued)

(58) Field of Classification Search
CPC .......... C08L 39/00; C08L 33/14; C08L 33/24; C08L 2203/02; A61K 47/50; A61K 47/58;
(Continued)

(56) References Cited

U.S. PATENT DOCUMENTS

2013/0043194 A1* 2/2013 McNeel ................. G01N 33/18
210/745
2018/0066091 A1 3/2018 Tale

FOREIGN PATENT DOCUMENTS

CN 103275267 A * 9/2013
WO WO 2016-140845 A1 9/2016

OTHER PUBLICATIONS

CN 103275267 A—machine translation (Year: 2013).*
(Continued)

*Primary Examiner* — Ling Siu Choi
*Assistant Examiner* — Ronald Grinsted
(74) *Attorney, Agent, or Firm* — Mueting Raasch Group

(57) ABSTRACT

Copolymers polymerized from at least one or more cinchona alkaloid containing compounds; and an acrylamide containing monomer, an acrylate containing monomer, or combinations thereof. Method of forming a copolymer-genetic component complex that includes a genetic component and a copolymer where the copolymer includes one or more cinchona alkaloid containing compounds and an acrylamide containing monomer, an acrylate containing monomer, or combinations thereof. Methods of delivering a genetic component to a cell.

14 Claims, 48 Drawing Sheets

(51) Int. Cl.
| | |
|---|---|
| A61K 47/58 | (2017.01) |
| A61K 31/49 | (2006.01) |
| A61K 48/00 | (2006.01) |
| C08F 220/56 | (2006.01) |
| C08L 33/14 | (2006.01) |
| C08L 33/24 | (2006.01) |
| A61K 47/32 | (2006.01) |
| A61K 38/02 | (2006.01) |
| C12N 15/87 | (2006.01) |

(52) U.S. Cl.
CPC .......... *A61K 47/58* (2017.08); *A61K 48/0041* (2013.01); *C08F 220/56* (2013.01); *C08L 33/14* (2013.01); *C08L 33/24* (2013.01); *A61K 38/02* (2013.01); *C08L 2203/02* (2013.01); *C12N 15/87* (2013.01)

(58) Field of Classification Search
CPC .... A61K 31/49; A61K 47/32; A61K 48/0041; A61K 38/02; C08F 220/56; C12N 15/87
USPC ........................................................ 525/204
See application file for complete search history.

(56) References Cited

OTHER PUBLICATIONS

Adair, "Extended survival of glioblastoma patients after chemoprotective HSC gene therapy" 2012 *Science Translational Medicine*, 4(133):133ra57.
Adair, "Gene therapy enhances chemotherapy tolerance and efficacy in glioblastoma patients" 2014 *Journal of Clinical Investigation*, 124(9):4082-92.
Adair, "Lessons learned from two decades of clinical trial experience in gene therapy for Fanconi anemia" 2016 *Curr Gene Ther.*, Epub Jan. 21, 2017.
Adair, "Semiautomated closed system manufacturing of lentivirus gene-modified haematopoietic stem cells for gene therapy" 2016 *Nat Commun.*, 7:13173. Epub Oct. 21, 2016.
Addelhady, "Direct real-time molecular scale visualisation of the degradation of condensed DNA complexes exposed to DNase 1" 20003 *Nucleic Acids Res.*, 31(14):4001-4005.
Agrawal, "Efficient, and Gentle Transfection of Human Adherent Cells in Suspension" 2016 *ACS Applied Materials & Interfaces*, 8(14):8870-4.
Akita, "Quantitative three-dimensional analysis of the intracellular trafficking of plasmid DNA transfected by a nonviral gene delivery system using confocal laser scanning microscopy" 2004 *Mol. Ther.*, 9(3):443-451.
Albuzat, "Transfection of luciferase DNA into various cells by cationic cyclodextrin polyrotaxanes derived from ionene-11" 2012 *J. Mater. Chem.*, 22:8558.
Alvarez, "New polymer-supported catalysts derived from Cinchona alkaloids: Their use in the asymmetric Michael reaction" 1999 *Tetrahedron Lett.*, 40(39):7091-7094.
Andrews, "Differential engraftment of genetically modified CD34+ and CD34—hematopoietic cell subsets in lethally irradiated baboons" May 2000 *Exp. Hemat.*, 28(5):508-518.
Aravindan, "Effect of acyl chain length on transfection efficiency and toxicity of polyethylenimine" 2009 *Int. J. Pharm.*, 378(1-2):201-210.
Beard, "Efficient and stable MGMT—mediated selection of long-term repopulating stem cells in nonhuman primates" Jul. 2010 *The Journal of clinical investigation*, 120(7):2345-54.
Beard, "High-throughput genomic mapping of vector integration sites in gene therapy studies" in: Bunting, ed. *Hematopoietic Stem Cell Protocols, Methods in Molecular Biology*. New York: Springer; 2014. Cover page, title page, and pp. 321-344.
Benjaminsen, "The Possible 'Proton Sponge' Effect of Polyethylenimine (PEI) Does Not Include Change in Lysosomal pH" 2012 *Mol. Ther.*, 21(1):149-157.
Bestor, "Gene silencing as a threat to the success of gene therapy (Review)" 2000 *Journal of Clinical Investigation*, 105(4):409-11.
Biasco, "In vivo tracking of human hematopoiesis reveals patterns of clonal dynamics during early and steady-state reconstitution phases" 2016 *Cell Stem Cell*, 19(1):107-19.
Borchan, "Copolymerization of N-vinylpyrrolidone with quinine" 1987 *Polymer Science U.S.S.R.*, 29(1):43-49.
Borriello, "Polymerization of 3-methyl-1-butene promoted by metallocene catalysts" 1996 *Macromol Rapid Commun.*, 17(8):589-597.
Boussif, "A versatile vector for gene and oligonucleotide transfer into cells in culture and in vivo: polyethylenimine" 1995 Proc. Natl. Acad. Sci. U. S. A., 92(16)7297-7301.
Boyle, "Heparin Enhances Transfection in Concert with a Trehalose-Based Polycation with Challenging Cell Types" 2016 *Biomacromolecules*, 18(1):56-67.
Bryson, "Polymer beacons for Luminescence and Magnetic Resonance Imaging of DNA Delivery" Oct. 2009 *Proceedings of the National Academy of Sciences*, 106(40):16913-8.
Burtner, "Intravenous injection of a foamy virus vector to correct canine SCID-XI" 2014 *Blood*, 123(23):3578-84.
Burton, "Gene therapy progress and prospects: Parkinson's disease" 2003 *Gene Ther.*, 10(20):1721-1727.
Bystrykh, "Counting stem cells: methodological constraints" 2012 *Nat Methods*, 9(6):567-74.
Cannon, "HIV eradication—from Berlin to Boston" Apr. 2014 *Nat Biotechnol.*, 32(4):315-6.
Canver, "BCL11A enhancer dissection by Cas9-mediated in situ saturating mutagenesis" 2015 *Nature*, 527(7577):192-7.
Cavazzana-Calvo, "Transfusion independence and HMGA2 activation after gene therapy of human-thalassaemia" 2010 *Nature*, 467(7313):318-22.
Charest, "Molecular cloning of complementary deoxyribonucleic acid for an androgen-regulated epididymal protein: sequence homology with metalloproteins" 1988 *Molecular endocrinology* (Baltimore, Md) (10):999-1004.
Chen, "Restoration of type VII collagen expression and function in dystrophic epidermolysis bullosa" 2002 *Nat. Genet.*, 32(4):670-675.
Chen, "Some characteristics of the fluorescence of quinine" 1967 *Anal. Biochem.*, 19(2):374-387.
Chiefari, "Living Free-Radical Polymerization by Reversible Addition—Fragmentation Chain Transfer: The RAFT Process" 1998 *Macromol.*, 9297(98):5559-5562.
Chirila, "J. sponges as implant materials: in vivo and in vitro evaluation of cellular invasion" 1993 *Biomaterials*, 14(1):26-38.
Chollet, "Side-effects of a systemic injection of linear polyethylenimine-DNA complexes" 2002 *J. Gene Med.*, 4 (1):84-91.
Cicalese, "Update on the safety and efficacy of retroviral gene therapy for immunodeficiency due to adenosine deaminase deficiency" 2016 *Blood*. 128(1):45-54.
Coelho, "Safety and efficacy of RNAi therapy for transthyretin amyloidosis" 2013 *The New England journal of medicine*, 369(9):819-29.
Cornu, "Refining strategies to translate genome editing to the clinic" 2017 *Nat Med.*, 23(4):415-23. Epub Apr. 8, 2017.
Crowley, "Evolving nanoparticle gene delivery vectors for the liver: What has been learned in 30 years" 2015 *Journal of controlled release: official journal of the Controlled Release Society*, 219:457-70.
Davis, "Evidence of RNAi in humans from systemically administered siRNA via targeted nanoparticles" 2010 *Nature*, 464(7291):1067-70.
De Ravin, "CRISPR-Cas9 gene repair of hematopoietic stem cells from patients with X-linked chronic granulomatous disease" 2017 *Sci Transl Med.*, 9(372).
Dever, "CRISPR/Cas9 beta-globin gene targeting in human haematopoietic stem cells" 2016 *Nature*, 539(7629):384-9.
Dewick, *Essentials of Organic Chemistry: for Students of Pharmacy, Medicinal Chemistry and Biological Chemistry*; John Wiley & Sons, 2013. Cover page, publisher page, table of contents.

(56) References Cited

OTHER PUBLICATIONS

Dewitt, "Selection-free genome editing of the sickle mutation in human adult hematopoietic stem/progenitor cells" 2016 *Sci Transl Med.*, 8(360):360ra134.
Dhande, "N-Acetylgalactosamine Block-co-Polycations Form Stable Polyplexes with Plasmids and Promote Liver-Targeted Delivery" 2016 *Biomacromolecules*, 17(3):830-40.
Dotson, *Polymerization Process Modeling*. John Wiley & Sons, Inc., 1995. Cover page, title page and table of contents.
Edward, "Organocatalytic synthesis of quinine-functionalized poly(carbonate)s" 2012 *Biomacromolecules*, 13(8):2483-2489.
Ellis, "Silencing and variegation of gammaretrovirus and lentivirus vectors" 2005 *Human Gene Therapy*, 16(11):1241-6.
Fan, "Polymer micelle with pH-triggered hydrophobic-hydrophilic transition and de-cross-linking process in the core and its application for targeted anticancer drug delivery" 2012 *Biomacromolecules*, 13(12):4126-4137.
Fares, "Pyrimidoindole derivatives are agonists of human hematopoietic stem cell self-renewal" Sep. 2014 *Science*, 345(6203): 1509-1512.
Ferrari, "Barriers to and new approaches for gene therapy and gene delivery in cystic fibrosis" 2002 *Adv. Drug Deliv. Rev.*, 54(11):1373-1393.
Fichter, "Polymeric Nucleic Acid Vehicles Exploit Active Inter-Organelle Trafficking Mechanisms" Jan. 2013 *ACS Nano.*, 7(1): 347-364.
Findeis, *Nonviral Vectors for Gene Therapy: Methods and Protocols*. Humana Press: Totowa, New Jersey, 2001. Cover page, title page and table of contents.
Fitzgerald, "Effect of an RNA interference drug on the synthesis of proprotein convertase subtilisin/kexin type 9 (PCSK) and the concentration of serum LDL cholesterol in healthy volunteers: a randomised, single-blind, placebo-controlled, phase 1 trial" 2014 *Lancet*, 383(9911):60-8.
Formby, "Poly(Ethylene Oxide)-Modified Poly(β-Amino Ester) Nanoparticles as a pH-Sensitive System for Tumor-Targeted Delivery of Hydrophobic Drugs: Part I" 2011 *In Vitro Evaluations*, 72(2):181-204.
Fraser, "Synthesis of Glycopolymers of Controlled Molecular Weight by Ring-Opening Metathesis Polymerization Using Well-Defined Functional Group Tolerant Ruthenium Carbene Catalystst" 1995 *Macromolecules*, 28:7248-7255.
Gaj, "ZFN, TALEN, and CRISPR/Cas-based methods for genome engineering" 2013 *Trends Biotechnol.*, 31 (7):397-405.
Ganjalikhani, "Delivery Improvement by Co-formulation of Different Modified Polymers in Erythroleukemic Cell Line K562" 2013 *Iranian journal of basic medical sciences*, 16(9):973-8.
Genovese, "Targeted genome editing in human repopulating haematopoietic stem cells" 2014 *Nature*, 510(7504):235-40. PubMed PMID:24870228.
Gonçalves, "Macropinocytosis of polyplexes and recycling of plasmid via the clathrin-dependent pathway impair the transfection efficiency of human hepatocarcinoma cells" 2004 *Mol. Ther.*, 10 (2):373-385.
Gori, "Efficient generation, purification, and expansion of CD34(+) hematopoietic progenitor cells from nonhuman primate-induced pluripotent stem cells" Aug. 2012 *Blood*, 120(13):e35-44.
Gori, "Endothelial Cells Promote Expansion of Long-Term Engrafting Marrow Hematopoietic Stem and Progenitor Cells in Primates" Mar. 2017 *Stem Cells Transl Med.*, 6(3):864-876.
Gori, "Vascular niche promotes hematopoietic multipotent progenitor formation from pluripotent stem cells" 2015 *Journal of Clinical Investigation*, 125(3):1243-1254.
Grandinetti, "Exploring the mechanism of plasmid DNA nuclear internalization with polymer-based vehicles" 2012 *Mol. Pharm.*, 9 (8):2256-2267.
Grandinetti, "Membrane and Nuclear Permeabilization by Polymeric pDNA Vehicles: Efficient Method for Gene Delivery or Mechanism of Cytotoxicity?" Mar 2012 *Mol Pharm.*, 9(3): 523-538.

Guan, "Surface photo-grafting of polyurethane with 2- hydroxyethyl acrylate for promotion of human endothelial cell adhesion and growth" 2000 *J Biomater Sci Polym Ed.*, 11(5):523-36.
Hacein-Bey-Abina, "A modified gamma-retrovirus vector for Xlinked severe combined immunodeficiency" 2014 *New England Journal of Medicine*, 371(15):1407-17.
Hacein-Bey-Abina, "A serious adverse event after successful gene therapy for X-linked severe combined immunodeficiency" 2003 *New England Journal of Medicine*, 348(3):255-6.
Hacein-Bey-Abina, LMO2—associated clonal T cell proliferation in two patients after gene therapy for SCID-X1 [erratum appears in Science Oct. 24, 2003;302(5645):568]. 2003 *Science*, 302(5644):415-9.
Hacein-Bey-Abina, "Outcomes following gene therapy in patients with severe Wiskott-Aldrich syndrome" 2015 *JAMA*, 313(15):1550-63.
Haladjova, "DNA encapsulation via nanotemplates from cationic block copolymer micelles" 2012 *Soft Matter*, 8:2884.
Hallgren, "Physical exercise and internet-based cognitive-behavioural therapy in the treatment of depression: randomised controlled trial" 2015 *The British journal of psychiatry: the journal of mental science*, 207(3):227-34.
Hermann, "Polymergebundene Cinchonaalkaloide als Katalysatoren in derMichael Reaktion" 1977 *Helv. Chim. Acta*, 60(7):2208-2212.
Hiemenz, *Polymer Chemistry, Second Edition*. CRC Press; 2007. Cover page, title page and table of contents.
Hocum, "VISA—Vector Integration Site Analysis server: a web-based server to rapidly identify retroviral integration sites from next-generation sequencing" 2015 *BMC Bioinformatics*, 16:212.
Hodge, "Michael reactions catalysed by polymer-supported quaternary ammonium salts derived from cinchona and ephedra alkaloids" 1983 *J. Chem. Soc. Perkin Trans.* 1, 1(399):2205.
Horn, "Efficient lentiviral gene transfer to canine repopulating cells using an overnight transduction protocol" May 2004 *Blood*, 103(10):3710-6.
Horn, "Stem cell gene transfer—efficacy and safety in large animal studies" Sep. 2004 *Mol Ther.*, 10(3):417-31.
Hornback, *Organic Chemistry*, 2nd ed.; Thomson Brooks/Cole, 2006. Cover page, title page, table of contents.
Ingle, "Spatiotemporal cellular imaging of polymer-pDNA nanocomplexes affords in situ morphology and trafficking trends" 2013 *Mol Pharm.*, 10(11):4120-35.
Jacobsen, "Asymmetric Dihydroxylation via Ligand-Accelerated Catalysis" 1988 *J. Am. Chem. Soc.*, 110:1968-1970.
Jewell, "Surface-mediated delivery of DNA: Cationic polymers take charge" 2008 *Curr. Opin. Colloid Interface Sci.*, 13(6):395-402.
Jung, "Complexation between DNA and Hydrophilic-Cationic Diblock Copolymers" 2017 *J. Phys. Chem. B,*, 121(10)2230-2243.
Kabanov, "DNA complexes with polycations for the delivery of genetic material into cells" 1995 *Bioconjug. Chem.*, 6 (1):7-20.
Kaufman, "The quest for quinine: Those who won the battles and those who won the war" 2005 Angew. Chemie—Int. Ed., 44(6):854-885.
Kelcar, "Lanthanide-containing polycations for monitoring polyplex dynamics via lanthanide resonance energy transfer" May 2014 *Biomacromolecules*, 15(5):1612-24.
Kelcar, "Theranostics: combining imaging and therapy" Oct. 2011 *Bioconjug Chem.*, 22(10):1879-903.
Kennedy, "The cationic isomerization polymerization of 3-methyl-1-butene and 4-methyl-1-pentene" 1975 *Polym. React.*, 57-95.
Kiem, "Charting a clear path: the ASGCT Standardized Pathways Conference" Jul 2014 *Mol Ther.*, 22(7):1235-1238.
Kiem, "Hematopoietic stemcell-based gene therapy for HIV disease" Feb. 2012 *Cell Stem Cell*, 10(2):137-47.
Kiem, "Retrovirus-mediated gene transduction into canine peripheral blood repopulating cells" 1994 *Blood*, 83:1467-1473.
Kiem, "Pigtailed macaques as a model to study long-term safety of lentivirus vector-mediated gene therapy for hemoglobinopathies" 2014 *Molecular Therapy—Methods and Clinical Development*, 1:14055.

(56) References Cited

OTHER PUBLICATIONS

Kizjakina, "Cationic glycopolymers for the delivery of pDNA to human dermal fibroblasts and rat mesenchymal stem cells" 2012 *Biomaterials*, 33(6):1851-62.
Kobayashi, "Functional polymers. 1. Poly(cinchona alkaloid-co-acrylonitrile)s. New polymer catalysts for asymmetric synthesis" 1978 *J. Am. Chem. Soc.*, 100(22):7071-7072.
Kretzmann, "Synthetically controlling dendrimer flexibility improves delivery of large plasmid DNA" 2017 *Chemical science*, 8(4):2923-30. Epub Apr. 30, 2017.
Kuhar, "Novel fluorescent genome editing reporters for monitoring DNA repair pathway utilization at endonuclease-induced breaks" 2014 *Nucleic Acids Res.*, 42(1):e4.
Laemmli, "Characterization of DNA condensates induced by poly(ethylene oxide) and polylysine" 1975 *Proc. Natl. Acad. Sci. U. S. A.*, 72 (11):4288-4292.
Lee, "Glucose-based poly(ester amines): Synthesis, degradation, and biological delivery" 2012 *ACS Macro Lett.*, 1 (12):1388-1392.
Lee, "Polymeric chiral phase-transfer catalysts derived from cinchona alkaloids for enantioselective synthesis of ??-amino acids" 2007 Tetrahedron, 63(33):7906-7915.
Lee, "Synthetically modified guide RNA and donor DNA are a versatile platform for CRISPR-Cas9 engineering" 2017 *Elife*, 6.
Li, "Poly(2 deoxy 2 methacrylamido glucopyranose) b Poly(methaciylate amine)s: Optimization of Diblock Glycopoly cations for Nucleic Acid Delivery" 2013 *ACS Macro Lett.*, 2.
Li, "Artificial Virus Delivers CRISPR-Cas9 System for Genome Editing of Cells in Mice" 2017 ACS Nano., 11(1):95-111. Epub Jan. 25, 2017.
Liang, "Endosomal Escape Pathways for Non-Viral Nucleic Acid Delivery Systems" 2012 *Mol. Regul. Endocytosis*, 429-456.
Liu, "Hydroxyl stereochemistry and amine number within poly(glycoamidoamine)s affect intracellular DNA delivery" 2005 *J. Am. Chem. Soc.*, 127 (9):3004-3015.
Lynn, "pH-Responsive Polymer Microspheres: Rapid Release of Encapsulated Material within the Range of Intracellular pH Financial support was provided by the NSF (Cooperative Agreement No. ECC9843342 to the MIT Biotechnology Process Engineering Center):the NIH" 2001 *Angew. Chem. Int. Ed. Engl.*, 40 (9):1707-1710.
Marcelli, "Cinchona alkaloids in asymmetric organocatalysis" 2010 *Synthesis* (Stuttg)., No. 8, 1229-1279.
Marshall, "A renewed assault on an old and deadly foe" 2000 *Science*, 290(5491):428-430.
McLendon, "Poly(glycoamidoamine) vehicles promote pDNA uptake through multiple routes and efficient gene expression via caveolae-mediated endocytosis" Jun. 2010 Mol Pharm., 7(3):738-50.
McNeish, "Gene therapy progress and prospects: cancer gene therapy using tumour suppressor genes" 2004 *Gene Ther.*, 11(6):497-503.
Merkel, "Stability of siRNA polyplexes from poly(ethylenimine) and poly(ethylenimine)-g-poly(ethylene glycol) under in vivo conditions: Effects on pharmacokinetics and biodistribution measured by Fluorescence Fluctuation Spectroscopy and Single Photon Emission" 2009 *Com. J. Control. Release*, 138(2):148-159.
Mindell, "Lysosomal Acidification mechanisms" 2012 *Annu Rev Physiol.*, 74:69-86.
Mintzer, "Nonviral Vectors for Gene Delivery" 2009 *Chem. Rev.*, 109 (2):259-302.
Mishra, "Dexamethasone-loaded reconstitutable charged polymeric (PLGA) n-b-bPEI micelles for enhanced nuclear delivery of gene therapeutics" 2014 *Macromol. Biosci.*, 14(6):831-841.
Moad, "RAFT polymerization and some of its applications" 2013 *Chem.-An Asian J.*, 8(8):1634-1644.
Moad, "Toward Living Radical Polymerization" 2008, 41 (9):1133-1142.
Moon, "Heterogeneous catalytic asymmetric dihydroxylation: Use of a polymer-bound alkaloid" 1990 *Tetrahedron Lett.*, 31 (21):3003-3006.
Mortimer, "Free-Radical Polymerization of Olefins" 1964 *J Polym Sci.*, 2, 4247-4253.
Mosmann, "Rapid colorimetric assay for cellular growth and survival: Application to proliferation and cytotoxicity assays" 1983 *J. Immunol. Methods*, 65 (1-2):55-63.
Mukherjee, "Endocytosis" 1997 *Physiol. Rev.*, 77(3):759-803.
Murovec, "New variants of CRISPR RNA-guided genome editing enzymes" 2017 *Plant biotechnology journal*. Epub Apr. 4, 2017.
Neff, "Methylguanine methyltransferase-mediated in vivo selection and chemoprotection of allogeneic stem cells in a large-animal model" Nov. 2003 *J Clin Invest.*, 112(10):1581-1588.
Nelson, "Balancing cationic and hydrophobic content of PEGylated siRNA polyplexes enhances endosome escape, stability, blood circulation time, and bioactivity in vivo" 2013 *ACS Nano*, 7(10):8870-8880.
Nguyen, "Firefly luciferase luminescence assays using scintillation counters for quantitation in transfected mammalian cells" 1988 *Anal. Biochem.*, 171 (2):404-408.
Odian, *Principles of Polymerization, Fourth.*; John Wiley & Sons: Hoboken, New Jersey, 2004.
Ogris, "PEGylated DNA/transferrin-PEI complexes: reduced interaction with blood components, extended circulation in blood and potential for systemic gene delivery" 1999 Gene Ther., 6(4):595-605 DOI: 10.1038/sj.gt.3300900.
Ogris, "Targeting tumors with non-viral gene delivery systems" 2002 Drug Discov Today, 7 (8):479-485.
Olszko, "Foamy viral vector integration sites in SCID-repopulating cells after MGMTP140K-mediated in vivo selection" Jul. 2015 *Gene Ther.*, 22(7): 591-595.
O'Reilly, "Fluorescence experiments with quinine" 1975 *J Chem Educ.*, 52(9):610-2.
Osborn, "TALEN-based gene correction for epidermolysis bullosa" 2013 *Mol. Ther.*, 21 (6):1151-1159.
Otsu, "The reactivities of alkyl methacrylates in their radical polymerizations" 1965 *J. Polym. Sci. Part B Polym. Lett.*, 3,113-117.
Ott, "Correction of X-linked chronic granulomatous disease by gene therapy, augmented by insertional activation of MDSI-EVII, PRDM16 or SETBP1" 2006 *Nature Medicine*, 12(4):401-9.
Pack, "Design and development of polymers for gene delivery" 2005 *Nat. Rev. Drug Discov.*, 4 (7):581-593.
Papapetrou, "Gene Insertion Into Genomic Safe Harbors for Human Gene Therapy" 2016 *Mol Ther.*, 24(4):678-84.
Papapetrou, "Genetic modification of hematopoietic stem cells with nonviral systems: past progress and future prospects (Review)" 2005 *Gene Therapy*, 12 (Suppl. 1):S118-S30. PubMed PMID: 16231044.
Papapetrou, "Genomic safe harbors permit high beta-globin transgene expression in thalassemia induced pluripotent stem cells" 2011 *Nature Biotechnology*, 29(1):73-8.
Peister, "Stable transfection of MSCs by electroporation" 2004 *Gene Ther.*, 11(2):224-8.
Perdoni, "Gene editing toward the use of autologous therapies in recessive dystrophic epidermolysis bullosa" 2015 *Transl. Res.*, 168 (June):1-9.
Peterson, "Lack of viral control and development of combination antiretroviral therapy escape mutations in macaques after bone marrow transplantation" Aug. 2015 *AIDS*, 29(13):1597-606.
Peterson, "Loss of immune homeostasis dictates SHIV rebound after stem-cell transplantation" Feb. 2017 *JCI Insight*, 2(4):e91230.
Peterson, "Multilineage polyclonal engraftment of Cal-1 gene-modified cells and in vivo selection after SHIV infection in a nonhuman primate model of AIDS" 2016 *Mol Ther Methods Clin Dev.*, 3:16007.
Peterson, "Long-term multilineage engraftment of autologous genome-edited hematopoietic stem cells in nonhuman primates" 2016 *Blood*, 127(20):2416-26.
Prevette, "Amide spacing influences pDNA binding of poly(amidoamine)s" Feb. 2010 *Biomacromolecules*, 11(2):326-32.
Prevette, "Correlation of amine No. and pDNA binding mechanism for trehalose-based polycations" Aug. 2008 *Langmuir*, 24(15):8090-101.

(56) References Cited

OTHER PUBLICATIONS

Qasim, "Molecular remission of infant BALL after infusion of universal TALEN gene-edited CAR T cells" 2017 *Sci Transl Med.*, 9(374).
Radtke, "A distinct hematopoietic stem cell population for rapid multilineage engraftment in nonhuman primates" Nov. 2017 *Sci Transl Med.*, 9(414).
Ran, "Genome engineering using the CRISPR-Cas9 system" 2013 *Nat. Protoc.*, 8 (11):2281-2308.
Ran, "Double nicking by RNA-guided CRISPR Cas9 for enhanced genome editing Specificity" 2013 *Cell* 154(6):1380-9.
Reineke, "Stimuli-Responsive Polymers for Biological Detection and Delivery" 2015 *ACS Macro Lett.*, 14-18.
Riccardi, "Analysis of apoptosis by propidium iodide staining and flow cytometry" 2006 *Nat. Protoc.*, 1 (3):1458-1461.
Richardson, "Enhancing homology-directed genome editing by catalytically active and inactive CRISPR-Cas9 using asymmetric donor DNA" 2016 *Nat Biotechnol.*, 34(3):339-44.
Rocha, "Time-resolved fluorescence spectroscopy of quinine dication free and bound to polymethacrylic acid" 1999 *J. Photochem. Photobiol. A Chem.*, 123 (1-3):129-136.
Ropp, "Aequorea green fluorescent protein analysis by flow cytometry" 1995 *Cytometry*, 21(4):309-317.
Rowan, "Macrocycles derived from cinchona alkaloids: A thermodynamic vs kinetic study" 1998 *J.Org.Chem.*, 63(12):1536.
Sessa, "Lentiviral haemopoietic stem-cell gene therapy in early-onset metachromatic leukodystrophy: an ad-hoc analysis of a non-randomised, open-label, phase 1/2 trial" 2016 *Lancet*, 388(10043)476-87.
Sizovs, "Poly(trehalose): sugar-coated nanocomplexes promote stabilization and effective polyplex-mediated siRNA delivery" 2013 *J Am Chem Soc.*, 135(41):15417-24.
Sonawane, "Chloride Accumulation and Swelling in Endosomes Enhances DNA Transfer by Polyamine-DNA Polyplexes" 2003 *J. Biol. Chem.*, 278(45)44826-44831.
Song, "An Overview of Cinchona Alkaloids in Chemistry. Cinchona Alkaloids Synth. Catal. Ligands, Immobil" 2009 *Organocatalysis*, 1-10.
Sprouse, "Investigating the effects of block versus statistical glycopolycations containing primary and tertiary amines for plasmid DNA delivery" 2014 *Biomacromolecules*, 15(7):2616-28.
Sprouse, "Polymeric delivery vehicles for exogenous nucleic acid delivery" in: Hashmi, *Reference Module in Materials Science and Materials Engineering*: Elsevier; 2016. Cover page, title page, table of contents and this chapter.
Srinivasachari, "Polycationic beta-cyclodextrin "click clusters": monodisperse and versatile scaffolds for nucleic acid delivery" Apr. 2008 *J Am Chem Soc.*, 130(14):4618-27.
Stein, "Genomic instability and myelodysplasia with monosomy 7 consequent to EII activation after gene therapy for chronic granulomatous disease" 2010 *Nature Medicine*, 16(2):198-204.
Sun, "Self-assembled DNA nanoclews for the efficient delivery of CRISPR-Cas9 for genome editing" 2015 *Angewandte Chemie (International ed in English)*, 54(41):12029-33.
Tebas, "Gene editing of CCR5 in autologous CD4 T cells of persons infected with HIV" 2014 *New England Journal of Medicine*, 370(10):901-10.
Thiele, "Competitive adsorption of serum proteins at microparticles affects phagocytosis by dendritic cells" 2003 *Biomaterials*, 24 (8):1409-1418.
Ting, "Deconstructing HPMCAS: Excipient Design to Tailor Polymer—Drug Interactions for Oral Drug Delivery" 2015 *ACS Biomater. Sci. Eng.*, 1 (10):978-990.
Ting, "Design of Tunable Multicomponent Polymers as Modular Vehicles to Solubilize Highly Lipophilic Drugs" Oct. 2014 *Macromolecules*, 47(19):6554-6565.
Ting, "High-Throughput Excipient Discovery Enables Oral Delivery of Poorly Soluble Pharmaceuticals" 2016 *ACS Cent. Sci.*, 2(10):748-755.
Ting, "Precise compositional control and systematic preparation of multimonomeric statistical copolymers" 2013 *ACS Macro Lett.*, 2(9):770-774.
Tolar, "Induced pluripotent stem cells from individuals with recessive dystrophic epidermolysis bullosa" 2011 *J. Invest. Dermatol.*, 131(4):848-856.
Tolar, "Stem cell gene therapy for fanconi anemia: report from the 1st international Fanconi anemia gene therapy working group meeting" Jul. 2011 *Mol Ther.*, 19(7):1193-8.
Tolarova, "From Mesoderm to Mesodermatology: Bone Marrow Mesenchymal Cells Heal Skin Wounds" 2015 *Mol. Ther.*, 23 (8):1283-1284.
Tolstyka, "Trehalose-Based Block Copolycations Promote Polyplex Stabilization for Lyophilization and in Vivo pDNA Delivery" 2016 *ACS Biomaterials Science & Engineering*. 2(1):43-55.
Toncheva, "Novel vectors for gene delivery formed by self-assembly of DNA with poly(L-lysine) grafted with hydrophilic polymers" 1998 *Biochim. Biophys. Acta—Gen.Subj.*, 1380(3):354-368.
Tranter, "In vivo delivery of nucleic acids via glycopolymer vehicles affords therapeutic infarct size reduction in vivo" 2012 *Mol Ther.*, 20(3):601-8.
Trivedi, "Nanomicellar formulations for sustained drug delivery: strategies and underlying principles" 2010 *Nanomedicine*, 5(3):485-505.
Van Deutekom, "Advances in Duchenne muscular dystrophy gene therapy" 2003 *Nat. Rev. Genet.*, 4 (10):774 783.
Verkman, "Development and biological applications of chloride-sensitive fluorescent indicators" 1990 *Am. J. Physiol.*, 259(3 Pt 1):C375-88.
Wagner, "Bone marrow transplantation for recessive dystrophic epidermolysis bullosa" 2010 *N. Engl. J. Med.*, 3 63(7):629-639.
Wang, "Rapamycin relieves lentiviral vector transduction resistance in human and mouse hematopoietic stem cells" Aug. 2014 *Blood*, 7;124(6):913-23.
Webber, "From marrow to matrix: novel gene and cell therapies for epidermolysis bullosa" 2015 *Mol. Ther.*, 23(6):987-992.
Widanapathtrana, "Dissolution and Solubility Enhancement of the Highly Lipophilic Drug Phenytoin via Interaction with Poly(N-isopropylaciylamide-co-vinylpyrrolidone) Excipients" 2015 *Mol. Pharmaceutics*, 12 (7):2537-2543.
Wolff, *Burger's Medicinal Chemistry and Drug Discovery, Therapeutic agents*, vol. 3: Wiley: Hoboken, NJ; 1996. Cover page, title page, table of contents.
Wu, "Receptor-mediated gene delivery and expression in vivo" 1988 *J. Biol. Chem.*, 263(29):14621-14624.
Wu, "Glucose-containing diblock poly cations exhibit molecular weight, charge, and cell-type dependence for pDNA delivery" 2014 *Biomacromolecules*, 15(5):1716-26.
Xue, "Highlighting the role of polymer length, carbohydrate size, and nucleic acid type in potency of glycopoly cation agents for pDNA and siRNA delivery" 2013 *Biomacromolecules*, 14(11):3903-15.
Yan, "BLISS is a versatile and quantitative method for genome-wide profiling of DNA double-strand breaks" 2017 *Nat Commun.*, 8:15058.
Yin, "Delivery technologies for genome editing" 2017 *Nat Rev Drug Discov.*, 16:387-399.
Yin, "Glucose-functionalized, serum-stable polymeric micelles from the combination of anionic and RAFT polymerizations" 2012 *Macromolecules*, 45(10):4322-32.
Younan, "Positive selection of mC46-expressing CD4+ T cells and maintenance of virus specific immunity in a primate AIDS model" Jul. 2013 *Blood*, 11;122(2):179-87.
Zetsche, "Cpf1 is a single RNA-guided endonuclease of a class 2 CRISPR-Cas system" 2015 *Cell*, 163(3):759-71.
Zhong, "Efficient generation of nonhuman primate induced pluripotent stem cells" May 2011 *Stem Cells Dev.*, 20(5):795-807.
Zuckerman, "Correlating animal and human phase Ia/Ib clinical data with CALAA-01, a targeted, polymer-based nanoparticle containing siRNA" 2014 *Proc Natl Acad Sci U S A*, 111(31):11449-54.

(56) References Cited

OTHER PUBLICATIONS

Zuris, "Cationic lipid-mediated delivery of proteins enables efficient protein-based genome editing in vitro and in vivo" 2015 *Nat Biotechnol.*, 33(1):73-80.

* cited by examiner

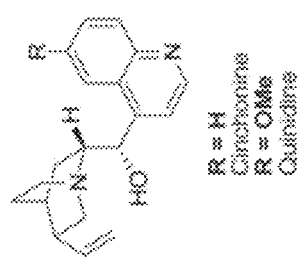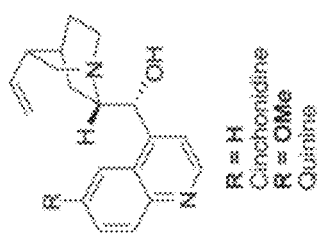
FIG. 1

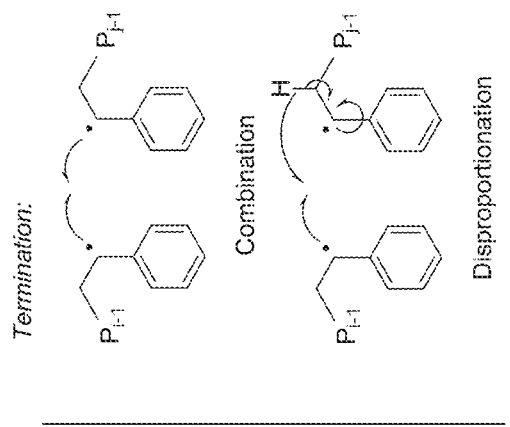
FIG. 3A *Initiation:*
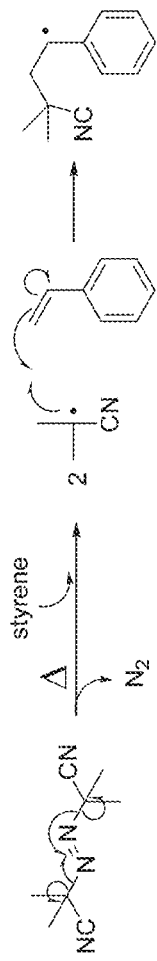
FIG. 3B *Propagation:*
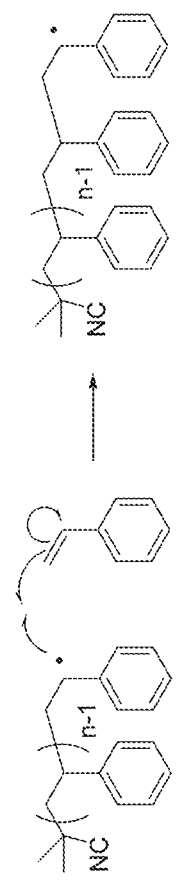
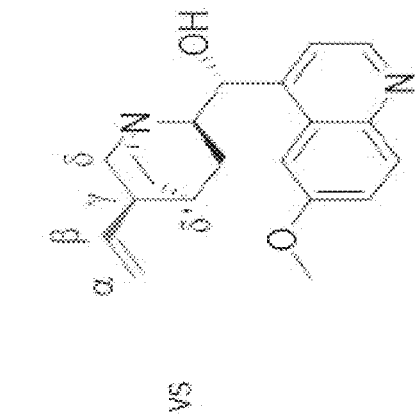
FIG. 3C *Termination:*
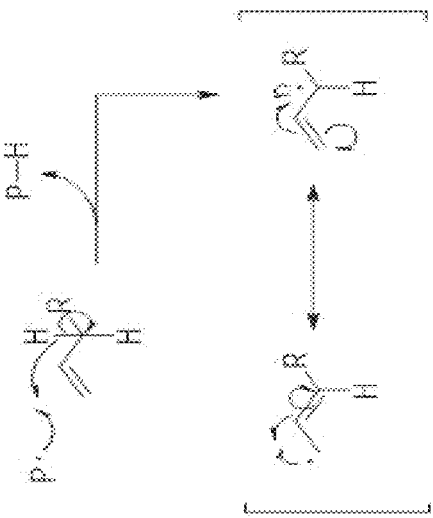
FIG. 4A
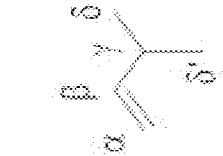
FIG. 4B

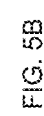
FIG. 5A
FIG. 5B
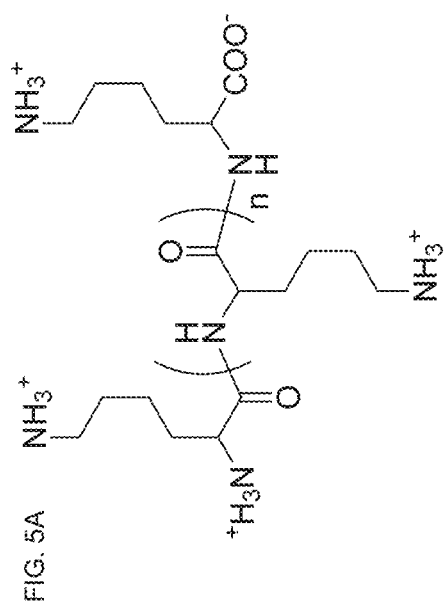
FIG. 6A
FIG. 6B
FIG. 6C
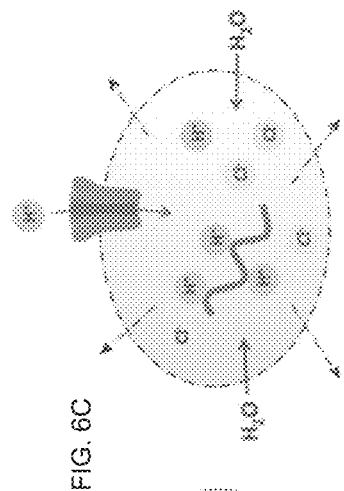
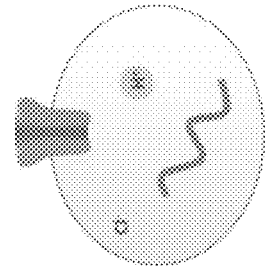

R = H or point of polymer branching

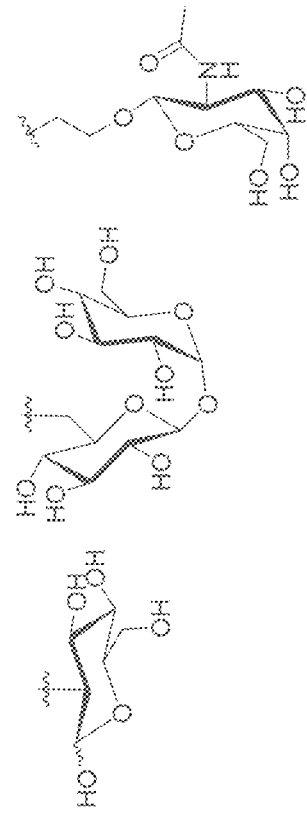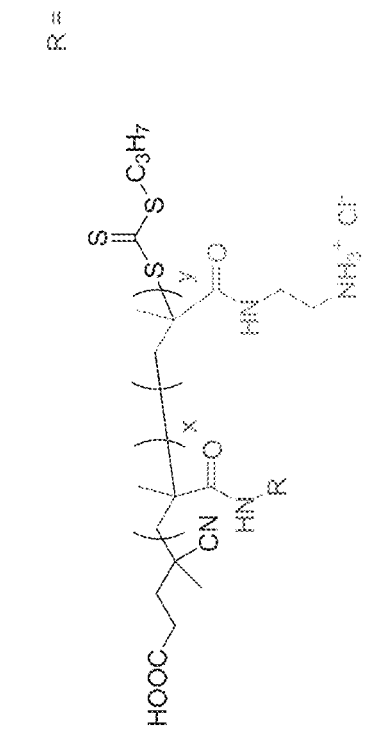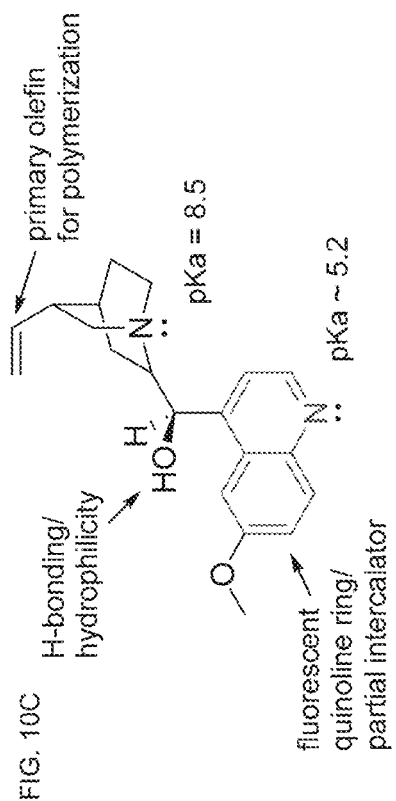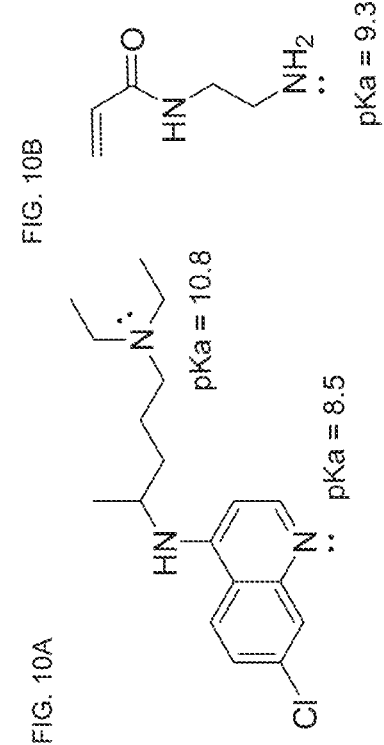
FIG. 9A  FIG. 9B  FIG. 9C
FIG. 10A  FIG. 10B  FIG. 10C

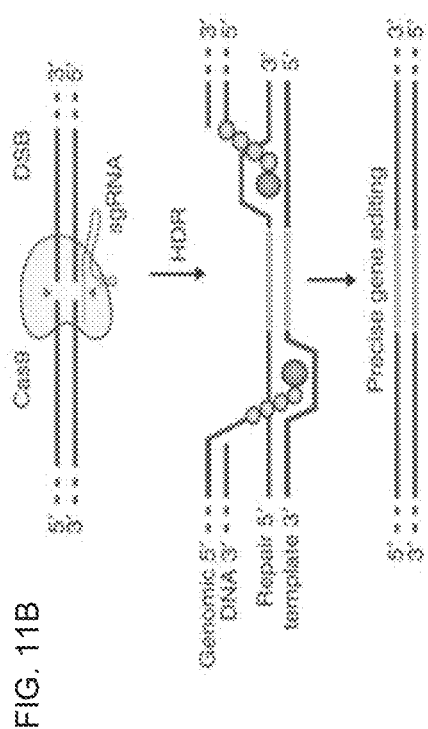
FIG. 11B
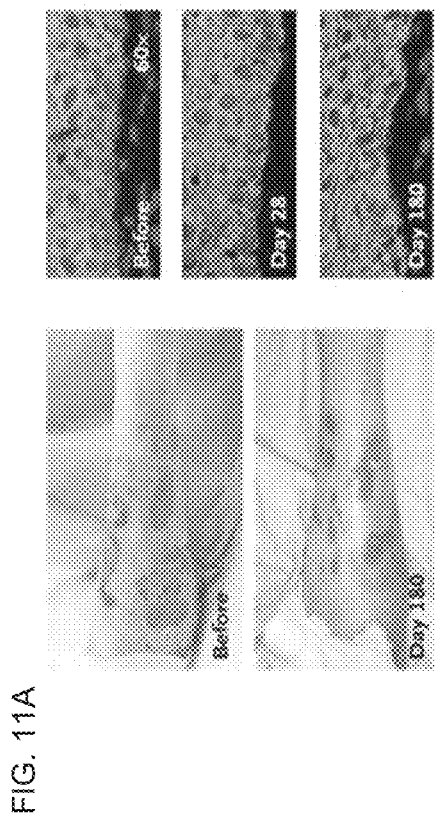
FIG. 11A
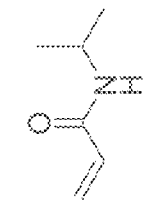
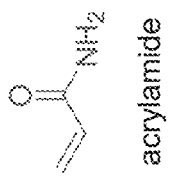
FIG. 12B
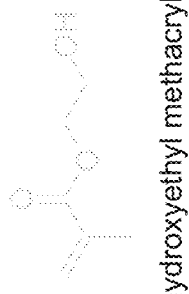
FIG. 12A

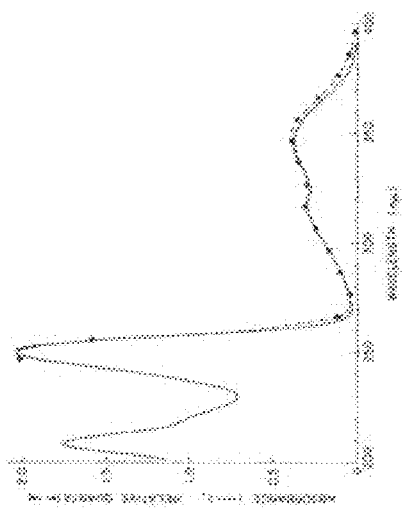
FIG. 13A
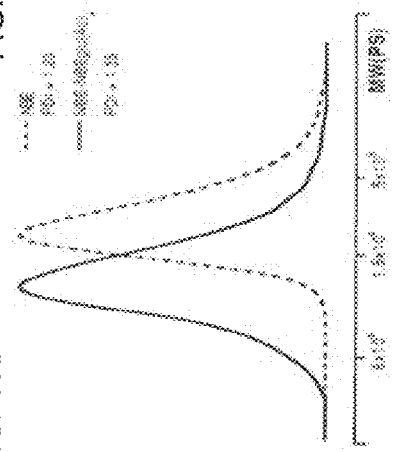
FIG. 13B
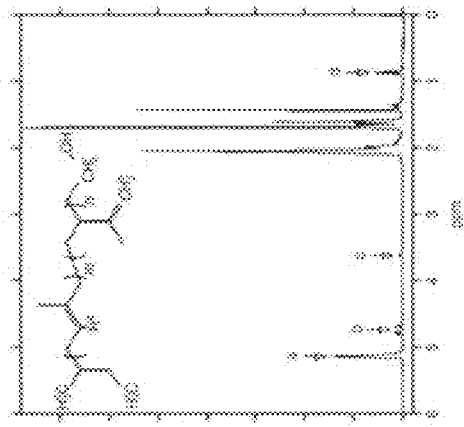
FIG. 13C
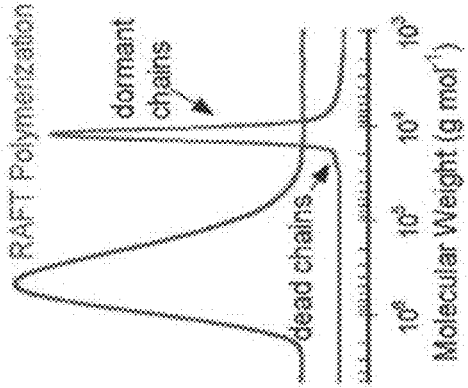
FIG. 14B Conventional Polymerization / RAFT Polymerization
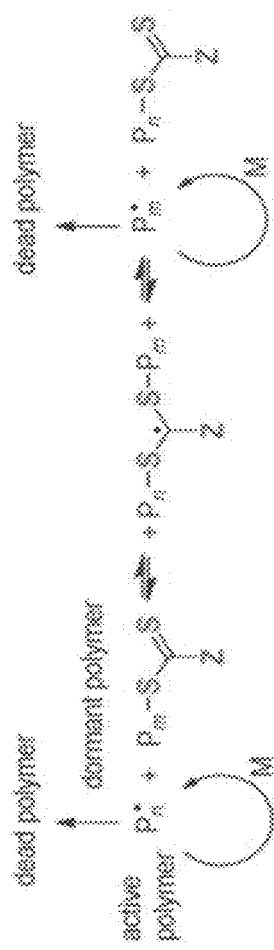
FIG. 14A

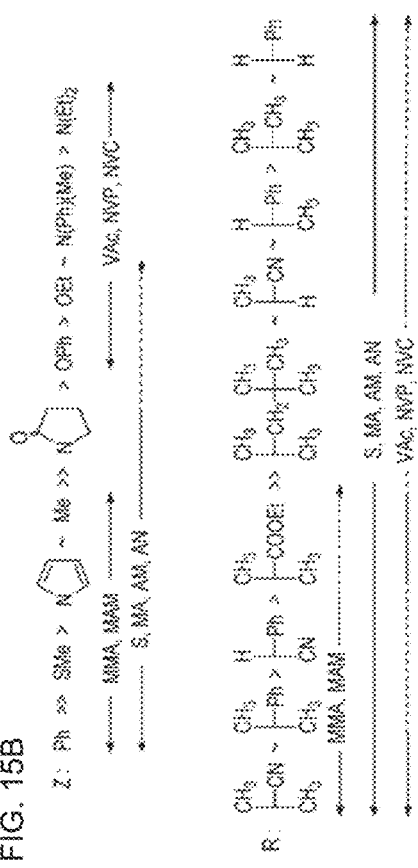
FIG. 15A
FIG. 15B
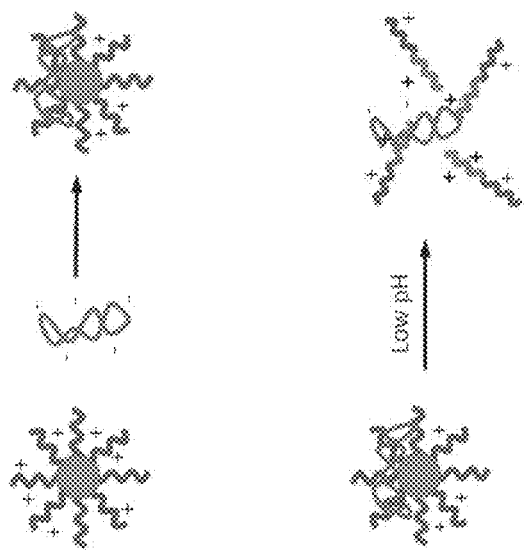
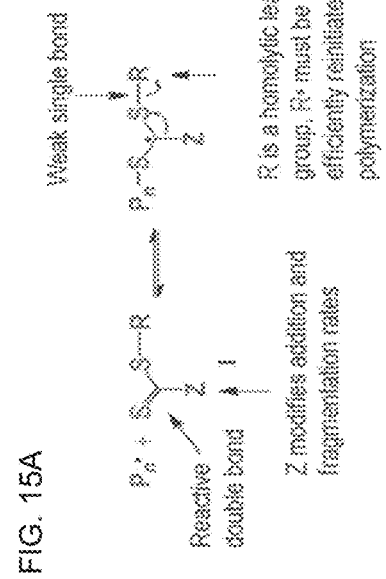
FIG. 16A
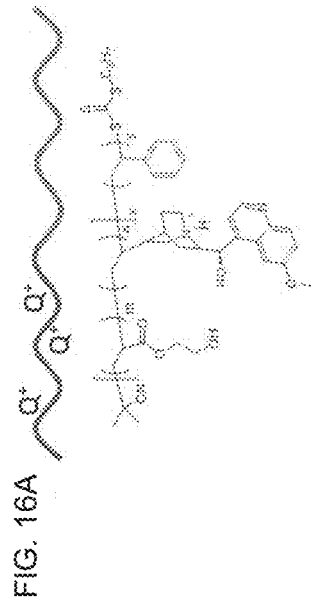
FIG. 16B
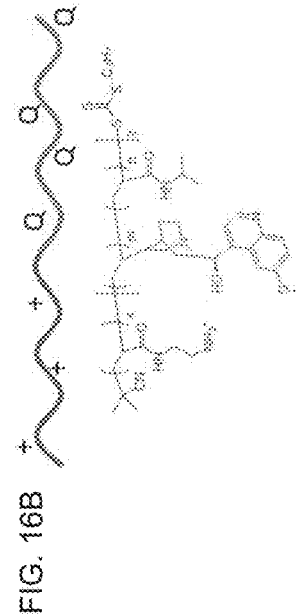

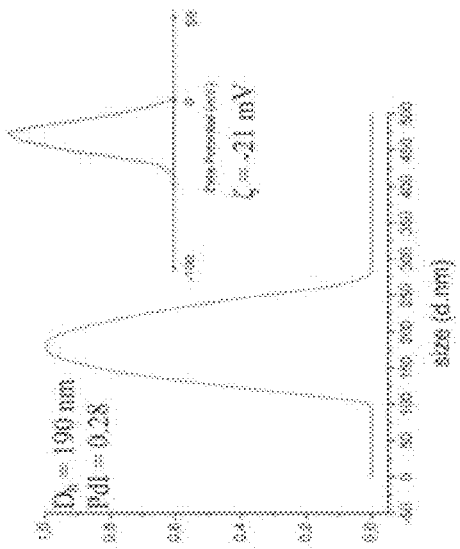
FIG. 17A
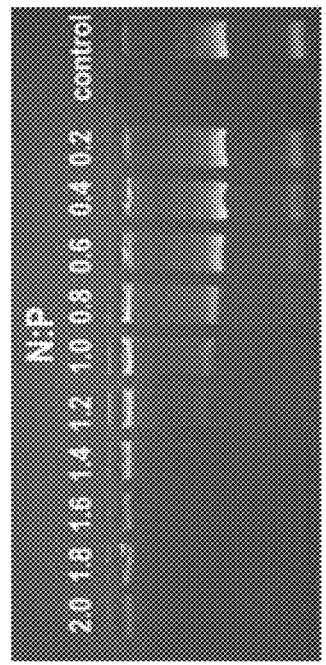
FIG. 17B
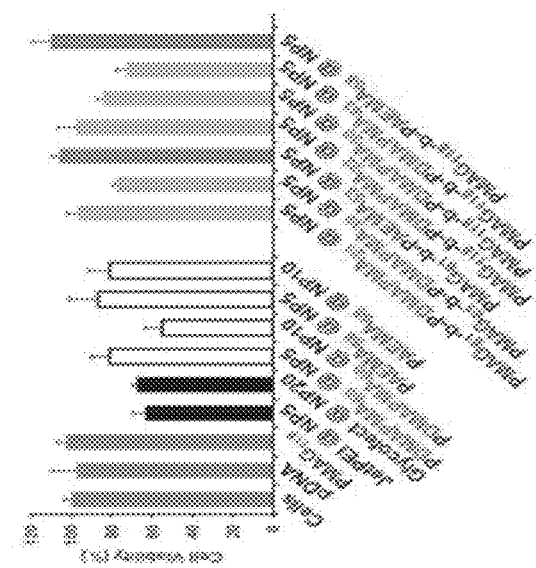
FIG. 18A
FIG. 18B
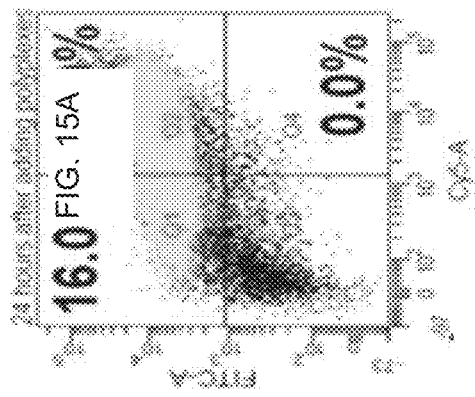
FIG. 18C

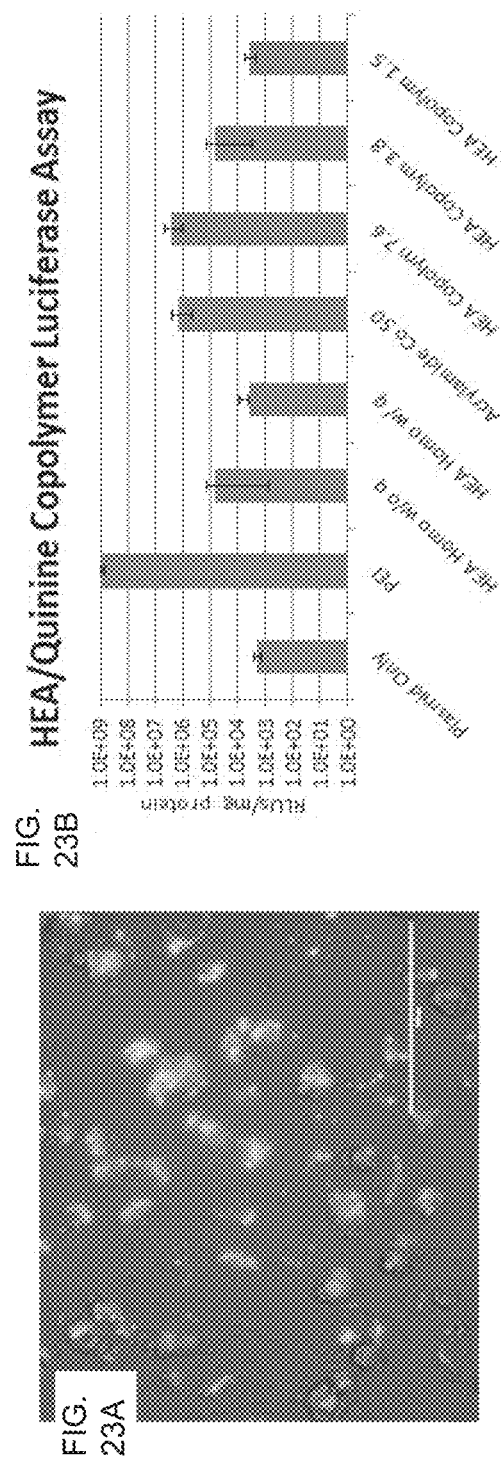

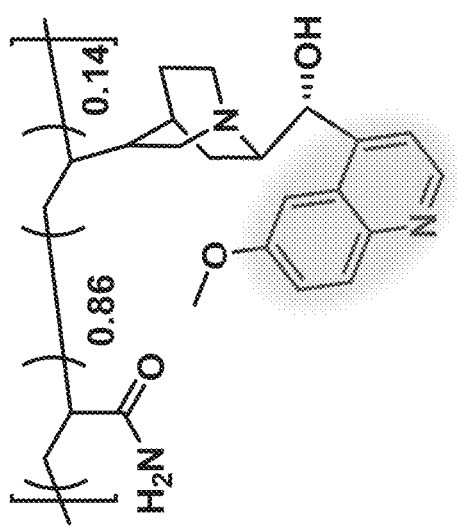
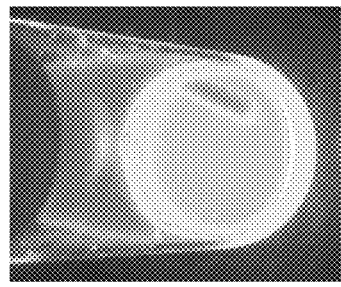
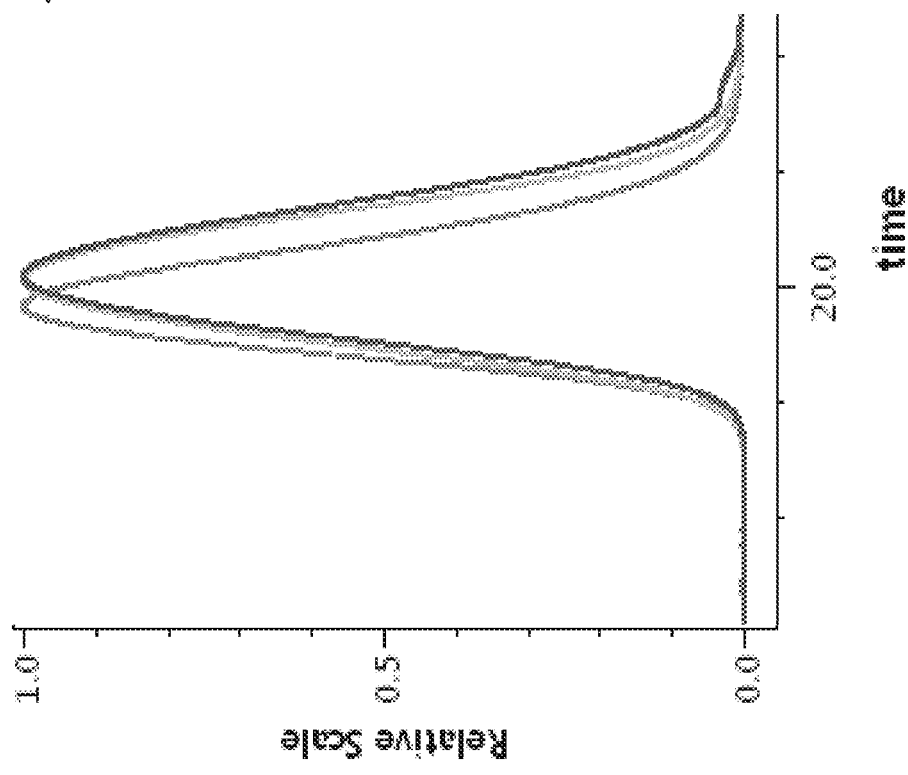
FIG. 35A
FIG. 35B

| Polymer | Q17 | Q14 | Q10 | Q6 | Q3 | Q0 |
|---|---|---|---|---|---|---|
| % Q in Feedstock | 50 | 40 | 33 | 15 | 10 | 0 |
| % Q in Polymer | 17 | 14 | 10 | 6 | 3 | 0 |
| $M_n$ (kDa) | 15 | 20 | 23 | 108 | 42 | 17 |
| Đ | 1.44 | 1.76 | 2.71 | 4.05 | 4.47 | 2.5 |
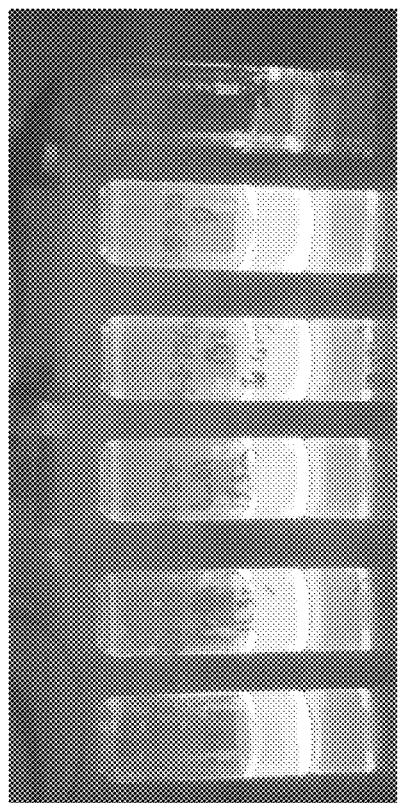
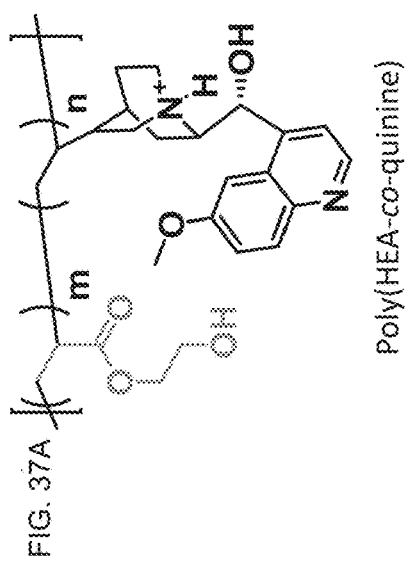
FIG. 37A  Poly(HEA-co-quinine)
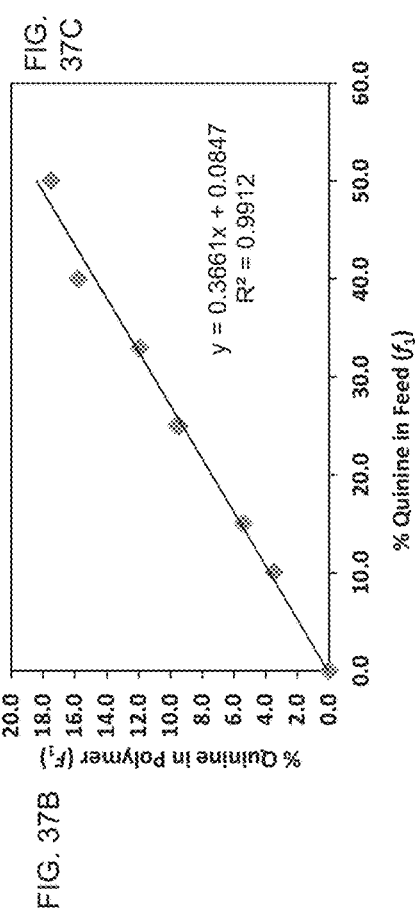
FIG. 37B
FIG. 37C

* = Luc Expression: statistical significance between jPEI (t-test, with p-value < 0.05)
** = BCA Toxicity: statistical significance between jPEI (t-test, with p-value < 0.05)

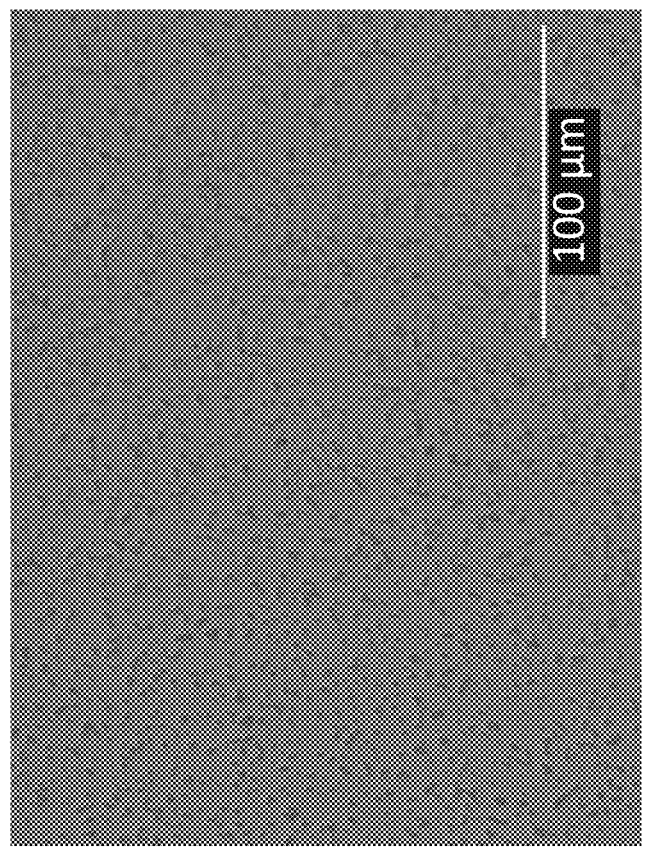
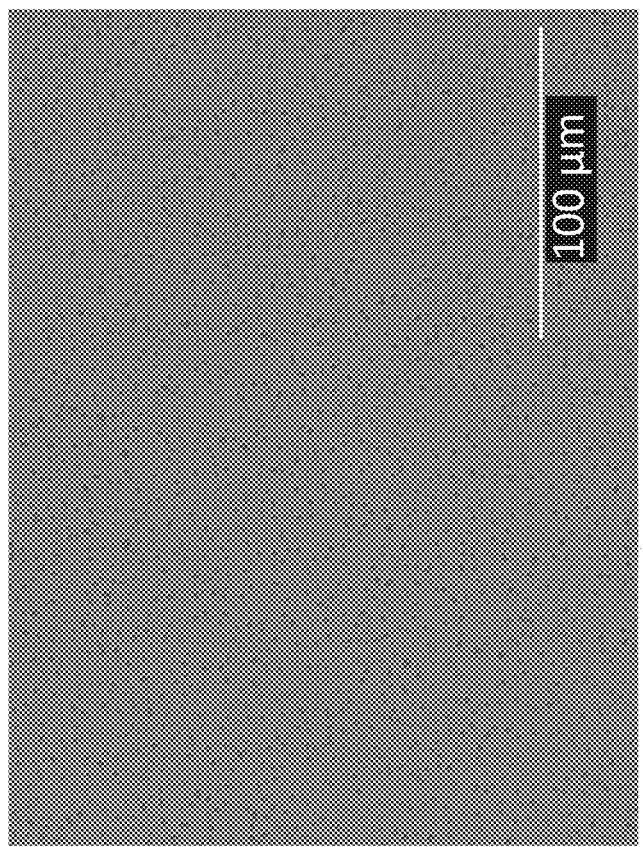
FIG. 41

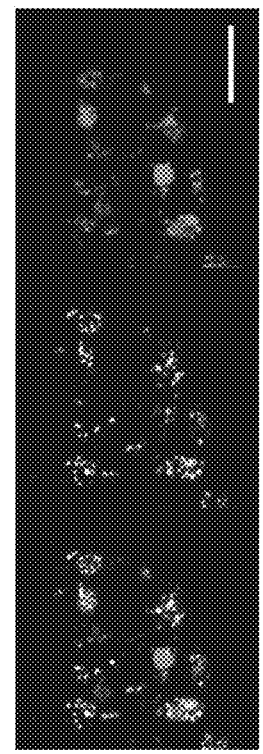
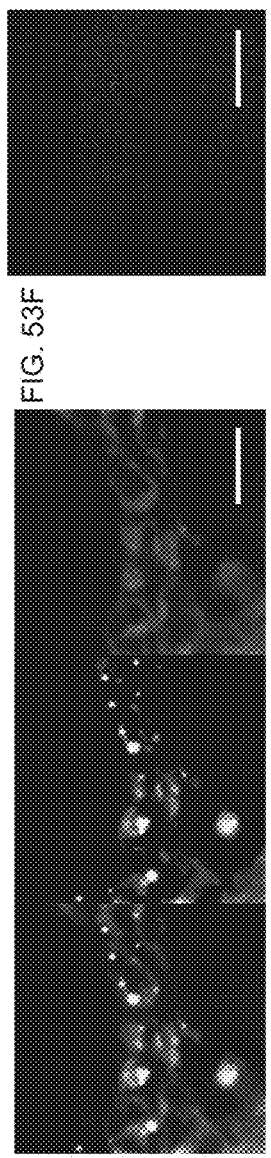
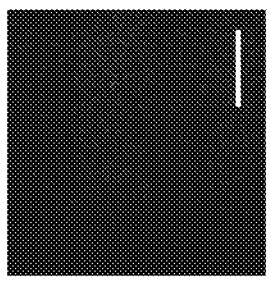
FIG. 53A  FIG. 53B  FIG. 53C  FIG. 53D  FIG. 53E  FIG. 53F

COPOLYMERS INCLUDING CINCHONA ALKALOID COMPONENTS AND ONE OR MORE ACRYLAMIDE OR ACRYLATE CONTAINING COMPONENTS, COMPLEXES CONTAINING THE SAME, AND METHODS OF USING THE

PRIORITY

This application claims priority to U.S. Provisional Application No. 62/536,427 filed on Jul. 24, 2017 entitled COPOLYMERS INCLUDING CINCHONA ALKALOID COMPONENTS AND ONE OR MORE ACRYLAMIDE OR ACRYLATE CONTAINING COMPONENTS, COMPLEXES CONTAINING THE SAME, AND METHODS OF USING THE SAME, the entire disclosure of which is incorporated herein by reference thereto.

SUMMARY

Disclosed herein are copolymers polymerized from at least one or more cinchona alkaloid containing compounds; and an acrylamide containing monomer, an acrylate containing monomer, or combinations thereof.

Also disclosed are methods of forming a copolymer that includes the step of combining one or more cinchona alkaloid containing compounds with at least an acrylamide containing monomer, an acrylate containing monomer, or combinations thereof.

Also disclosed are methods of forming a complex, the methods including combining a copolymer according to disclosed copolymers with at least one genetic component to form a copolymer-genetic component complex.

Also disclosed are copolymer-genetic component complexes prepared according to a disclosed methods.

Also disclosed are methods of delivering a genetic component to a cell, the methods include delivering a copolymer-genetic component complex according to disclosed complexes to at least one cell.

The above brief description of various embodiments of the present disclosure is not intended to describe each embodiment or every implementation of the present disclosure. Rather, a more complete understanding of the disclosure will become apparent and appreciated by reference to the following description and claims in view of the accompanying drawings. Further, it is to be understood that other embodiments may be utilized and structural changes may be made without departing from the scope of the present disclosure.

BRIEF DESCRIPTION OF FIGURES

FIG. 1 shows the chemical structure of cinchona alkaloid family and their natural source, the bark of the cinchona tree.

FIGS. 3A, 3B, and 3C depict the steps in a free-radical polymerization mechanism.

FIGS. 4a and 4b depict proton abstraction of allylic olefin leading to degradative chain transfer (FIG. 4a) and a comparison of 3-methyl-1-butene (left) and quinine (right) (FIG. 4b).

FIGS. 5a and 5b show Poly-L-lysine (PLL) (FIG. 5a); and branched Polyethylenimine (PEI) (FIG. 5b).

FIGS. 6A, 6B and 6C show endosomal escape through polycation pH buffering ("proton sponge" theory). (6A) Polyplex entrapment in endosome, (6B) Polymer buffering during proton-pump acidification, (6C) Chloride influx leads to endosome rupture.

FIGS. 9A, 9B and 9C show various glycopolymers for nucleic acid delivery: (9A) poly(MAG-b-AEMA), (9B) poly(trehalose-b-AEMA), and (9C) poly(MAGalNac-b-AEMA).

FIGS. 10A, 10B and 10C show chemical structures of (10A) chloroquine, (10B) N-(2-aminoethyl) methacrylamide (AEMA), and (10C) quinine (outlined with properties amenable to gene delivery).

FIGS. 11A and 11B show clinical photographs of patient with EB treated with bone marrow transplant (BMT) containing allogeneic stem cells. FIG. 11A shows biopsy of blistered skin as it heals with increased levels of collagen VII (red) forming a layer of keratinocytes (green), 11B) Diagram of CRISPR/Cas9 induced DSB followed by HDR of target gene.

FIGS. 12A and 12B show simple, methylated monomers of olefin-containing monomer families for determining reactivity of quinine towards free-radical copolymerization. (12B) Hydrophilic monomers to be copolymerized with quinine for biological applications (color correlates with vinyl-group family).

FIGS. 13A, 13B and 13C show an example of $^1$H-NMR (13A) of a polymer (polyisoprene), 13B) Example of SEC trace of a polymer (polynorbornene), 13C) UV-Vis absorption spectrum of quinine.

FIGS. 14A and 14B show: 14A) RAFT main equilibration mechanism with reversible activation/deactivation by degenerate chain transfer, 14B) Molecular-weight distribution of polystyrene polymerized through conventional free-radical polymerization ($M_n$=324,000 g/mol, Đ=1.74) and RAFT polymerization ($M_n$=14,400 g/mol, Đ=1.04).

FIGS. 15A and 15B show: 15A) Properties of effective RAFT CTA agents, 15B) Guidelines for selecting RAFT CTA agents for various polymerizations.

FIGS. 16A and 16B show potential micelle-based gene delivery systems using diblock quinine copolymers made with RAFT: 16A) Micelle formation from diblock copolymer poly[(HEA-s-quinine)-b-styrene] and its binding of pDNA 16B) Micelle formation from diblock copolymer poly[AEMA-b-(quinine-s-NIPAm)] and its pH-triggered dissociation (blue=hydrophilic block, red=hydrophilic block).

FIGS. 17A and 17B show an example of gel electrophoresis (17A) of polyplexes (made from cationic cyclodextrin polyrotaxanes), 17B) Example of DLS and zeta potential (inset) measurements of polyplexes (made of polystyrene-based block copolymer micelles).

FIGS. 18A, 18B and 18C show an example of a flow cytometry plot (18A) and gating, a method that will be used with Cy5, GFP, and propidium iodide toxicity assays, 18B) Histogram of GFP gene expression in cells transfected using polymerized N-methyl aminoethylmethacrylate (PMAEMT), 18C) Histogram of cell viability after transfection with cationic glycopolymers at various N/P ratios determined using MTT assay.

FIGS. 23A and 23B show: 23A) Wide-field fluorescence microscopy image of HeLa cells 48 hours after luciferase transfection with poly(acrylamide-co-quinine) fluorescence visualized through DAPI filter. 23B) Luciferase assay transfection assay performed with poly(HEA-co-quinine) at several N/P ratios compared to controls including PEI, HEA homopolymer (with and without free quinine in solution), and poly(Am-co-quinine) (N/P=50) (RLUs=Relative Light Units).

FIG. 25a shows the 0 μg/mL puromycin plot and FIG. 25b shows the 1.0 μg/mL puromycin plot.

FIGS. 35A and 35B show: 35A) A size exclusion chromatography (SEC) trace of a poly(Am-co-quinine), which is representative of all quinine-copolymers produced. In the acidic aqueous mobile phase (0.1 M $NaSO_4$ and 1% acetic acid) the copolymer is UV-active and provides a UV trace that overlaps with the traces from light scattering (LS) and refractive index (RI) (UV detector, λ=311 nm), showing that quinine is present in all chains throughout the molar mass distribution. 35B) A picture of the same poly(Am-co-quinine) copolymer shown in the SEC trace exemplifies its ability to absorb UV light and fluoresce in the visible spectrum (λ=450 nm).

FIGS. 37A, 37B and 37C show: 37A) Structure and characterization data of HEA-quinine copolymers ranging in feed ratio of comonomers. 37B) Graph showing the linear dependence of the percentage of quinine present in feedstock and percentage of quinine in the total amount of isolated product. 37C) Picture of the fluorescence of HEA-quinine copolymers ranging in percentage of quinine polymer when dissolved in aqueous acetic acid solutions. All solutions prepared had equal molar concentration of quinine repeat units (except Q0 which had equivalent mass of HEA as Q3) and qualitatively showed equivalent levels of fluorescence while illuminated by a near-UV transilluminator.

Luciferase expression (left y-axis) is expressed as relative light units (RLUs) normalized over the total mass (mg) of protein quantified in the sample via a BCA protein assay. The fractional survival (right y-axis) is the total amount protein in the sample normalized to the amount of protein in "cells only" negative control sample.

Figure 39:
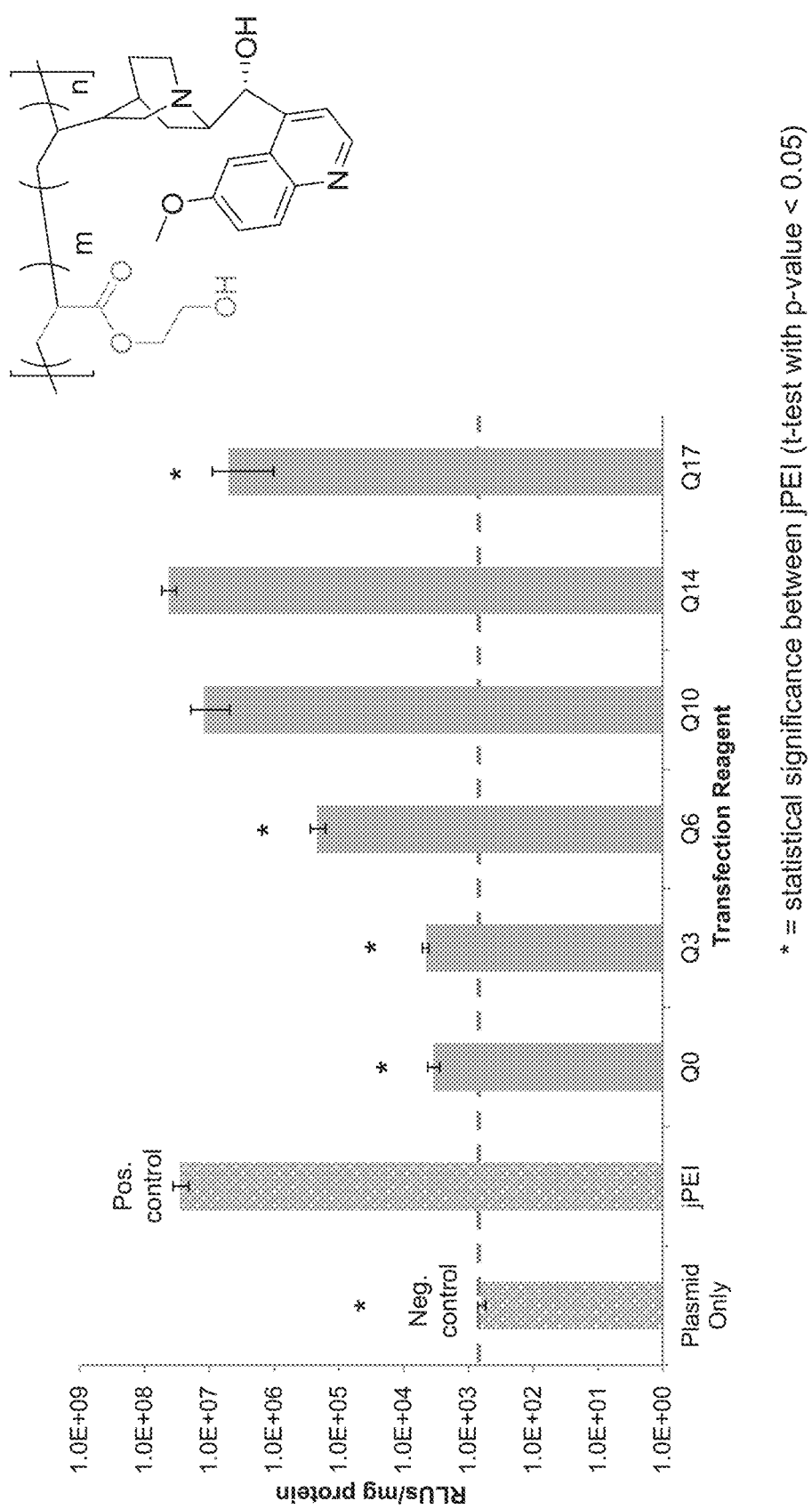

FIG. 39 shows luciferase transection of HeLa with HEA-Quinine copolymers ranging in percent quinine incorporation at N/P=10 for each sample.

Figure 40:
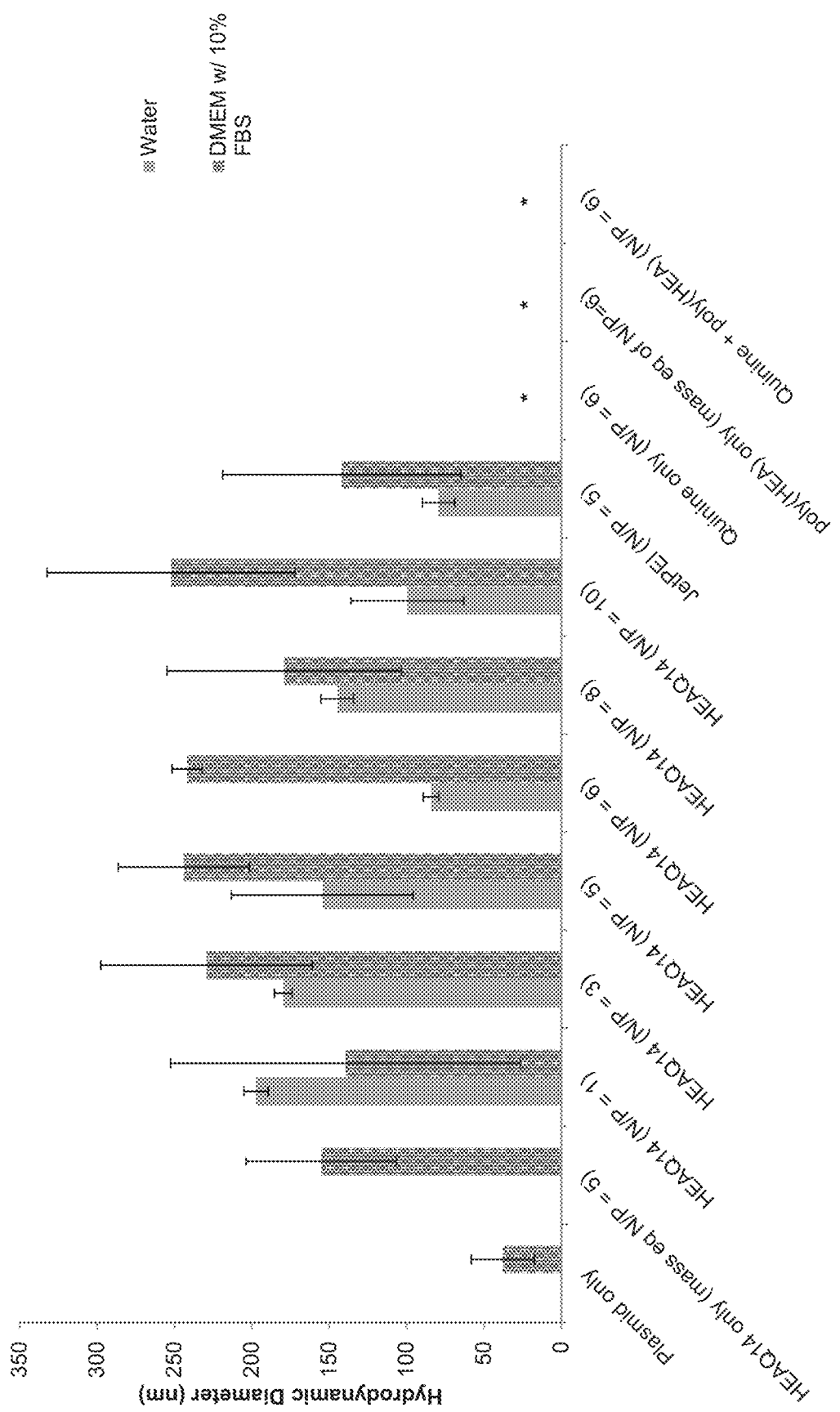

FIG. 40 shows hydrodynamic diameter of particles in aqueous media (pH~4) diluted with distilled water and DMEM (with 10% FBS) at 33 ng/uL (concentration at time of transfection) as measured by DLS. *=Inadequate signal due to lack of particle formation.

FIG. 41 shows aggregation Behavior of HEAQ14 polyplexes in Serum-Less Media.

Figure 42:
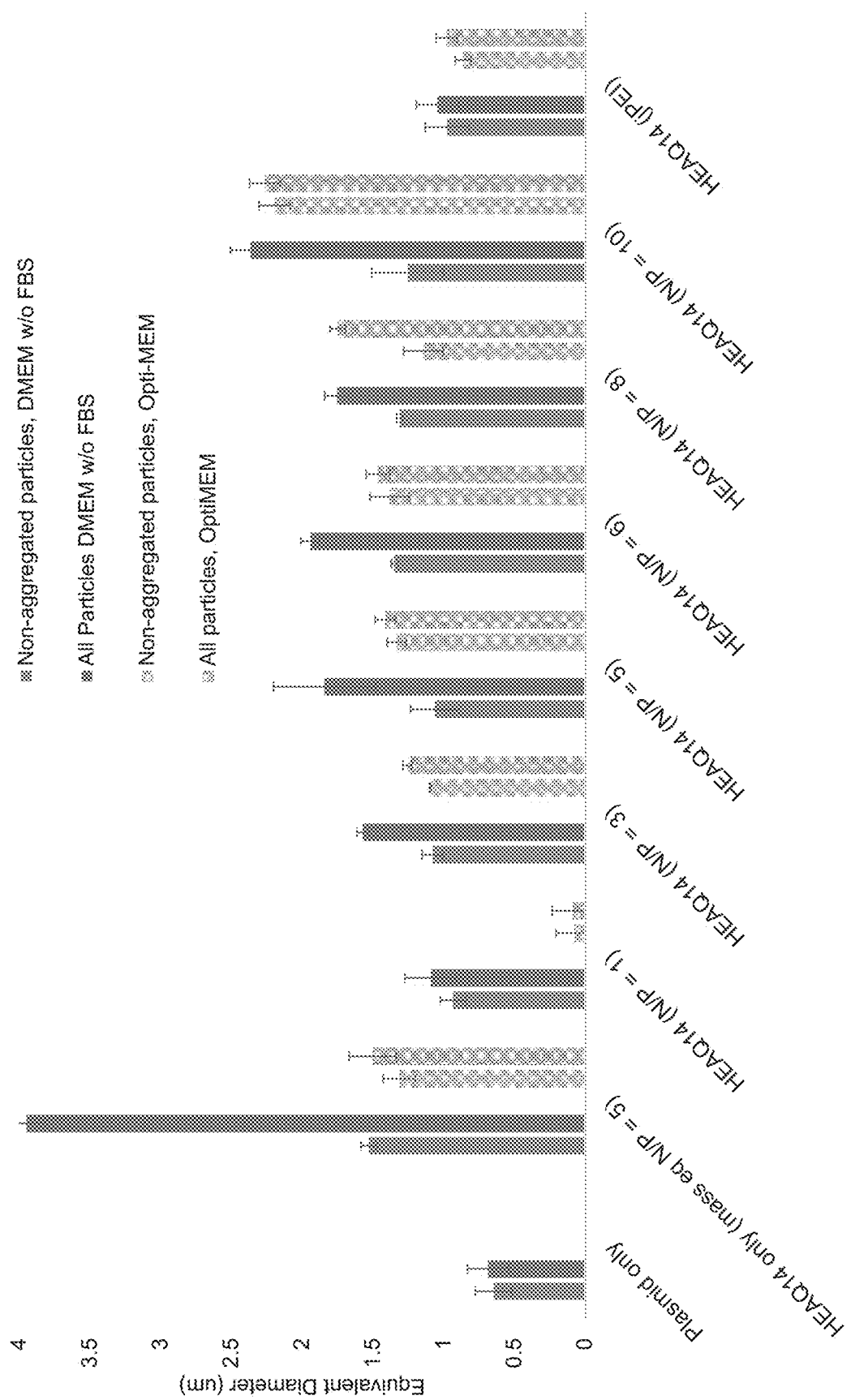

FIG. 42 shows the diameter of Particles Determined By Microscopy.

Figure 43:
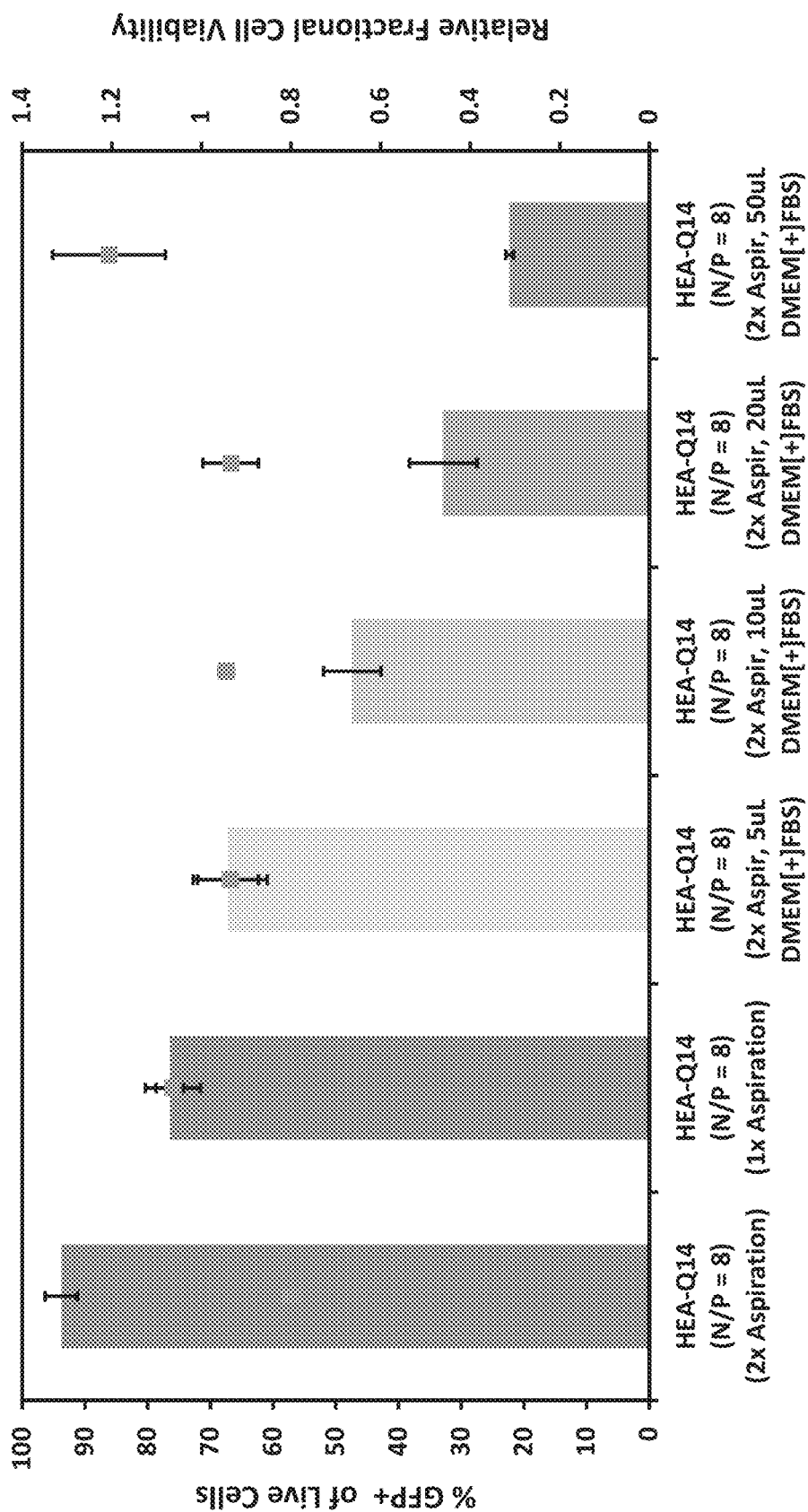

FIG. 43 shows the effect of Protein on Transfection Efficiency.

Figure 44:
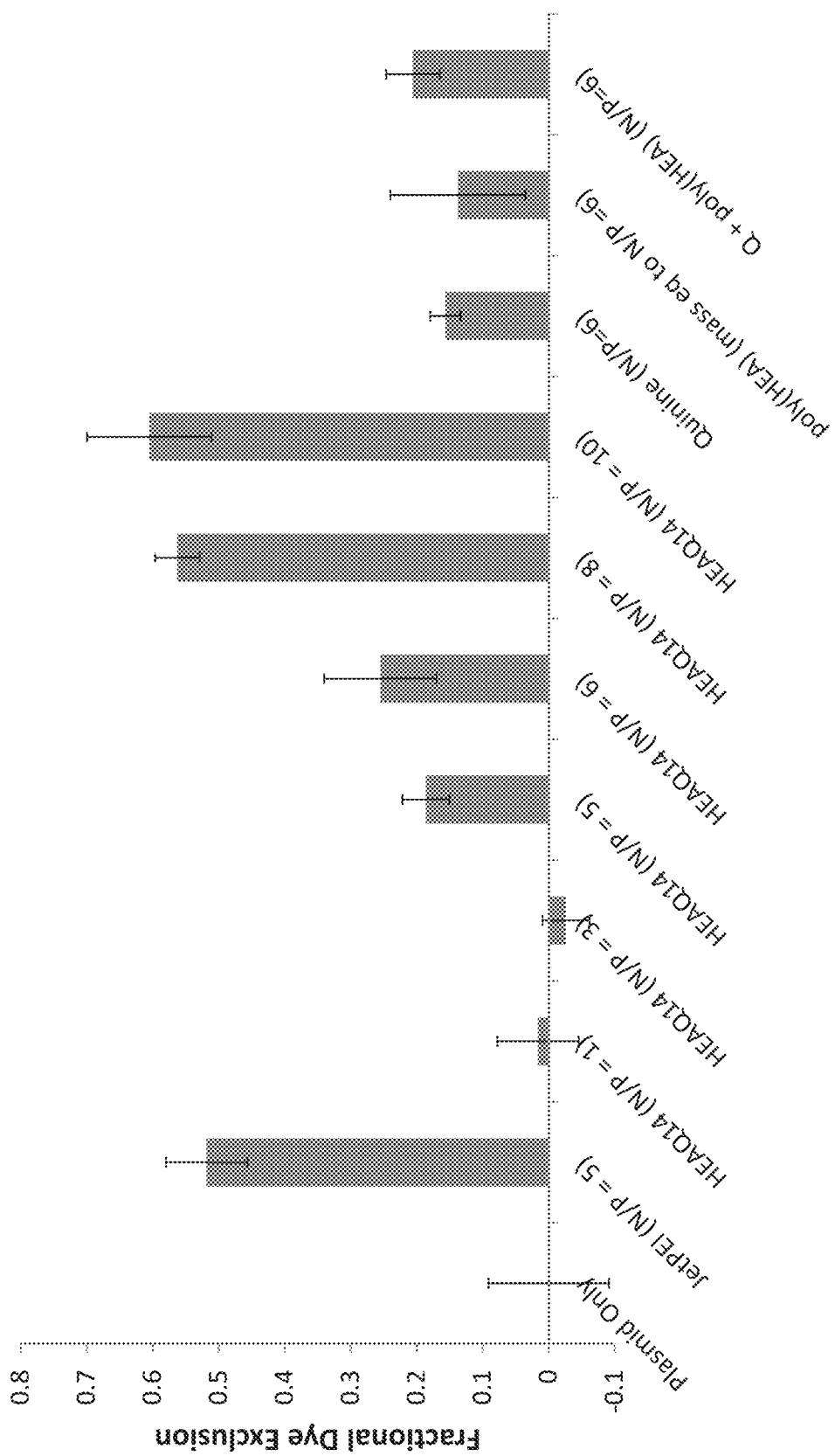

FIG. 44 shows a dye exclusion assay with plasmid DNA and ethidium bromide.

Figure 45:
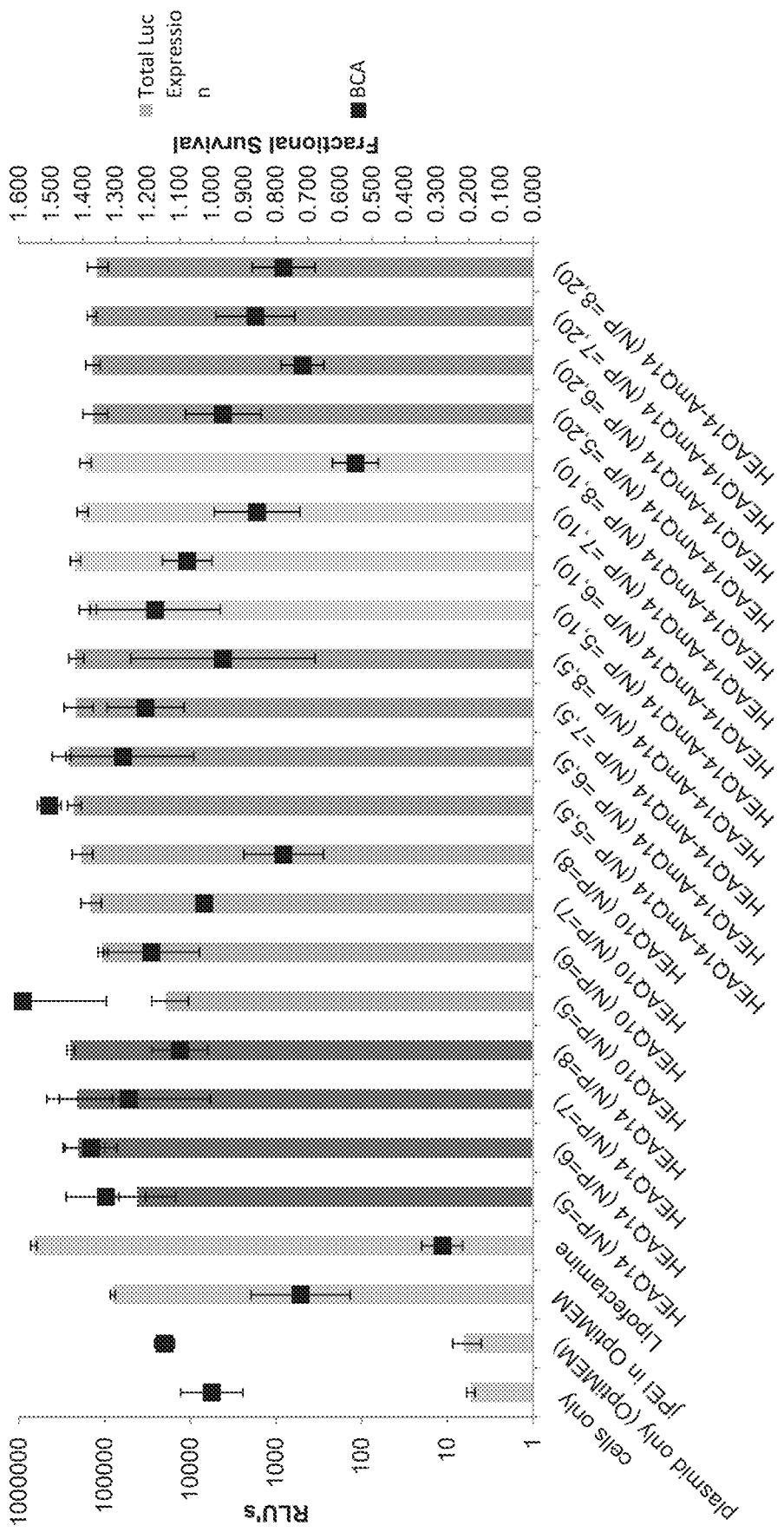

FIG. 45 shows luciferase transfection with HeLa cells.

Figure 46:
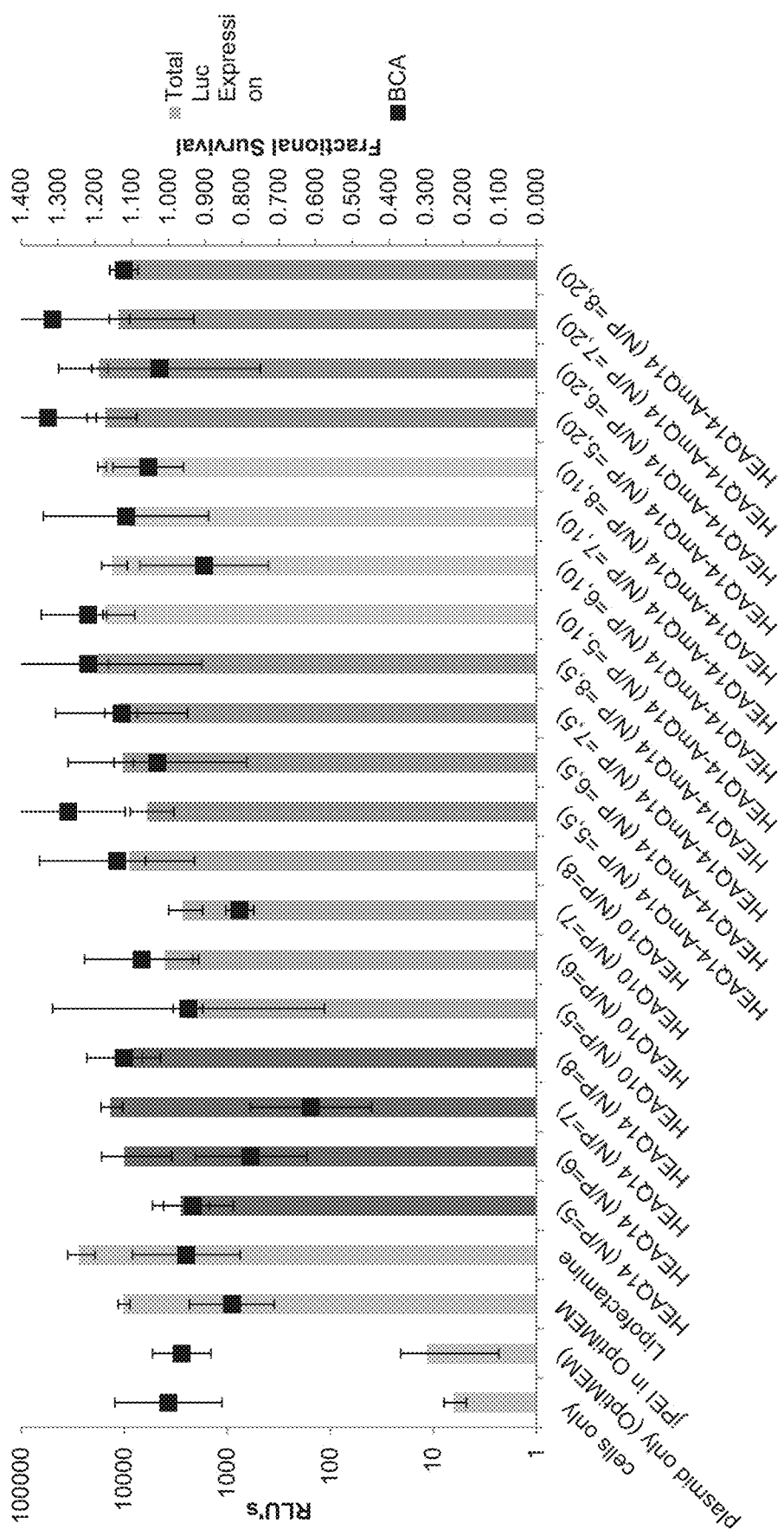

FIG. 46 shows luciferase transfection with HDFn (primary dermal fibroblasts).

Figure 47A:
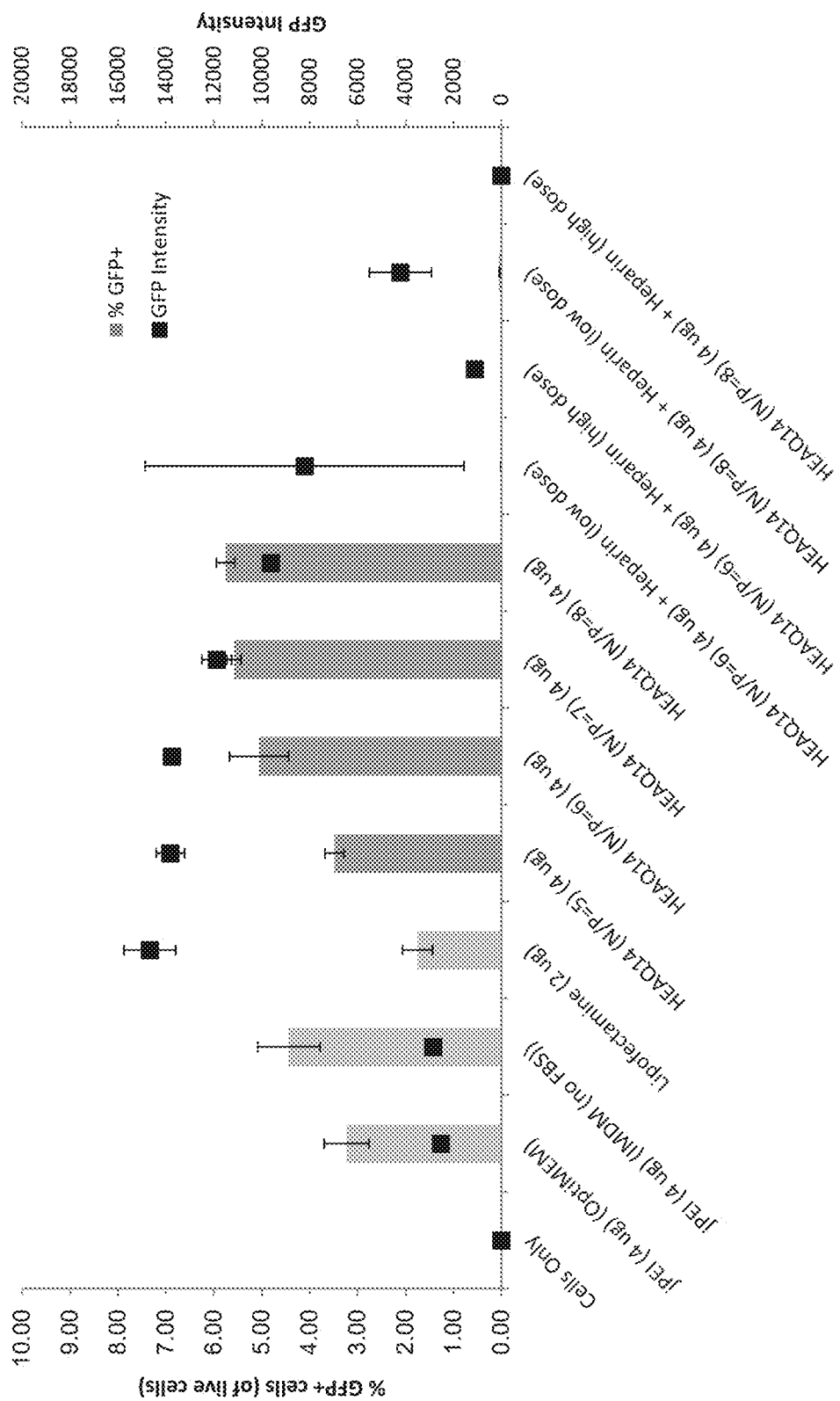
Figure 47B:
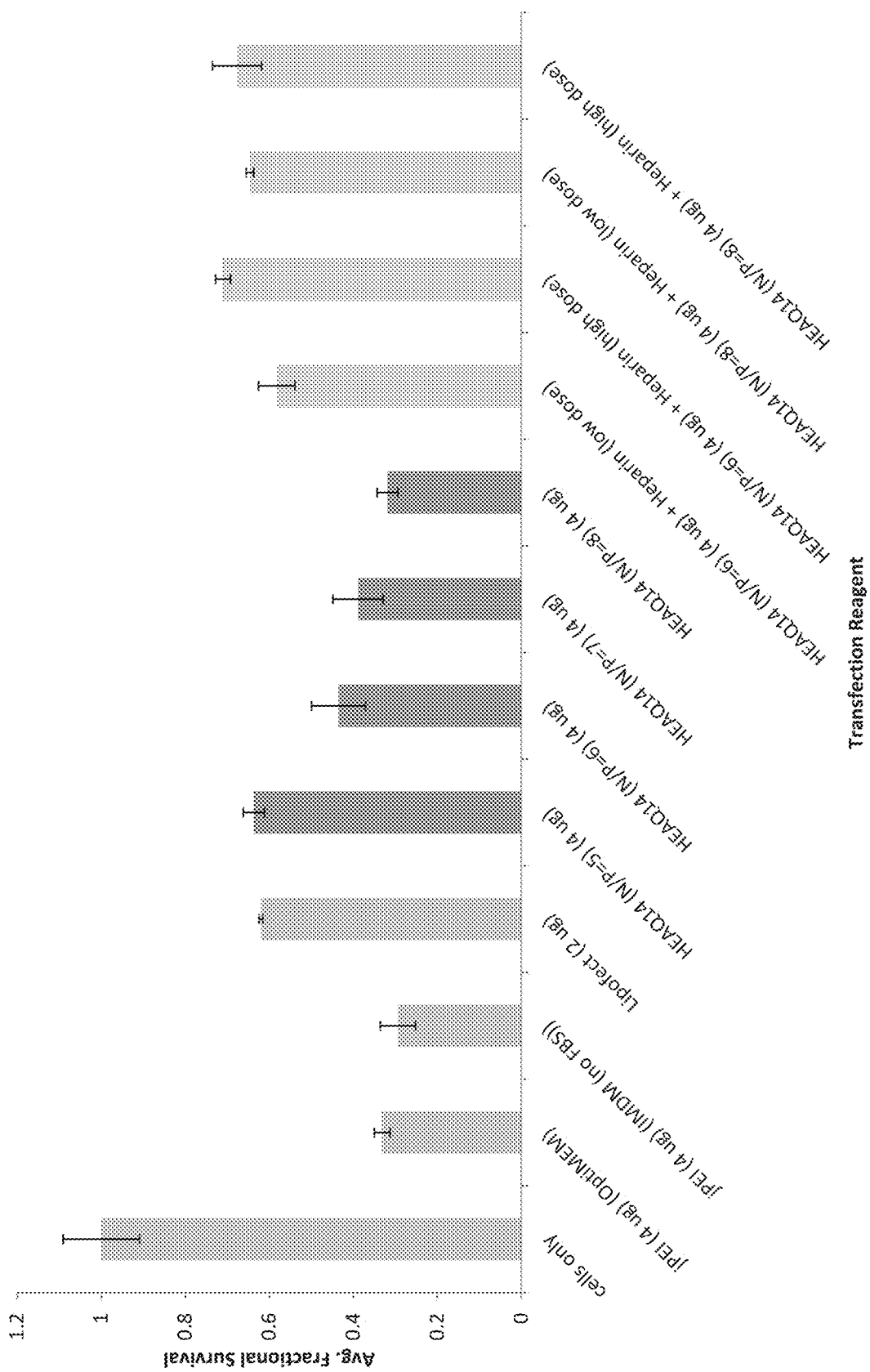

FIGS. 47a and 47b show transfection with K562 cells.

Figure 48:
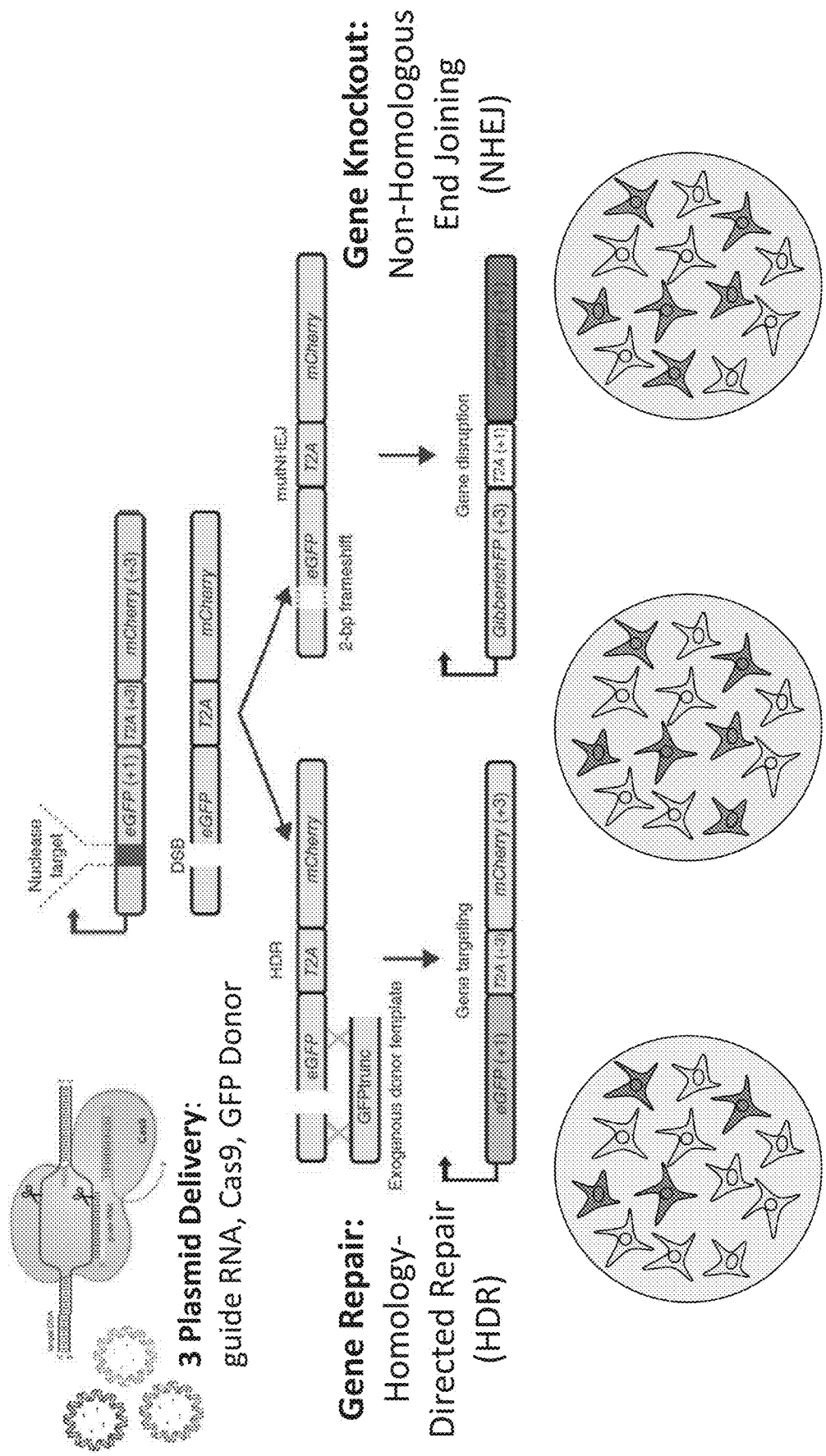

FIG. 48 shows CRISPR/Cas9 Traffic light reporter (TLR) Assay.

Figure 49:
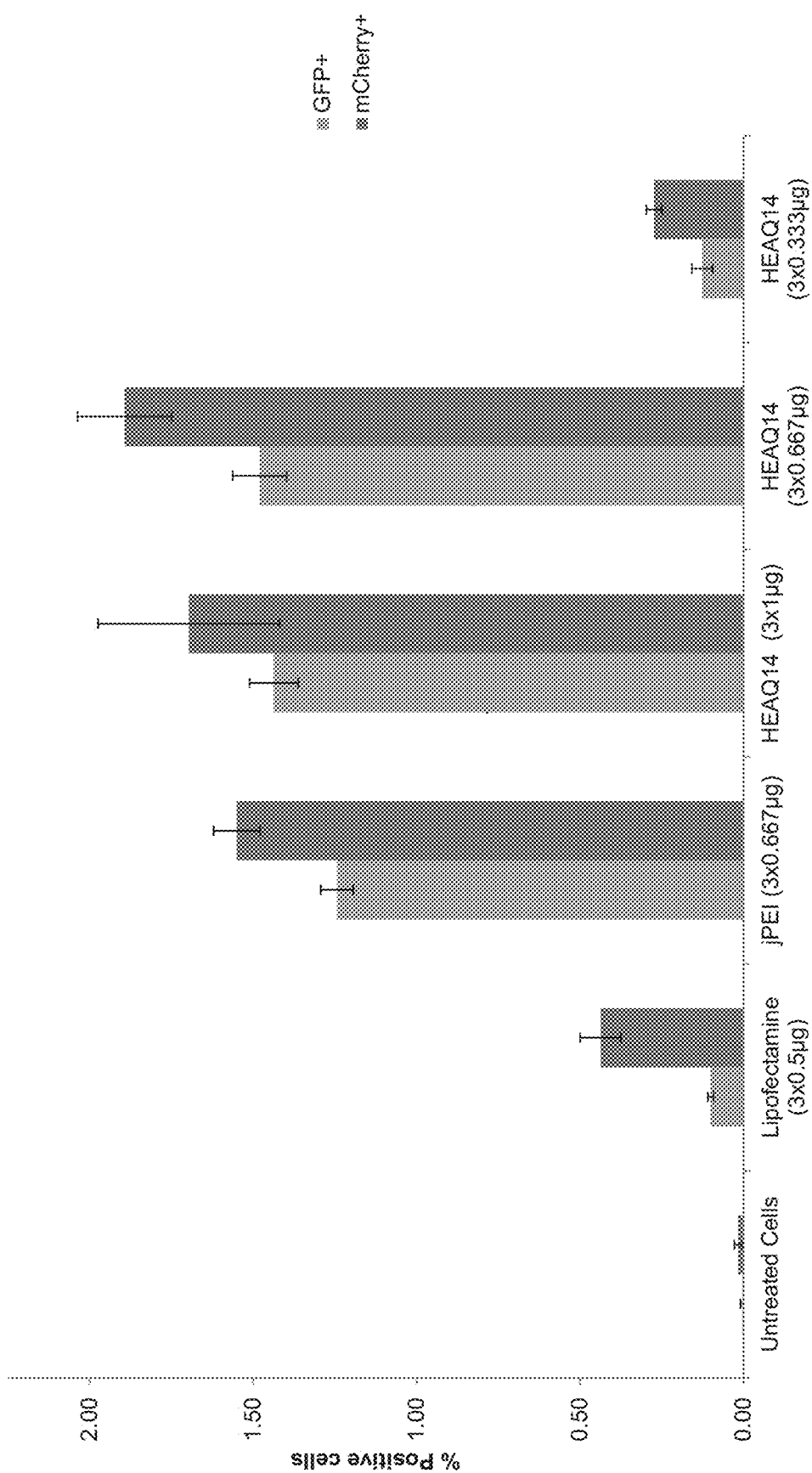

FIG. 49 shows dose Dependence of Plasmids for CRISPR/Cas9 Editing with HEK-293T Cells Modified with TLR Assay.

Figure 50:
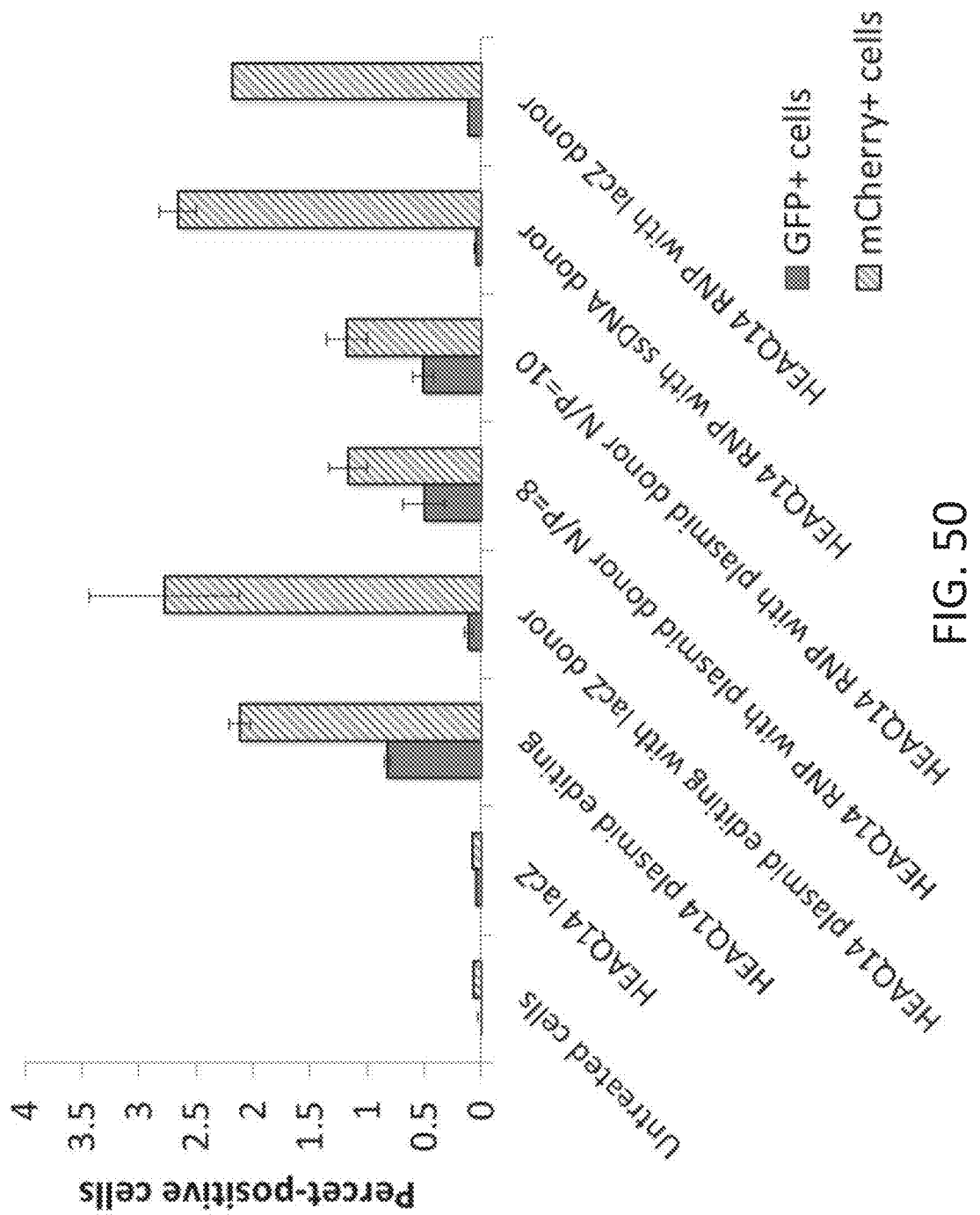

FIG. 50 shows gene Editing in HEK-293T TLR Cells via Cas9 RNP.

Figure 51:
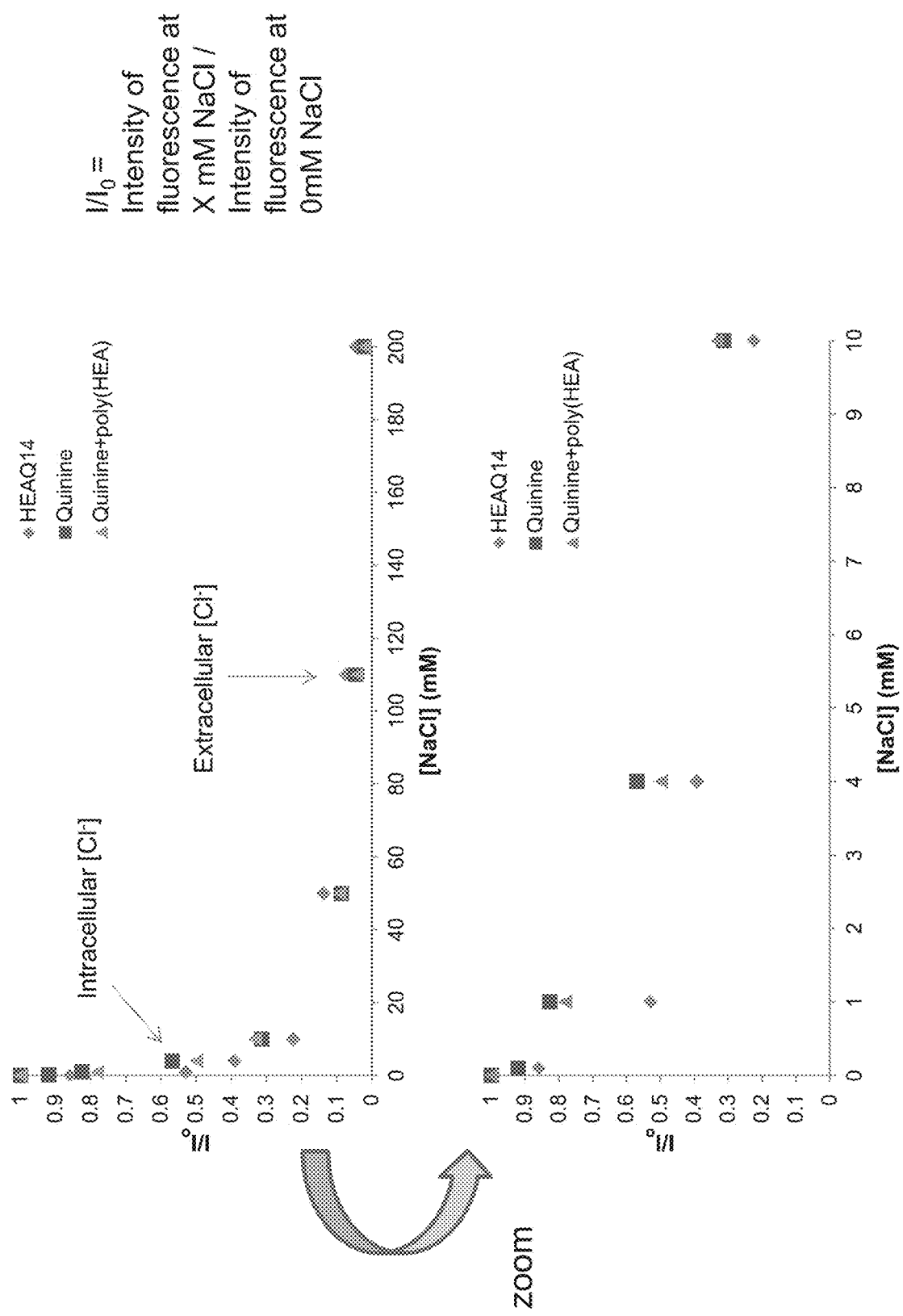

FIG. 51 shows a comparison of [Cl$^-$] Quenching of Quinine and HEAQ14.

Figure 52:
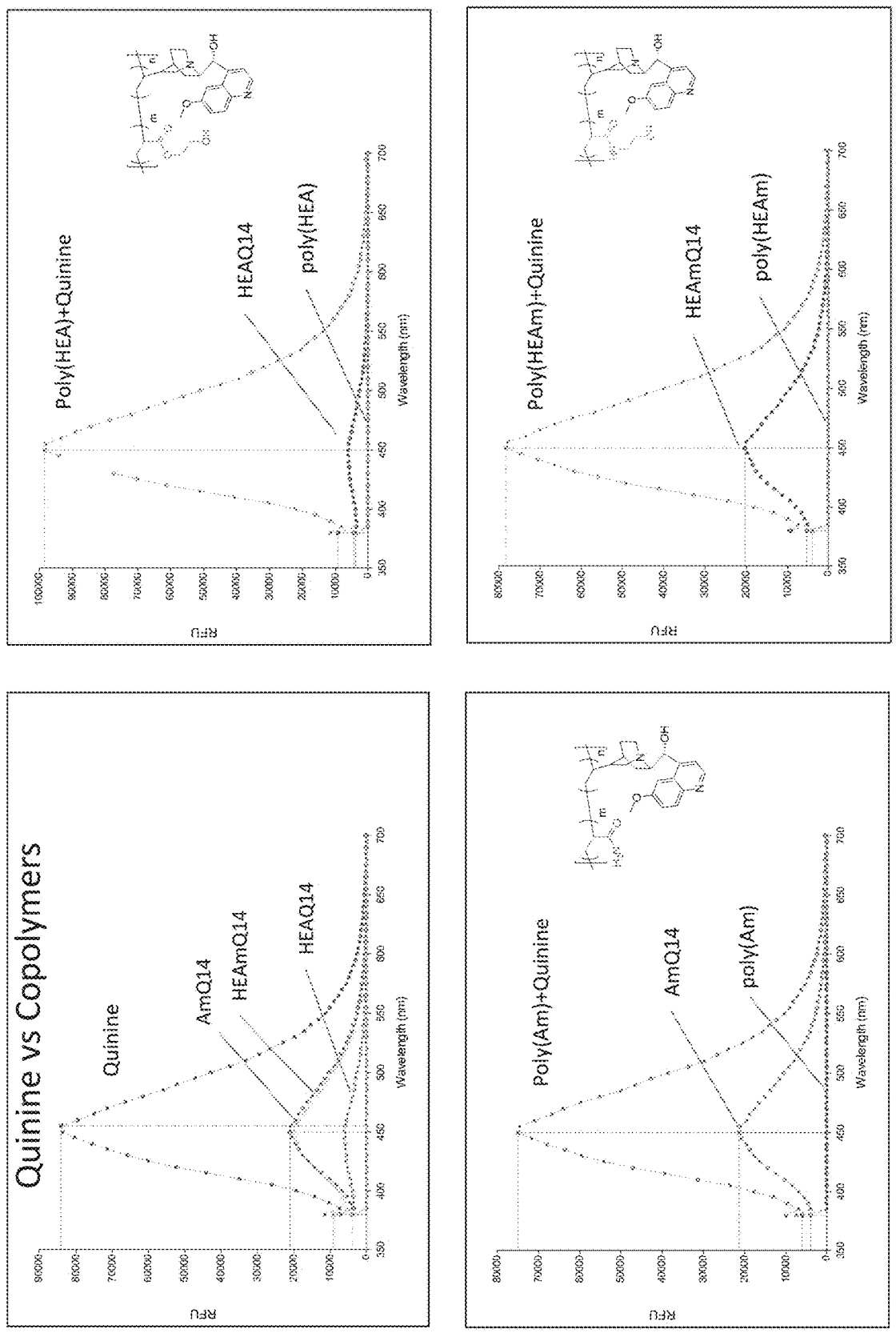

FIG. 52 shows Fluorescence of Quinine vs Quinine Copolymers.

FIGS. 53A through 53F show visual colocalization of Cy5-labelled DNA (yellow) with lysotracker (red) or HEAQ14 (blue). Images were taken using wide-field with deconvolution and cropped to fit cellular dimensions. Slices represent one portion of a 3D image stack. The leftmost image represents a composite overlay of each channel to the right. 53A) DNA and Lysotracker channels of HEK-293T cell transfected with HEAQ14 24 hrs prior to analysis. 53B) DNA and HEAQ14 channels of same sample as (53A). 53C) DNA and Lysotracker channels in a cell transfected with HEAQ14 4 hrs prior to analysis. 53D) DNA and HEAQ14 channels of cell transfected with HEAQ14 4 hrs prior. 53E) DNA and Lysotracker channels of a cell transfected with JetPEI 24 hrs prior. 53F) Negative control of a composite image of the HEAQ14, Lysotracker, and DNA. Scale bar represent 25 μm.

Figure 54:
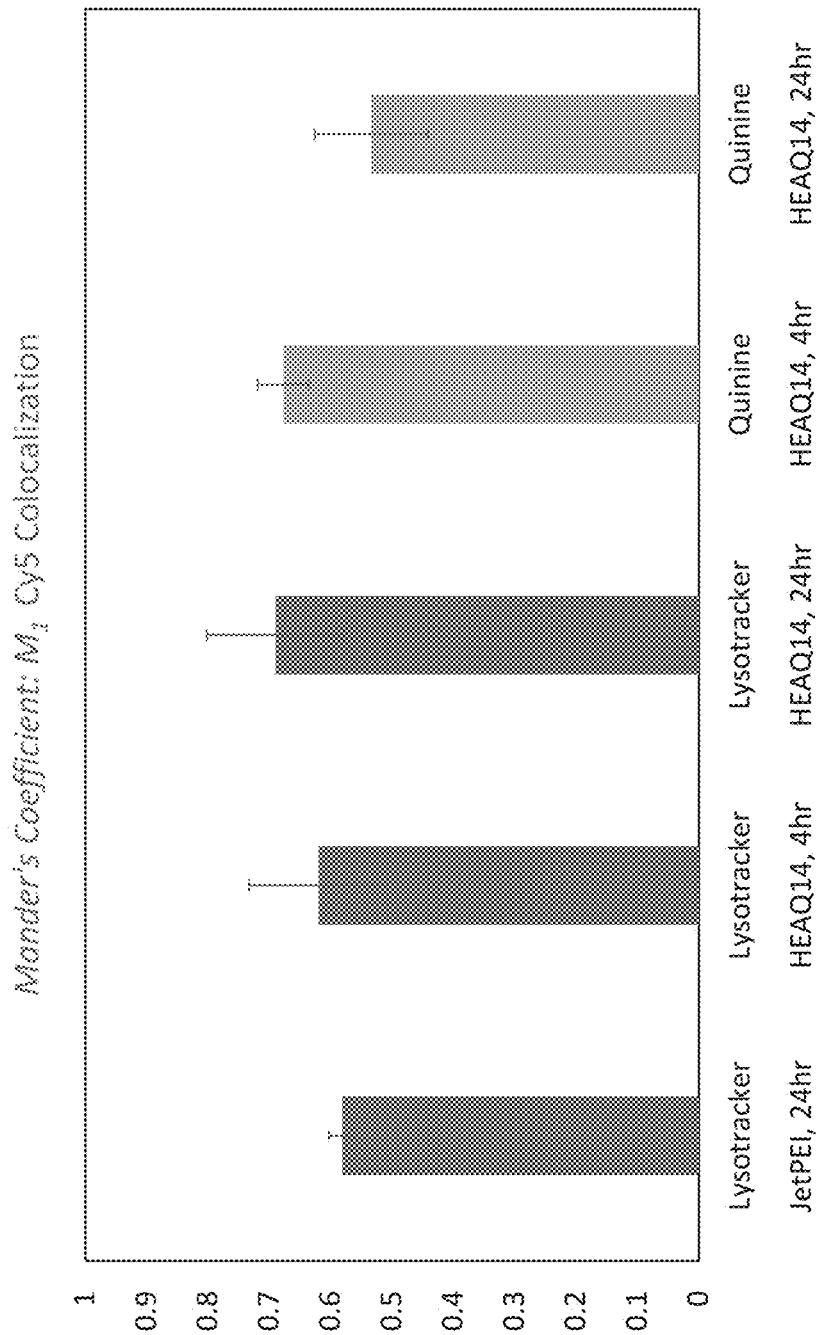

FIG. 54 shows colocalization analysis of three-dimensional images of cells dyed with Lysotracker Red and transfected with HEAQ14 and JetPEI containing Cy5-labelled plasmid encoding for GFP (ZsGreen) 4 and 24 hrs prior to analysis. Values represent Mander's Coefficient ($M_1$) for Cy5, representing the fraction of Cy-5 positive pixels overlapping with Lysotracker or HEAQ14 (designated here as quinine).

DETAILED DESCRIPTION OF ILLUSTRATIVE EMBODIMENTS

One skilled in the art will appreciate that the methods described herein can be practiced with embodiments other than those disclosed. The disclosed embodiments are presented for purposes of illustration and not limitation. One will also understand that components of the methods depicted and described with regard to the figures and embodiments herein may be interchangeable.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. For example, a conductive trace that "comprises" silver may be a conductive trace that "consists of" silver or that "consists essentially of" silver.

As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Use of "first," "second," etc. in the description above and the claims that follow is not intended to necessarily indicate that the enumerated number of objects are present. For example, a "second" substrate is merely intended to differentiate from another infusion device (such as a "first" substrate). Use of "first," "second," etc. in the description above and the claims that follow is also not necessarily intended to indicate that one comes earlier in time than the other.

New genome-engineering technologies, such as CRISPR/Cas9, are poised to make a tremendous impact in the treatment of genetic disorders. This technology is increasing the demand for new vehicles that can successfully deliver therapeutic nucleic acids, such as DNA, into cells with limited toxicity. One promising class of gene delivery vehicles is based upon cationic polymers which electrostatically bind negatively-charged DNA to form nano-scaled "polyplexes" that are internalized by cells via endocytosis. Although many polymer vehicles increase the internalization of DNA, effective delivery is often limited by polyplex entrapment in endosomes. Some anti-malarials, such as chloroquine, have been shown to improve DNA delivery by buffering acidic endosome vesicles which leads to endosomal rupture and polyplex escape into the cytoplasm. Quinine, a naturally-derived anti-malarial drug that is structurally similar to chloroquine and thought to have a similar effect on endosomes, contains a vinyl group that makes it amenable to polymerization. Quinine's vinyl group was successfully polymerized with a variety of comonomers, including acrylates, acrylamides, and methacrylates, through free radical polymerization. These quinine-integrated co-polymers can likely promote polymer-based DNA delivery into human cells and enhance endosomal escape. It has also been shown here that a variety of quinine-integrated polymers can electrostatically bind DNA and promote internalization in HeLa cells. In addition, owing to quinine's strong fluorescence at 450 nm, these quinine-integrated polyplexes have been tracked in vitro using fluorescence microscopy, making them powerful "theranostic" tools.

Recently, the field of genome engineering has taken a big step forward in providing clinical solutions to a whole host of diseases through the advent of nucleases (such as zinc finger nucleases, TALENs, and CRISPR-Cas9) that allow for specific and efficient editing of genes in cells in vitro and in vivo. Current methods being developed for this technology utilize engineered viruses for the delivery of the genetic cargo into the target cells. Viral vectors, however, have many severe limitations to their use in clinical applications. These limitations include difficulty/limitations in the scaling of production, clinical dangers such as immugenicity and mutagenicity, and very high cost (Glybera, the first western-approved gene therapy was sold for $1M/injection). Many nonviral methods, such as lipid-based, polymer-based, and peptide-based technologies have been developed to overcome the limitations of viral vectors. Many of these reagents are commercialized and commonly used for transfection in vitro including the cationic lipid-based reagent Lipofectamine and the cationic polymer (consisting of linear polyethylenimine) JetPEI. These reagents, however, show limited efficacy (i.e., limited gene expression and/or editing) in many difficult to transfect cell types. They also can be quite toxic to target cells which can be problematic for sensitive and/or valuable cell types for clinical applications.

There are several commonly used nonviral transfection agents used for research and limited clinical applications. JetPEI is a polymeric transfection, just like poly(HEA-co-quinine), that is positively charge at physiological pH. This allows the polymer to electrostatically bind to genetic cargo (such as plasmids) in a non-covalent fashion to form complexes commonly referred to as "polyplexes." The genetic cargo is compacted and stabilized against degradation while complexed with the polymer. The amount of polymer mixed with the genetic cargo can be tuned so that the complexes have a discrete average size (ranging anywhere from about 50 nm all the way to 1 um) and have an overall excess positive charge. These positively-charge complexes can electrostatically interact with the negatively-charged surface of the cell and allow for endocytosis of the complexes. The polyplexes are often trapped within endosomes (intracellular vesicles) that become acidified and merge with degradative lysosomes that further degrade the genetic cargo. It is, therefore, important for the reagent to help the cargo escape from this degradation pathway and release the genetic cargo into the cytoplasm so that the cargo can be trafficked to the nucleus of the cell where it will be expressed. JetPEI contains secondary amines that become increasingly protonated as the endosome becomes acidified. This buffering of the endosome leads to chloride ion influx that causes an increase in osmotic pressure that leads to endosome lysis and release of genetic cargo. Quinine and other antimalarials, such as chloroquine, are endosomolytic agents these compounds were incorporated into a biocompatible polymer chain in order to create a transfection reagent that is well tolerated by cells but also efficiently delivers cargo by enhanced endosomal escape. Quinine which is an inexpensive, FDA-approved, well-characterized, and naturally-sourced drug was the first target for incorporation into a polymer due to its ability to be copolymerized through its vinyl group. Quinine also has well-characterized fluorescent properties. This allows the polymer to be traceable via fluorescence without extra dyes. For example, cells that have been taken up by the polymer can be traced via fluorescence. This could potentially be useful for tracking the engraftment of stem cells that have been modified with this polymer. Also, since the fluorescence is sensitive to pH and chloride-ion concentrations, the polymer can be used as a probe for tracking intracellular conditions. Thus, incorporating quinine into functional biomaterials/biopolymers has potential to serve multiple functions such as a therapeutic agent, an agent that binds/compacts/delivers DNA and gene editing systems, and also a diagnostic/fluorescent tracking agent to observe/monitor delivery.

It has also been shown that poly(HEA-co-quinine) is both an effective delivery tool for transient gene expression in a variety of cells types, and can also deliver the genetic cargo and proteins necessary for gene editing in HEK-293 cells and achieve editing results with lower toxicity compared to commercial reagents such as JetPEI and Lipoctamine. Another benefit of this technology is the ease in which the polymer can be synthesized. It is a simple one-step synthesis with very inexpensive, readily-available starting materials and a simple purification step has also been developed. Thus, the quinine copolymers are easily scalable and tunable to achieve large quantities with controlled compositions at low cost.

Quinine and its Polymerization

The naturally-occurring alkaloid called quinine, isolated from the bark of several Cinchona tree species, is most well known as the additive that gives tonic water its bitter flavor. Some may not be aware, however, that the bittering agent in their beverage has been widely proclaimed as "the drug to have relieved more human suffering than any other in history." For over 300 years, quinine was the only known effective treatment of malaria, a mosquito-borne infectious disease that affects approximately 40 percent of the world's population and infects 400 million people annually. Although newer medications, such as artemisinin, are more widely used today in treating the disease, quinine is still an important second-line treatment in many areas of the world. The merits of quinine, however, do not stop with its anti-malarial properties. Each cinchona alkaloid, including quinine, cinchonidine and their naturally-occurring pseudoenantiomers, each contain five stereogenic centers (FIG. 1) and have proven themselves as invaluable tools for inducing chirality in areas such as asymmetric catalysis, racemic mixture separation, and chiral transition metal chemistry. Along with this pedigree, quinine is a highly fluorescent compound with excitation wavelengths of 250 and 350 nm and an emission max wavelength of 450 nm.

Owing to its bioactivity, chirality, and fluorescence, quinine has been utilized for a variety of applications. Several groups have incorporated quinine into a polymer in order to enhance its recoverability after use as a chiral catalyst (Kobayashi, N.; Iwai, K. Functional polymers. 1. Poly(cinchona alkaloid-co-acrylonitrile)s. New polymer catalysts for asymmetric synthesis. *J. Am. Chem. Soc.* 1978, 100 (22), 7071-7072 DOI: 10.1021/ja00490a053; Hermann, K.; Wynberg, H. Polymergebundene Cinchonaalkaloide als Katalysatoren in derMichael Reaktion. *Helv. Chim. Acta* 1977, 60 (7), 2208-2212 DOI: 10.1002/hlca.19770600713; Hodge, P.; Khoshdel, E.; Waterhouse, J. Michael reactions catalysed by polymer-supported quaternary ammonium salts derived from cinchona and ephedra alkaloids. *J. Chem. Soc. Perkin Trans.* 1 1983, 1 (399), 2205 DOI: 10.1039/p19830002205; Alvarez, R.; Hourdin, M. A.; Cave, C.; D'Angelo, J.; Chaminade, P. New polymer-supported catalysts derived from Cinchona alkaloids: Their use in the asymmetric Michael reaction. *Tetrahedron Lett.* 1999, 40 (39), 7091-7094 DOI: 10.1016/S0040-4039(99)01455-0; Moon Kim, B.; Sharpless, K. B. Heterogeneous catalytic asymmetric dihydroxylation: Use of a polymer-bound alkaloid. *Tetrahedron Lett.* 1990, 31 (21), 3003-3006 DOI: 10.1016/S0040-4039(00)89009-7; and Lee, J. H.; Yoo, M. S.; Jung, J. H.; Jew, S. sup; Park, H. geun; Jeong, B. S. Polymeric chiral phase-transfer catalysts derived from cinchona alkaloids for enantioselective synthesis of—amino acids. *Tetrahedron* 2007, 63 (33), 7906-7915 DOI: 10.1016/j.tet.2007.05.076). Most incorporation strategies, however, rely on functionalization of either the tertiary amine or secondary hydroxyl groups which can negatively affect the stereoselectivity of quinine as a catalyst. The first report of incorporating quinine into a polymer via its vinyl group was published by Kobayashi and Iwai in 1978. The researchers copolymerized quinine with acrylonitrile using free radical polymerization and used the polymer to achieve good enantiomeric excess in the asymmetric Michael reaction. Only a few other attempts have been made at connecting quinine to a polymer using its vinyl side chain (Kobayashi, N.; Iwai, K. Functional polymers. 1. Poly(cinchona alkaloid-co-acrylonitrile)s. New polymer catalysts for asymmetric synthesis. *J. Am. Chem. Soc.* 1978, 100 (22), 7071-7072 DOI: 10.1021/ja00490a053; Alvarez, R.; Hourdin, M. A.; Cave, C.; D'Angelo, J.; Chaminade, P. New polymer-supported catalysts derived from Cinchona alkaloids: Their use in the asymmetric Michael reaction. *Tetrahedron Lett.* 1999, 40 (39), 7091-7094 DOI: 10.1016/S0040-4039(99)01455-0; Moon Kim, B.; Sharpless, K. B. Heterogeneous catalytic asymmetric dihydroxylation: Use of a polymer-bound alkaloid. *Tetrahedron Lett.* 1990, 31 (21), 3003-3006 DOI: 10.1016/S0040-4039(00)89009-7; Klenin, S. I.; Strelina, I. A.; Troitskaya, A. V; Khripunov, A. K.; Urinov, E. U.; Lavrenko, P. N.; Bushin, S. V; Stockmayer, W.; Fufti, M.; Tsvetkov, V. N.; et al. Copolymerization of N-vinylpyrrolidone with quinine. 1988, 1977 (1), 43-49: and Rowan, S. J.; Sanders, J. K. M. Macrocycles derived from cinchona alkaloids: A thermodynamic vs kinetic study. *J. Org. Chem.* 1998, 63 (12), 1536). Despite this work, overall reactivity of quinine's vinyl side-chain in homo- and copolymerizations has not been well-characterized in the literature.

Potential Applications of Quinine Copolymers in Gene Therapy

Although work has been done to polymerize quinine for use in asymmetric synthesis, little work has been done to study quinine polymers for applications outside of this realm. Due to its antimalarial and fluorescent properties, polymers that incorporate quinine could be useful in a variety of biological applications including polymer-based nucleic acid delivery for gene therapy. Gene therapy is the treatment of a disease whereby a therapeutic nucleic acid, such deoxyribonucleic acid (DNA) or ribonucleic acid (RNA), are brought into the cells of a living organism in order to treat disease. The process of delivering the therapeutic nucleic acid into the cell is known as transfection. Recent advances in gene therapy promises to bring treatments for intractable diseases like muscular dystrophy, cystic fibrosis, Parkinson's disease, and several types of cancer, amongst others. Although the advent of cutting-edge gene editing technologies has brought gene therapy to the brink of clinical significance, the practice is limited by the deficiencies associated with the systems used for delivering the nucleic acids into the cells.

Engineered viruses are generally efficient in transfecting cells, but viral vectors pose many risks due to the possibility of recombination with endogenous viruses, oncogenic effects, and immunologic reactions. Alternative non-viral vectors, including cationic polymers, can be used to deliver DNA to cells by binding electrostatically to the DNA, and by doing so, creating a polyplex which stabilizes the DNA against degradation and promotes its uptake into cells (FIG. 2) (Mintzer, M. a; Simanek, E. E. Nonviral Vectors for Gene Delivery. *Chem. Rev.* 2008, 109 (2), 259-302 DOI: 10.1021/cr800409e). Transfection by polymeric vehicles have the advantage of improved biocompatibility, stability, and increased load capacity, but polymeric vehicles are often hampered by poor transfection efficiency. There has been a tremendous push to develop polymers that provide increased transfection efficiency while limiting toxicity.

One common method of improving transfection efficiency of a polymer is to administer a dose of the antimalarial, and cinchona alkaloid, chloroquine (Pack, D. W.; Hoffman, A. S.; Pun, S.; Stayton, P. S. Design and development of polymers for gene delivery. *Nat. Rev. Drug Discov.* 2005, 4 (7), 581-593 DOI: 10.1038/nrd1775). Chloroquine, which has a chemical structure similar to quinine, promotes transfection by lysing the endosome vesicles that entrap the polyplexes upon endocytosis into the cell. This lysosomal buffering property is thought to be a shared mechanistic underpinning to the quinoline-containing antimalarials such as chloroquine and quinine.

Figure 2:
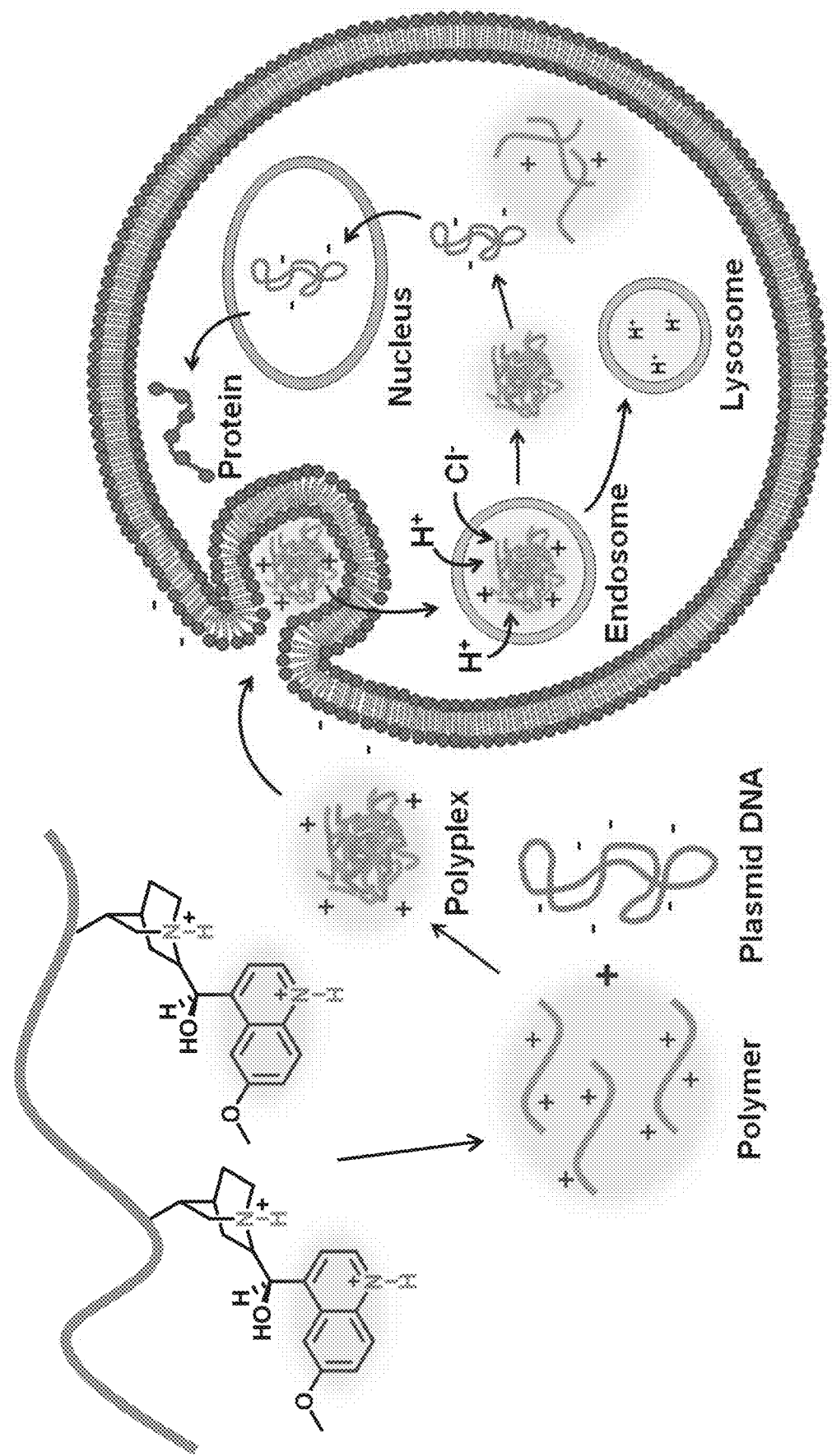
FIG. 2 is a schematic representation of the use of a quinine-containing polymer as polymeric transfection reagent for the enhanced delivery of plasmid DNA due to its potential endosomal escape properties, unique packaging and release of DNA cargo, and visualization of the polymer via quinine's blue fluorescence (Ex: 350 nm, Em: 450 nm).

Disclosed herein is the idea of incorporating quinine into a polymeric transfection agent via its vinyl group to improve the endosomal escape properties of the polymer and lead to increased transfection efficiencies (FIG. 2). Along with using standard methods to gauge transfection efficiency, due to quinine's fluorescent properties, the quinine co-polymer's mode of action can be critically analyzed using fluorescence microscopy. Quinine itself will provide therapeutic benefits while allowing for diagnostic monitoring of transfection progress and mechanism. In this, sense quinine-based polymers have the potential to be useful "theranostic" tools in the field of gene delivery.

Quinine's reactivity in free-radical copolymerization with a variety of monomers was explored and characterized. The use of quinine copolymers in nucleic acid delivery for potential applications in gene therapy was also characterized. Quinine and other cinchona alkaloid compounds were successfully copolymerized in a predictive manner with a variety of useful monomers via free-radical polymerization and copolymers have been developed that allow for the improved transfection of clinically-useful human cell lines.

Synthesis and characterization of quinine copolymers: The reactivity of quinine in free-radical copolymerization with olefin-containing monomers was assessed. The reactivity ratios of the comonomer pairs was obtained via nuclear magnetic resonance (NMR) analysis. Characterization of the polymer's size and composition was carried out using size exclusion chromatography (SEC), NMR, and ultraviolet-visible (UV-Vis) spectroscopy. Incorporation of quinine copolymers into multiblock copolymer architectures was carried out using controlled polymerization techniques.

Transfection studies with quinine copolymers: DNA-binding properties and polyplex characterization for select quinine copolymers was done using gel electrophoresis and dynamic light scattering (DLS). Uptake and transfection studies, including cyanine (Cy5) uptake, luciferase and green fluorescent protein (GFP) assays, was carried out with quinine-copolymers in human uterine cervical carcinoma (HeLa) cell line. These studies were done to determine which polymers were suitable transfection vectors and to carry out the transfection procedure with these reagents. Confocal fluorescence microscopy was used to analyze any intracellular barriers to transfection that may guide quinine-copolymer modification. After the quinine-copolymer transfection reagent, transfections were carried out in medically-important primary cell lines, such as induced pluripotent stem cells (IPSCs) which are used in the treatment of the disease epidermolysis bullosa (EB).

Free-Radical Polymerization of Allylic Olefins

One of the most widespread methods for the production of industrially important polymers is through free-radical polymerization. Free-radical polymerization is a type of chain-growth polymerization where radicals within a reaction mixture sequentially add monomers via the formation of covalent bonds to form polymer chains. The first step in this process is called initiation whereby free radicals are generated by the decomposition of an initiator molecule and react with monomers, as shown by 2,2'-azobis(2-methylpropionitrile) (AIBN) and styrene in FIG. 3a, to start growing polymer chains. The initiator-monomer radical adduct can then sequentially add more monomers to grow a chain in a process called propagation (FIG. 3b). At some point, however, the propagating radical reacts in a way that causes it to lose its ability to further add monomer and the growing polymer chain has terminated. Generally, this occurs by the reaction of two propagating radicals such as through combination or disproportionation (as shown in FIG. 3c). Although there are many alternative reactions that may occur to complicate this process, these steps constitute the basic free-radical polymerization mechanism.

Despite the widespread use of free radical polymerization for the production of industrially useful polymers, some useful polymers cannot be produced using radical polymerization techniques. Alpha olefins and 1,1-dialkyl olefins, which includes industrially useful polymers such as propylene and isobutylene, due not readily homopolymerize to make long polymers via free radical polymerization. The free-radical homopolymerization of these monomers typically give low-molecular weight amorphous polymers and can only be synthesized by free-radical polymerization at extremely high temperatures and pressures. This is due to facile chain transfer to monomer in a process called degradative chain transfer. Alpha-olefins have an allylic proton that can be easily abstracted by the radical of propagating chain (denoted by P$^\bullet$) to yield a stabilized allylic radical (FIG. 4a).

Transfer of the radical from a propagating chain to a monomer, initiator, solvent, or another reagent is called chain transfer. The more chain transfer that occurs during a polymerization, the more the average polymer chain length, also known as the degree of polymerization (N), will be reduced. After chain transfer, if the newly formed radical is still reactive enough, it can continue to add monomer and form a new polymer chain. In the case with α-olefins, however, once the radical has been transferred to the monomer via proton abstraction, the stabilized allylic radical is not reactive enough to add another monomer and start a new chain. Through this transfer to monomer, the polymerization ceases. To describe this process in terms of kinetics, if $k_{tr}$, $k_p$, and $k_a$ are the relative rate constants for the transfer, propagation, and reinitiation, respectively, than degradative chain transfer occurs when the transfer rate is much larger than propagation ($k_{tr} \gg k_p$) and reinitiation is slow compared to propagation ($k_a < k_p$). The overall effect of this situation is a large decrease in the rate of polymerization $R_p$ and a large decrease in the degree of polymerization N. Therefore degradative chain transfer results in slow formation of very small polymers (N≈1-5 units in length).

In order to gauge the reactivity of the quinine vinyl group towards free-radical polymerization, it could be compared to the reactivity of a simple monomer with similar structure at the center of reactivity. It is thought that quinine should exhibit similar reactivity to 3-methyl-1-butene due to its similarity in structure (FIG. 4b). Both monomers have a tertiary γ carbon with one proton. Free-radical polymerization of either monomer would likely lead degradative chain transfer where abstraction of this γ proton would leave stabilized allylic radicals. Although degradative chain transfer has not been explicitly implicated for 3-methyl-1-butene in the literature, this monomer has not been reported to undergo free-radical polymerization and has only shown to polymerize via metallocene catalysts, similar to other α-olefins, or through cationic isomerization polymerization. In addition, quinine is a bulkier monomer which may cause steric hindrance and limit homopolymerization of this monomer. This evidence leads one to believe that quinine is not amenable to facile free-radical homopolymerization.

Copolymerization of Quinine

Although quinine may not readily undergo free-radical homopolymerization, quinine's vinyl group has been successfully copolymerized via free-radical polymerization under mild conditions with monomers such as acrylonitrile (Kobayashi, N.; Iwai, K. Functional polymers. 1. Poly (cinchona alkaloid-co-acrylonitrile)s. New polymer catalysts for asymmetric synthesis. *J. Am. Chem. Soc.* 1978, 100 (22), 7071-7072 DOI: 10.1021/ja00490a053) and N-vinylpyrrolidone (Klenin, S. I.; Strelina, I. A.; Troitskaya, A. V; Khripunov, A. K.; Urinov, E. U.; Lavrenko, P. N.; Bushin, S. V; Stockmayer, W.; Fufti, M.; Tsvetkov, V. N.; et al. Copolymerization of N-vinylpyrrolidone with quinine. 1988, 1977 (1), 43-49). In 1978, Kobayashi et al. found that when quinine was mixed with acrylonitrile (30 mmol) at a 1:4 ratio in chloroform (10 mL) and refluxed with 0.048 eq. AIBN (0.24 mmol) for two days, a precipitated polymer precipitated that was roughly 12% quinine. The homopolymerization of quinine was also attempted, but no polymerization took place.

A common method for characterizing the reactivity of a monomer in a copolymerization is by using reactivity ratios. In the copolymerization of monomers $M_1$ and $M_2$, the reactivity ratios $r_1$ and $r_2$ are defined as $$r_1 = k_{11}/k_{12} \tag{2-1}$$

$$r_2 = k_{22}/k_{21} \tag{2-2}$$

where $k_{11}$ is the rate constant for P-$M_1^\bullet$ (propagating chain with a terminal $M_1$ radical) adding to another $M_1$ while $k_{12}$ is the rate constant for P-$M_1^\bullet$ adding to $M_2$. Similarly, $k_{22}$ is the self-propagation rate constant of P-$M_2^\bullet$ while $k_2$ is the cross-propagation rate constant of P-$M_2^\bullet$. Thus, if $r_1 > 1$, P-$M_1$ has a preference for adding $M_1$ over $M_2$ and if $r_1 < 1$, P-$M_1$ has a preference for adding $M_2$ over $M_1$. By using reactivity ratios, the polymer composition and monomer sequence can be described. As $r_1 \to 0$ and $r_2 \to 0$, the polymer tends towards an alternating sequence. When $r_1 r_2 > 1$, the copolymer resembles a block copolymer where the polymer chain consists of homopolymer sections. When $r_1 r_2 \to 1$, the copolymerization is considered an ideal copolymerization and each monomer has the same preference for adding one or the other of the two monomers. This copolymerization leads to a statistical copolymer where the less reactive monomer will be present at a lower percentage but be interspersed evenly throughout the polymer.

In the only report to have determined quinine's reactivity ratio in the copolymerization with another monomer, Borchan et al. determined the reactivity ratios for the copolymerization of quinine with N-vinylpyrrolidone (VP) (Klenin, S. I.; Strelina, I. A.; Troitskaya, A. V; Khripunov, A. K.; Urinov, E. U.; Lavrenko, P. N.; Bushin, S. V; Stockmayer, W.; Fufti, M.; Tsvetkov, V. N.; et al. Copolymerization of N-vinylpyrrolidone with quinine. 1988, 1977 (1), 43-49). Borchan et al. determined the reactivity ratios using several different models including the Mayo-Lewis copolymerization model. One form of the Mayo-Lewis equation which can be written as $$F_1 = \frac{r_1 f_1^2 + f_1 f_2}{r_1 f_1^2 + 2 f_1 f_2 + r_2 f_2^2} \quad (2\text{-}3)$$

equates the mole fraction of $M_1$ in the copolymer, $F_1$, with the reactivity ratios $r_1$ and $r_2$ and the mole fraction of the monomers in the feed stock, denoted by $f_1$ and $f_2$ for monomers $M_1$ and $M_2$ respectively. By measuring the resulting comonomer ratio, $F_1$, in the polymer at low conversion for several monomer feed ratios and fitting the data with Eq. 2-3, one can solve for the reactivity ratios $r_1$ and $r_2$. Borchan et al. found that $r_1$ (VP)=2.60 and $r_2$ (quinine)=0.38. The product $r_1 \cdot r_2 = 0.988$ is close to 1, so the copolymerization nearly ideal and a relatively low percentage of quinine is interdispersed evenly throughout the polymer.

Polymer-Based Solutions for Overcoming Barriers in Gene Delivery

As stated previously, quinine copolymers are of interest due to their potential use as polymeric gene delivery agents. Research in the field of polymer-based gene delivery really gained momentum in the early 1990's when polymers were seen as a promising alternative to viral-based and liposome-based vectors. One of the first polymers recognized for its potential in gene delivery was poly-L-lysine (PLL) (FIG. 5a).

As in the case for PLL, most polymers used for nucleic acid delivery contain amine groups that can be protonated at physiological pH. Since nucleic acids such as DNA contain negatively charged phosphate groups on their backbone, a positively-charged polymer, such as PLL, will bind the DNA through electrostatic interactions. The DNA-polymer complex, which is known as a polyplex, is compact and can have a diameter of 100 nm or less which is generally considered the size necessary to be efficiently endocytosed into the cell. Once bound to the polymer, the DNA is protected from degradation by nucleases and can be stable for hours at a time. For in vivo applications, the polyplex must remain stable in circulation and be resistant to aggregation in blood in order to successfully be endocytosed into the cell. Aggregation can also lead to clots in the capillaries of the lung that can be rapidly fatal. Having an excess positive charge can help limit aggregation but can also cause the adsorption of serum proteins that can also reduce endocytosis and increase the excretion of the particles. These are just several design considerations for a polyplex for simply reaching a target cell in a living organism.

Upon reaching the cell, a positively-charged polyplex binds electrostatically to the negatively-charged proteoglycans coating the cell's surface. The polyplex can then be endocytosed either through clathrin-dependent, caveaolae, or micropinocytosis pathways. Success of the transfection for a particular cell-type can depend on the method of endocytosis. Once within the cell, the polyplex is trapped in a vesicle called an endosome which is trafficked to the lysosome for degradation. Thus, the polyplex must be released from the endosome in order to escape degradation. One particular polymer called polyethylenimine (PEI) (FIG. 5b), which has been widely used since its first use in gene delivery by Behr et al. in 1995, achieves good transfection efficiency partly due to its ability to break out of endosome entrapment. This ability has been largely attributed to its ability to buffer against the degradative acidification of endosomes. This theory of endosomal escape has been coined the "proton-sponge" theory.

Degradation of the endosome cargo while en route to the lysosomes occurs by translocation of protons from the cytosol to the endosome interior through an transmembrane protein called an ATPase proton pump. The active transport of protons decreases the endosome pH from the extracellular pH of 7.4 to an acidic pH of 5.0-6.5. Polymers such as PEI, which have protonatable secondary and tertiary amines that have pKas similar to the pH of endosomes, are hypothesized to act as "proton sponges" by absorbing the protons through protonation of their amine groups. PEI has a high cationic-charge potential due to the fact that every third atom in the polymer is a protonatable nitrogen that can participate in the buffering process. When moving from neutral extracellular space to the acidic lysosomes, the percentage of protonated amines increases from 15-45%. As protons are absorbed by the amine-containing polymer, the ATPase pump continues to pump protons in order to decrease the pH. The excessive proton pumping increases the passive diffusion of chloride ions which causes an increase in the ion concentration of the vesicle. As the ion concentration increases, the osmotic pressure within the vesicles increases and the influx of water swells the endosome and leads to its rupture (FIG. 6). This pH buffering also inhibits the activity of the lysosomal nuclease which protects the DNA from degradation. It should be noted that several studies that have examined the effect on amine-containing polymers by monitoring endosomal $Cl^-$ concentration and pH and their conclusions support the "proton sponge" hypothesis. Other studies, however, have found contrary evidence. This has caused the "proton sponge" theory of endosomal escape to be somewhat controversial, but it still a prevalent theory used to explain the mechanism in which polymers escape endosomal entrapment.

Once having escaped from the endosome, the polymer must be able to unpack its nucleic acid cargo and be shuttled to the correct location. In the case of RNA, expression of RNA will occur directly in the cytoplasm, but for DNA, the DNA must be trafficked through the pores of the nucleus where it can then be expressed. Only after overcoming all of these extracellular and intracellular barriers will a polymer be considered a successful transfection vector. PEI was a major milestone in polymer-based gene delivery because it was one of the first polymers to overcome all of the barriers necessary to achieve significant levels of gene expression.

Current Efforts to Make Polymeric Vectors More Biocompatible

Figure 7:
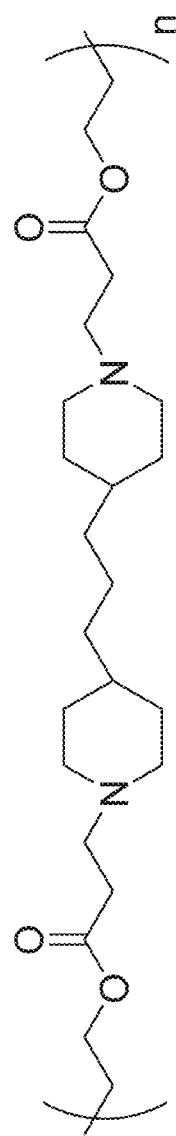
FIG. 7 shows one type of Poly(β-amino ester) (PBAE).

Despite being considered the gold standard in polymer-based gene delivery, PEI is still considered too toxic for most in vivo applications and is too toxic for many cell types in vitro. This has led researchers to develop polymers that can achieve efficient gene delivery and still maintain biocompatibility. One method for increasing the biocompatibility of polymer vectors is by increasing degradability of the polymer. Poly(β-amino esters) (PBAE) are a class of cationic polymers that were first developed by the Langer group in the year 2000. They contain tertiary amines that can be protonated like PEI, but they also contain biodegradable ester linkages that can be hydrolyzed and limit the polymer's cytotoxicity (FIG. 7) (Gaj, T.; Gersbach, C. A.; Barbas, C. F. ZFN, TALEN, and CRISPR/Cas-based methods for genome engineering. *Trends Biotechnol.* 2013, 31 (7), 397-405 DOI: 10.1016/j.tibtech.2013.04.004).

Figure 8:
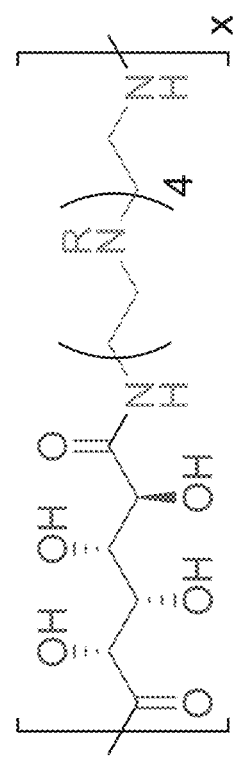
FIG. 8 shows poly(glycoamidoamine) (PGAA) called poly(D-glucaramidopentaethylenetetramine).

Another method commonly employed to increase the biocompatibility of polymers for gene delivery is the conjugation of a hydrophilic polymer to a cationic polymer. A hydrophilic polymer commonly used for this purpose is polyethylene glycol (PEG). This polymer has been conjugated to all three of the cationic polymers mentioned so far (PLL, PEI, and PBAE) in order to improve their biocompatability. PEG improves the colloidal stability of the polyplex by forming a "stealth coating" that stabilizes the polyplex against protein adsorption and self-aggregation as well increase circulation time in the blood. Another technique used to improve the biocompatibility of cationic polymers is the incorporation of carbohydrates into the polymer structure. Some of the earlier polymers tested were called poly(glycoamidoamines)s (PGAAs), polymers of open-chain monosaccharide monomers units (such as dimethyl-meso-galactarate and dimethyl-D-glucarate) conjugated to PEI-like polyamines (FIG. 8) (Liu, Y.; Reineke, T. M. Hydroxyl stereochemistry and amine number within poly(glycoamidoamine)s affect intracellular DNA delivery. *J. Am. Chem. Soc.* 2005, 127 (9), 3004-3015 DOI: 10.1021/ja0436446).

These saccharide-based polymers proved to be far less cytotoxic than PEI. Later, polymers incorporated saccharide moieties as pendant groups which allowed for more varied polymer architecture (including multiblock and statistical polymer) along with cell-specific targeting. For example, glucose-based cationic polymers were made through the copolymerization 2-deoxy-2-methacrylamido glucopyranose (MAG) with N-(2-aminoethyl)-methacrylamide (AEMA) (FIG. 9a). The carbohydrate block provided enhanced colloidal stability as well as reduced toxicity in the delivery of plasmid DNA (pDNA) to a variety of cell types. Similarly, the disaccharide α-α-D-trehalose has been copolymerized with AEMA to afford a polymer that has successfully delivered small interfering RNA (siRNA) with negligible toxicity (FIG. 9b). Lastly, a series of diblock glycopolymers were made with N-acetyl-D-galactosamine (GalNAc) which not only helped with colloidal stability and toxicity but allowed for the targeting of hepatocytes via asialoglycoprotein receptors (ASGPRs) present on these liver cells (FIG. 9c) (Dhande, Y. K.; Wagh, B. S.; Hall, B. C.; Sprouse, D.; Hackett, P. B.; Reineke, T. M. N-Acetylgalactosamine Block-co-Polycations Form Stable Polyplexes with Plasmids and Promote Liver-Targeted Delivery. *Biomacromolecules* 2016, 17 (3), 830-840 DOI: 10.1021/acs.biomac.5b01555).

By incorporating degradability and hydrophilic character, significant progress has been made in making polymeric delivery agents less toxic. These steps to increase biocompatibility of the polymers, however, tend to limit the transfection efficiency of these polymers. There is still a need for a polymer-based gene delivery system that transfects a broad range of cells at a high efficiency with minimal toxicity.

Potential of Advantages of Using Quinine Copolymers for Gene Delivery

Another common method for inducing endosomal escape and increasing the transfection efficiency of polymeric vectors is to give the cells a dose of the antimalarial drug, chloroquine (FIG. 10a). This compound is known to be a lysosomotropic agent that buffers the pH of the endosome which inhibits nuclease degradation and induces endosomal escape. This mechanism also contributes to chloroquine's antimalarial properties. The protonation of chloroquine's basic amines allows the compound to accumulate in the acidic vacuole of the plasmodium (the protozoan parasite that causes malaria) at high concentrations. Here, chloroquine binds to free heme and hemazoin (the degradative by-products of hemoglobin digestion) and inhibits the continual formation of hemazion.[2] In other words, these antimalarials inhibit the plasmodium from disposing of the toxic waste it accumulates from digesting its food. Although the exact mechanism of quinine's antimalarial activity is unknown, it is thought to work through the same mechanism as other quinoline-containing antimalarials like chloroquine.

Besides just sharing the quinoline ring, chloroquine and quinine both have basic tertiary amines ($pK_a$=10.8 and 8.5, respectively) that are similar to the amine contained on AEMA ($pK_a$=9.3)[52] (FIG. 10b) which is used as the cationic monomer in some of the glycopolymers of the Reineke group (FIG. 9) (Wu, Y.; Wang, M.; Sprouse, D.; Smith, A. E.; Reineke, T. M. Glucose-containing diblock polycations exhibit molecular weight, charge, and cell-type dependence for pdna delivery. *Biomacromolecules* 2014, 15 (5), 1716-1726 DOI: 10.1021/bm5001229; Dhande, Y. K.; Wagh, B. S.; Hall, B. C.; Sprouse, D.; Hackett, P. B.; Reineke, T. M. N-Acetylgalactosamine Block-co-Polycations Form Stable Polyplexes with Plasmids and Promote Liver-Targeted Delivery. *Biomacromolecules* 2016, 17 (3), 830-840 DOI: 10.1021/acs.biomac.5b01555; and Sizovs, A.; Xue, L.; Tolstyka, Z. P.; Ingle, N. P.; Wu, Y.; Cortez, M.; Reineke, T. M. Poly(trehalose): Sugar-coated nanocomplexes promote stabilization and effective polyplex-mediated siRNA delivery. *J. Am. Chem. Soc.* 2013, 135 (41), 15417-15424 DOI: 10.1021/ja404941). It is important to note as well, that the 4-aminoquinoline nitrogen of chloroquine is significantly more basic than the quinoline nitrogen of quinine ($pK_a$=8.1 vs. 5.2, respectively), but quinine's quinoline nitrogen may still provide some "proton-sponge" capacity since its $pK_a$ falls just above the pH of lysosomes (pH=4.5-5.0). Quinine also has the advantage of having a primary olefin that lends itself to being copolymerized without functionalizing the amines important to its activity.

In addition, quinine copolymers provide a special opportunity for analyzing the intracellular behavior of polyplexes. Quinine's fluorescence is selectively deactivated with increasing Cl⁻ concentration and can be quantified according to the Stern-Volmer relationship of fluorescence deactivation. This relationship has even been found to hold true for quinine covalently attached to a polymeric backbone. For this reason, quinoline-containing compounds, such as quinine, have been used as chloride-sensitive fluorescent indicators for studying chloride transport in important physiological processes. Chloride-sensitive dyes have been used to show Cl⁻ accumulation during the endosomal buffering process by PEI and polyamidoamines (PAM). Therefore, by analyzing the fluorescence of quinine-containing polyplexes upon endocytosis and entrapment in endocytic vehicles undergoing acidification, one can directly analyze the polymer's ability to buffer the endosome, induce chloride accumulation, and promote lysis in real time using confocal microscopy.

In summary, quinine is a natural product that provides a simple route to copolymerization, basic amines for binding to DNA and potentially aiding in endosomal escape, intercalation for polyplex stabilization, and well-characterized fluorescent properties allowing for "theranostic" analysis of intracellular trafficking via fluorescence microscopy.

Potential Medical Applications of a Quinine-Based Transfection Agent

An effective polymer-based transfection agent could be applied to many cell types that are of interest to the medical community, but focus will be paid to one potential application that would be explored. A disease called epidermolysis bullosa (EB) is currently being studied. EB is a severe genetic disorder of connective tissue which leads to extremely fragile skin. Common symptoms include severe blistering, constriction of joints and muscles, and impaired wound healing. The disease causes significant morbidity and a shortened lifespan for those afflicted. The disorder is caused by loss-of-function mutations of the COL7A1 gene which encodes for collagen type VII (C7), a protein that secures the epidermis to the underlying epidermis of the skin. Although there is currently no cure for this disease, stem cell therapy has been shown to be a potentially effective treatment option (FIG. 11a). Due to the risks associated with bone marrow stem cell transplants from donors, however, work is being done to modify the patient's own stem cells to produce collagen.

Clustered regularly interspaced short palindromic repeats (CRISPR)/Cas9 is a new gene-engineering system that can accurately insert a gene of interest into a precise location on the human genome. Cas9 (Cas=CRISPR associated protein) is a nuclease that can induce a DNA double-stranded break (DSB) at a location determined by a single-guide RNA (sgRNA) that encodes for the target gene on the genome. This break in the DNA can induce homology-directed repair (HDR) of the DNA which allows a donor gene to be inserted at that location. Practically speaking, this technology allows for the accurate replacement of the malfunctioning gene with a properly-functioning gene. In order to make this technology work, two plasmid DNA constructs must be transfected into the cell: (1) pDNA that encodes for both the sgRNA and Cas nuclease, (2) pDNA that contains the properly-functioning COL7A1 gene. In order to use the CRISPR/Cas9 system to engineer IPSCs, there must efficient delivery of both the sgRNA/Cas plasmid and the donor gene (COL7A1$^+$). Although significant progress has been made in improving the transfection of IPSCs with glycopolycations, more work needs to be done in order to improve the transfection efficiency of IPSCs in order to make the process timely and cost-effective. A quinine-based polymeric transfection agent may prove to efficiently transfect IPSCs with limited toxicity, which would allow stem-cell therapy treatment development for EB to be greatly expedited. Once successful, this polymeric transfection agent could then be applied to the transfection of many other medically-relevant cell types currently being investigated, including fibroblasts, hepatocytes, and lymphocytes. Efficient transfection of these cell types would have significant implications for advancing the treatment of a wide range of genetic disorders.

Copolymers disclosed herein can include block copolymers, random copolymers or combinations thereof. Copolymers formed herein can be formed using free radical polymerization, for example. Copolymers include at least one cinchona alkaloid containing compound and at least one methacralyamide containing monomer, acrylate containing more, or derivatives thereof.

Cinchona alkaloid containing compounds can include quinine, pseudoenantiomers cinchonidine, quinidine, and quiniline, as well as derivatives thereof. In some embodiments, useful cinchona alkaloid containing compounds can include quinine, for example.

Monomers that can be combined with cinchona alkaloid containing compounds can include methacrylamide containing monomers, acrylate containing monomers, or derivatives thereof, or combinations thereof. Particular illustrative monomers can include, for example acrylamide (Am), (2-hydroxyethyl)acrylamide (HEAm), (2-hydroxyethyl) acrylate (HEA), N-isopropyl acrylamide (NIPAm), N,N-Dimethyl acrylamide (DMAm), methylacrylamide (MA), 2-(dimethylamino) ethyl methacrylate (DMAEMA), 2-(dimethylamino) ethylacrylamide (DMAEAm), or combinations thereof.

Disclosed polymers can be formed by combining the at least one cinchona alkaloid containing compound and at least one methacralyamide containing monomer, acrylate containing more, or derivatives thereof in a solvent. In some embodiments ethanol or another alcohol can be utilized. In some embodiment copolymerization in an alcohol, such as ethanol for example can increase the amount of the cinchona alkaloid containing compound that is incorporated into the copolymer.

In some embodiments, a solution or feedstock to form the copolymer can include at least 50% (by weight or volume) of the cinchona alkaloid containing compound. In some embodiments, a copolymer can include from 5% to 25% of the cinchona alkaloid containing compound. In some embodiments, a copolymer can include more cinchona alkaloid containing compound. In some embodiments, copolymers can have any useful molecular weight, and in some embodiments, copolymers can have a molecular weight from 5 to 25 kilodaltons (KDa), or 8 to 22 KDa.

Disclosed copolymers can be combined with a genetic component to form a polyplex, which can be referred to as a copolymer-genetic component complex. A genetic component, as utilized herein can refer to DNA (which can include, but is not limited to plasmids, synthetic DNA, circular DNA fragments, linear DNA fragments, modified DNA and combinations thereof), RNA (which can include, but is not limited to messenger RNA, doubled stranded RNA, guide RNA, methylated RNA, modified RNA, synthetic RNA, and combinations thereof), proteins (which can include, but is not limited to modified proteins, synthetic proteins, and combinations thereof), or combinations thereof. Useful complexes can have any useful dimensions, in some embodiment, useful complexes can have an average diameter (e.g., hydrodynamic diameter) of not greater than 125 nanometers (nm), not greater than 110 nm, not greater than 105 nm, or even not greater than 100 nm for example.

Disclosed copolymers can be utilized in various applications, including chiral catalysis, antibacterial coatings, delivery of genetic cargo (e.g., plasmids) for transient gene transfection, for example, and gene editing, for example. Genetic cargo can be delivered via the disclosed complexes for both in vitro and in vivo (both clinical and non-clinical) applications.

The present disclosure is illustrated by the following examples. It is to be understood that the particular examples, materials, amounts, and procedures are to be interpreted broadly in accordance with the scope and spirit of the disclosure as set forth herein.

EXAMPLES

Instruments and Materials

Nuclear magnetic resonance (NMR) spectroscopy polymer characterization studies were done using a Bruker Avance III AX-400 with a BBO SmartProbe. Polymerization kinetic studies were performed with a Bruker Avance III AV-500 with a TBO triple resonance PFG probe. Size exclusion chromatography (SEC) experiments were done with an Agilent Technologies 1260 Infinity instrument equipped with an Optilab-TrEX refractometer ($\lambda=658$ nm) and Wyatt HELEOS II static light scattering detector ($\lambda=662$ nm). Samples were dissolved in the aqueous eluent consisting of 0.10 M $Na_2SO_4$ in 1.0 wt % acetic acid and run at flow rate of 0.3 mL/min on Eprogen columns [CATSEC1000 (7 μm, 50×4.6), CATSEC100 (5 μm, 250×4.6), CATSEC300 (5 μm, 250×4.6), and CATSEC1000 (7 μm, 250×4.6)]. Polyplexes were analyzed with a gel electrophoresis kit (Invitrogen, Carlsbad, Calif.) and illuminated using a Spectrolin Bi-O-Vision UV transilluminator ($\lambda=366$ nm) (Westbury, N.Y.) and photographed with a 16 MP digital camera with 28 mm lens (LG G4; Seoul, South Korea). Dynamic light scattering (DLS) was performed with a Brookhaven Instruments BI-200SM ($\lambda=637$ nm) (Holtsville, NW) and Malvern Zetasizer Nano ZS (Worcestershire, UK). Luciferase assay was performed using Promega's Luciferase Assay System (Madison, Wis.) and protein content was measured using a Bio-Rad's QuickStart Bradford Protein Assay Kit (Hercules, Calif.). Plate readings for luciferase, MTT, and protein assays were done using a BioTek Plate Reader (Winooski, Vt.). Fluorescence microscopy was carried out using an EVOS Digital Microscope (AMG Life Technologies, Grand Island, N.Y.). Cy5 uptake was measured using a BD FACS-Verse (BD Biosciences, San Jose, Calif.) with dual lasers ($\lambda=488$ nm and 640 m), seven detectors, and analyzed using FlowJo software (Ashland, Oreg.).

All chemicals were purchased from Sigma Aldrich and used as received unless mentioned otherwise. All solvents were ACS grade. All cell culture media was purchased from Life Technologies (Grand Island, N.Y.). MTT reagent was purchased from Invitrogen (Carlsbad, Calif.). Human cervical carcinoma (HeLa, ATCC CCL-2) cell line was purchased from ATCC (Manassas, Va.). gWiz-luc plasmid was sourced from Aldevron (Fargo, NS). JetPEI was purchased from Polyplus-Transfection Inc. (Illkirch, France). Quinine was purchased from Alfa Aesar (Tewksbury, Mass.).

Widefield Microscopy with Deconvolution. Widefield Epiflourescence microscopy was performed using a Zeiss TIRF scope (Oberkochen, Germany). Four separate fluorescence channels were collected on each sample, corresponding to four fluorophores present: Cy5 (ex. 650 nm, em 673), Lysotracker® (ex. 578, em. 589), GFP (ex. 488 nm, em. 509 nm), and quinine (ex. 251, em 460 nm). Images were taken with dimensions of 81.92 um×81.92 um with z-slices of 240 nm. Slice number in samples ranged from 16 to 202. Slices and image dimensions were refined when processed to exclusively reflect cellular volume. Raw images were collected using ZEN Black 2.3 spl (Zeiss, Stockholm, Sweden) at the University Imaging Center at the University of Minnesota. One limitation in the area of wide field microscopy, is convolution from out of focus z-stacks. Widefield images contain residual noise from other image stacks, whereby the degree and location of the out of focus convolution is proportional to its point spread function. Deconvolution has been an iterative mathematical tool shown to alleviate this problem, and allow for point based image analysis. Huygens deconvolution software version:17.10.0p5 (Scientific Volume Imaging, The Netherlands) was used to perform batch deconvolution on all widefield images using the CMLE algorithm with SNR:40, Q threshold of 0.01, with a maximum iterations of 50. The Minnesota Supercomputing Institute was used to execute the necessary calculations.

Polymer Synthesis

Free-Radical Copolymerization of Quinine. In a 20 mL vial, quinine (0.973 g, 3.00 mmol), comonomer (with initiator removed) (3.00 mmol), and 2,2'-Azobis(2-methylpropionitrile) (AIBN) (9.9 mg, 0.060 mmol) were added and dissolved in ethanol (5 mL). Upon addition of magnetic stir bar to vial and sealing with a rubber septum, and the reaction mixture was purged with $N_2$ for 30 min while stirring. The reaction mixture remained under $N_2$ atmosphere and was heated to 70° C. and left to stir for 24 hours. The reaction was quenched by exposure to the atmosphere. Product was purified by either precipitation or dialysis. If precipitated, the reaction mixture was added drop-wise to a suitable solvent (e.g. diethyl ether) (500 mL) while the solvent was stirred rapidly. The precipitant was filtered using a Buchner funnel, dissolved in a minimal volume of ethanol, re-precipitated in suitable solvent, filtered, left to dry under vacuum, and collected as off-white flakes. If a suitable solvent was not found for precipitation, reaction mixture was dialyzed by placing in a molecular weight cut off (M.W.C.O.) membrane of 1000 g/mol and left in ethanol (1 L) for 48 hours, changing solvent twice daily. The solvent was changed to 1:1 ethanol/deionized water and then to pure deionized water over the course of 48 hours. The product was lyophilized for 48 hours yielding an off-white powder. Products were characterized using SEC and $^1$H-NMR.

Polyplex Formation and Characterization.

Polyplexes were formed by solubilizing the polymer in ultrapure water. If polymer did not solubilize after vigorous vortexing, an addition of 4 μL acetic acid buffer (3 M, pH=5.5) was added per 1 mL of polymer solution. The polymer solution was diluted in ultrapure water to the determined N/P ratio/concentration before being added to an equal volume solution of pDNA in ultrapure water (0.02 μg/μL). The samples were left to incubate at room temperature for 1 hour.

DNA Binding Studies by Gel Electrophoresis. After the 1 hour incubation period, the polyplex solutions of all N/P ratios (10 μL) were each mixed with a 30% glycerol solution in water (2 μL). The solutions were loaded into 0.6% agarose gel containing ethidium bromide (6 μL/100 mL TAE buffer) and run at 60 V for 60 minutes. The gel was visualized under UV transilluminator ($\lambda=366$ nm).

Dynamic Light Scattering (DLS). For determining size of polyplexes using DLS, polyplexes were formed at an N/P=10 in ultrapure water (0.05 mg/ml) and left to incubate at room temperature for 1 hour. Each polpylex solution was passed through a 0.2 μm filter to remove dust and analyzed by either the Brookhaven Instruments BI-200SM or Malvern Zetasizer Nano ZS at 37° C.

Transfection Studies In Vitro

Cell Culture. HeLa cells were cultured in DMEM containing 10% fetal bovine serum (FBS) and an Antibiotic/Antimycotic solution (Life Technologies, Grand Island, N.Y.) to yield final concentrations of 10 μg/mL of penicillin, 25 μg/mL of streptomycin, and 25 ng/mL of Fungizone.

Cells were cultured in 75 cm² flasks at 37° C. under 5% $CO_2$ atmosphere and were monitored for confluency and passaged regularly. When plated, the cells were trypsinized and then diluted in DMEM containing 10% FBS. The cells were counted using a hemocytometer and viable cells were identified by staining dead cells with trypan blue. For luciferase and MTT assays, each well in the 24-well plates were plated with 50,000 cells diluted in 1 ml of DMEM containing 10% FBS.

MTT Cell Viability Assay. Twenty-four hours after plating the cells, the media was aspirated and the cells were washed with 1× phosphate-buffered saline (PBS). Three wells of 50,000 cells each were designated for each polymer and N/P ratio. Polyplexes, prepared in the same manner as above, were diluted two-fold with Opti-MEM and the solution (300 µL) was added to each well. The cells in the polyplex solution were left to incubate for four hours at 37° C. under 5% $CO_2$ atmosphere. After the incubation period, 1 mL of DMEM containing 10% FBS was added to each well and left to incubate at 37° C. and 5% $CO_2$. Twenty-four hours after transfection, the media was replaced with 1 mL of fresh DMEM with 10% FBS. Forty-eight hours after transfection, the media was replaced with 1 mL of DMEM containing 10% FBS and 0.5 mg/mL MTT. After an incubation period of 1 hour at 37° C. and 5% $CO_2$, the media was aspirated and the cells were washed with 1×PBS. Dimethyl sulfoxide (DMSO) (600 µL) was added to each well and the plate was left on an orbital shaker for 15 min to lyse the cells. The lysate (200 µL) from each well was pipetted into a clear 96-well plate, and the absorbance for each sample was measured at 570 nm.

Propidium Iodide Cell Viability Assay and Polyplex Uptake. GWiz-Luc luciferase plasmid was labelled with C5 per manufacturer's instructions (Minis Bio LLC, Madison, Wis.). Polyplexes were formed in same manner as above with Cy5-labeled pDNA. The polyplexes were introduced to cells in the same manner as the MTT viability assay. After the incubation of four hours at 37° C. and 5% $CO_2$, cells were washed with 2×PBS and trypsinized for 10 min before DMEM (1 mL) was added. After transferring to a falcon tube and centrifuging (1120 g, 4 min), the cells were rinsed with 1×PBS and 100 µL PBS solution, containing 2.5 µL of propidium iodide, was added to tube. The tubes were vortexed before running on the flow cytometer. Measurements were made in triplicate and the median Cy5 intensity for each sample was recorded along with the percentage of cells positive for Cy5.

List of Acronyms
AEMA N-(2-Aminoethyl)-methacrylamide
AIBN 2,2'-Azobis(2-methylpropionitrile)
ASGPR Asialoglycoprotein Receptor
ATRP Atom Transfer Radical Polymerization
BMT Bone Marrow Transplant
C7 Collagen type VII
Cas CRISPR associated proteins
CD Circular Dichroism
CRISPR Clustered Regularly Interspaced Short Palindromic Repeats
CTA Chain Transfer Agent
Cy5 Cyanine fluorophore
DMA N,N'-Dimethylacrylamide
DMF Dimethylformamide
DLS Dynamic Light Scattering
DMEM Dulbecco's Modified Eagle's
DNA Deoxyribonucleic Acid
DSB Double-Stranded Break (DNA)
EB Epidermolysis Bullosa
EtOH Ethanol
FBS Fetal Bovine Serum
FITC Fluorescein Isothiocyanate
GalNAc N-Acetyl-D-galactosamine
GFP Green Fluorescent Protein
HDR Homology Directed Repair
HEA 2-Hydroxyethyl acrylate
HEMA 2-Hydroxyethyl methacrylate
HeLa Human uterine cervical carcinoma
IPSCs Induced Pluripotent Stem Cells
MA Methyl acrylate
MAG 2-Deoxy-2-methacrylamido glucopyranose
MeOH Methanol
MMA Methyl methacrylate
MTT 3-(4,5-Dimethylthiazol-2-yl)-2,5-diphenyltetrazolium bromide
NIPAm N-Isopropylacrylamide
NMP Nitroxide-Mediated Polymerization
NMR Nuclear Magnetic Resonance
PAM Polyamidoamines
PBAE Poly(β-amino esters)
PCR Polymerase Chain Reaction
pDNA Plasmid Deoxyribonucleic Acid
PEI Polyethylenimine
PGAA Poly(glycoamidoamine)
PI Propidium Iodide
PLL Poly(L-lysine)
PEG Polyethylene glycol
PMAEMT Poly(N-methyl aminoethylmethacrylate)
RAFT Reversible Addition-Fragmentation Chain-Transfer
RDRP Reversible Deactivation Radical Polymerizations
RI Refractive Index
RNA Ribonucleic Acid
SEC Size Exclusion Chromatography
sgRNA Single Guide RNA
siRNA Small Interfering Ribonucleic Acid
TBDMS Tert-butyldimethylsilyl
UV-Vis Ultraviolet-Visible Spectroscopy
VAc Vinyl acetate
VP N-vinylpyrrolidone Example 1

Synthesis of Quinine Copolymers

The free-radical homopolymerization and copolymerization of quinine was run following the procedure outlined by Kobayashi et al. In their report, Kobayashi et al. performed free-radical copolymerization with quinine (1) and acrylonitrile (2) (at a variety of monomer feed ratios) in a variety of organic solvents with 0.048 eq AIBN (Scheme 1) as the initiator. They ran the reaction at reflux (60-80° C., depending on solvent) for up to 48 hours under nitrogen atmosphere.

Here, the copolymerization was performed with a variety of olefin-containing monomers with different activating groups. N,N'-Dimethylacrylamide (DMA), methyl acrylate (MA), methyl Scheme 1.

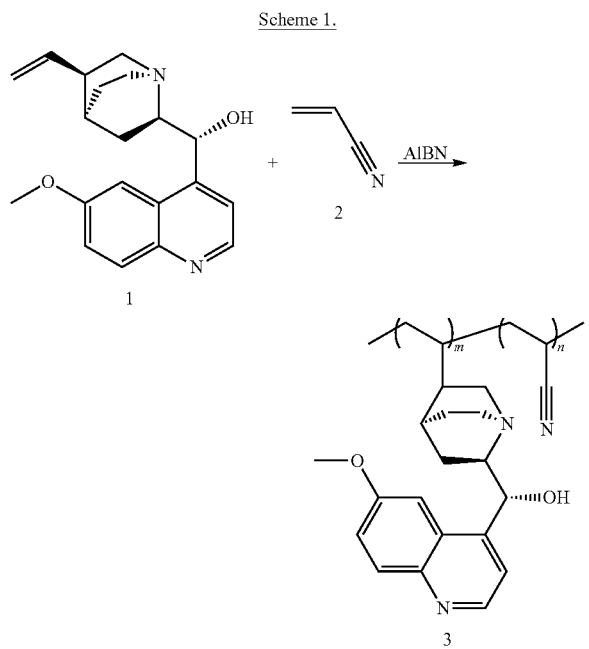

methacrylate (MMA), and vinyl acetate (VAc) are monomers that are simple members of the acrylamide, acrylate, methacrylate, and acetate monomer families (FIG. 12a). These simple monomers can be used to compare the reactivity of quinine to each monomer family while limiting differences in reactivity due to pendant groups. Conversion, yield, molecular weight, and composition of these copolymerizations will be optimized. Some of the conditions that can be altered to optimize the copolymerization include changing the solvent, temperature, comonomer feed ratio and concentration, equivalence/type of initiator, and length of reaction time.

The reaction kinetics for each comonomer was measured using variable-temperature $^1$H-NMR. Monomer consumption was measured by integrating the alkene proton peaks (δ 6.5-5.5 ppm) for each monomer and monitoring the peak's decrease in relation to a peak whose integration will remain the same, such as one of quinine's aromatic peaks (δ 8.7-7.3 ppm). It is thought that the decrease in the alkene peaks for each monomer is caused by its incorporation into the polymer. This is correct if there is (1) a proportional increase in the polymer backbone ($CH_2$) protons (δ 2.5-1.0 ppm) as the alkene peaks decrease and (2) the same comonomer fraction is found in the final isolated polymer. If these conditions are met, polymer's composition can be monitored by quantifying the decrease in each monomer's alkene peaks to low conversion (<10%).[62] Since the starting monomer feed and the polymer's composition at low conversion are known, a non-linear fit with the Mayo-Lewis equation can be used to determine the reactivity ratio of the copolymerization of quinine and each monomer type. This knowledge will allow one to calculate the polymer composition for the copolymerization of quinine and monomers from several families at any given monomer feed ratio.

After determining quinine's reactivity with each monomer family, copolymerization of quinine was carried out with hydrophilic monomers from these families. For example, 2-hydroxyethyl acrylate (HEA), 2-hydroxyethyl methacrylate (HEMA), N-isopropylacrylamide, (NIPAm), and DMA was tested due to their hydrophilicity, biocompatibility, and use in a variety of polymeric biomaterials (FIG. 12b).[63-65] The reactivity ratios of these copolymerizations will be assessed in the same manner as previous monomers. The polymers can be isolated and purified in several ways. In Kobayshi et al.'s procedure, the polymer precipitated in solution, was filtered, dissolved in dimethyl formamide (DMF), and re-precipitated in methanol.[9] Like Kobayashi et al., purification through precipitation was used as an expedient method for purifying the quinine copolymers. Multiple precipitations may be necessary to get rid of any residual monomer. One difficulty of this process will be differences in solubility between polymers and the potential difficulty of finding a suitable solvent. If precipitation is difficult due to solubility issues, dialysis will serve as an alternative method for purifying the polymers. In this method, the residual monomer will be separated by selective diffusion through a porous bag in a solution such as water. The dissolved polymer solution can then be frozen and the water can be lyophilized off to yield purified polymer.

Characterization of Quinine Copolymers

The polymer's physical composition was analyzed using SEC and $^1$H-NMR. Analysis by SEC will give important properties of the polymer such as number-average molar mass ($M_n$), mass-average molar mass ($M_w$), and dispersity (Đ) of the polymer. Đ is the ratio of $M_n/M_w$ and describes how uniform in size the polymer chains are.[26] If all the polymer chains are of the same size, Đ=1.0. As the distribution in polymer chain sizes grows, Đ increases. For a typical bulk free-radical polymerization to low conversion in a batch reactor, Đ will be typically range between 1.5-2.0. One might expect that the quinine copolymers will have a dispersity in this range since it is free-radical polymerization. If the quinine is truly attached to the polymer, the UV detector on the SEC will show a UV trace coinciding with the refractive index (RI) and light scattering detectors due to the quinine's ability to absorb UV light (FIG. 13b).

Purified quinine copolymers were analyzed by $^1$H-NMR. The NMR spectrum should feature broad peaks between 2.5-1.0 ppm due to the backbone $CH_2$ protons and peak broadening for the remaining downfield protons (FIG. 13a). Quinine's three alkene protons (δ 6.5-5.5 ppm) will disappear when quinine is incorporated into the polymer since the protons of the double bond will become protons on spa carbons after propagation. The percentage of each monomer in the polymer will be calculated from the ratio of the peaks corresponding to the protons in each monomer's pendant group. Additionally, UV-vis spectroscopy can be used to determine the approximate quinine incorporation within the polymer. For a given wavelength, the molar absorptivity of quinine in solution can be determined using the Beer-Lambert law, $$A = \varepsilon b c \quad (3\text{-}1)$$

where A is the total absorbance, ε is the molar absorptivity (or extinction coefficient), b is the path length, and c is the concentration. Using the standard molar absorptivity and known concentration of polymer in solution, the mass of quinine per gram of polymer can be calculated, determining the percentage of quinine within the polymer (FIG. 13c). Lastly, potentiometric titration can be used to measure the $pK_a$ of quinine copolymer's basic amines in order to see how polymerizing quinine affects the compound's basicity. The polymer will be dissolved in an HCl solution (pH=1), slowly titrated with NaOH, and the solution pH will be measured using a pH electrode. Accurately measuring the $pK_a$ can predict the polymer's ability to buffer the acidic endosome.

Modifying Quinine Copolymer Structure

A library of copolymers was synthesized using the general free-radical polymerization procedure outlined in Scheme 1. The copolymers will be tested for DNA binding, transfection efficiency, and toxicity (according to the procedure outlined in the next section). The results of these biological studies will show which monomers should be explored more in-depth. The structure of the most promising copolymers will be altered systematically in order to explore the effects of molecular weight, dispersity, and quinine percentage on the polymer's biological properties. The polymer composition could be modified by varying the comonomer ratio in the feed in order to increase or decrease the percentage of quinine in the polymer. Large differences in reactivity between the comonomers and quinine, however, may limit the extent of quinine incorporation, and chain transfer and termination reactions may significantly hinder control of molecular weight and dispersity.

One method to gain more control over quinine incorporation is to modify quinine's vinyl group so its reactivity is more similar to its comonomer. Scheme 2, adapted from Rowan et al., (Rowan, S. J.; Sanders, J. K. M. Macrocycles derived from cinchona alkaloids: A Scheme 2. Synthesis of modified quinine acrylate/methacrylate monomer

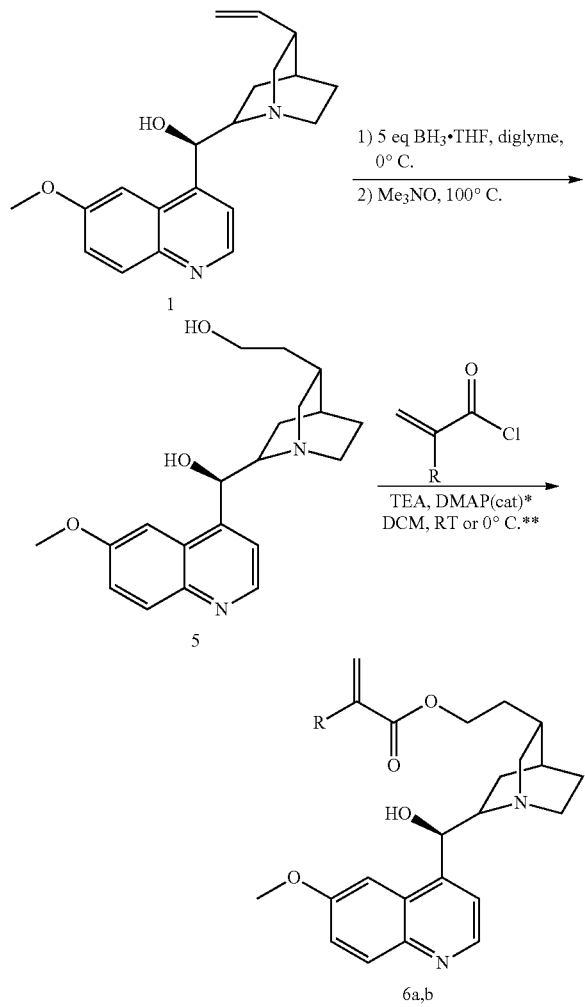

*attempt without DMAP first
**Try RT first
a) R = H (acrylate)
b) R = CH₃ (methacrylate)

thermodynamic vs kinetic study. *J. Org. Chem.* 1998, 63 (12), 1536) shows a two-step procedure for producing an acrylate- or methacrylate-functionalized quinine. The first step includes the hydroboration of the primary alkene using triborohydride ($BH_3$) and trimethylamine N-oxide dihydrate ($Me_3NO$) to give the primary alcohol 5 in the anti-markovnikov position. The primary alcohol 5 can then undergo nucleophilic substitution with either methacryloyl chloride to yield the methacrylate 6a or with acryloyl chloride to yield the acrylate 6b. It is likely that the protection of the secondary alcohol is not necessary in this substitution step due to the steric hindrance of the secondary alcohol. If the substitution reaction, however, is not selective for the primary alcohol, the secondary alcohol will be protected with tert-butyldimethylsilyl (TBDMS) according to Rowan et al.'s procedure. With this modified quinine monomer, the reactivity of the quinine and comonomers will be far more similar and a wider range of polymer compositions can be achieved simply by modifying the monomer feed ratio.

Controlled Radical Polymerization via RAFT

Once the free-radical copolymerization of quinine with a variety of comonomers was characterized, controlled radical polymerization techniques will be attempted in order to gain more control over the molecular weight and dispersity of the polymers. A truly controlled or "living" polymerization is a polymerization where there is no termination or transfer reactions which leads to a narrow distribution of chain sizes (low Đ). A popular technique for achieving low dispersities in radical polymerizations is by using Reversible Addition-Fragmentation Chain-Transfer Polymerization (RAFT). RAFT polymerization is accomplished using a special chain transfer agent (CTA), typically a dithioester, which can reversibly add to the propagating radical chains and create a rapid dynamic equilibrium between active and dormant species (FIG. 14a). This degenerate chain transfer allows the chains to begin growing roughly at the same time and have equal opportunities to propagate. This is accompanied by a reduction in termination due to a decreased radical concentration. These properties allow for a controlled reaction where the molecular weight of the polymer can be accurately targeted and the dispersity of the polymer remain lows (Đ<1.1) (FIG. 14b).

As one of several reversible deactivation radical polymerizations (RDRP), RAFT has proven to be robust, versatile, and broadly applicable to monomers that polymerize under free-radical conditions. The choice of an appropriate CTA agent is critical for RAFT polymerization to work properly. Unfortunately RAFT polymerization of less-activated monomers (e.g. vinyl acetate) tend to be problematic with active RAFT CTA agents that work well for more active monomers (e.g. methyl acrylate). RAFT polymerization of unactivated monomers with active CTA agents tend to inhibit polymerization since the propagating radicals tend to be poor homolytic leaving groups (FIG. 15a). A careful choice of CTA agent may be necessary for a polymerization with monomers of very different reactivities. For example, the appropriate "Z" and "R" groups for the polymerization of methyl acrylate (MA) and quinine will lie on the overlapping regions of FIG. 15b for MA and the less active monomers (denoted by VAc=vinyl acetate). Following these guidelines, an appropriate CTA for quinine copolymerizations may contain Z=OPh and R=isopropyl ethyl ester. It is likely that trials with multiple CTA agents may be necessary before finding one that works well in this system.

If RAFT proves to be ineffective in the controlled polymerization of quinine copolymers, other radical living polymerization techniques could also be explored, including nitroxide-mediated polymerization (NMP) or atom transfer radical polymerization (ATRP). Anionic polymerization may even be possible as long as quinine's secondary hydroxyl group is protected (with TBDMS, for example). If RAFT, NMP, or ATRP methods are successful, this would likely be the first example of a quinine copolymer polymerized using a controlled polymerization technique. Controlled polymerization with the unmodified quinine, however, is worth pursuing due to the broad applicability that may be achieved using an un-modified natural product such as quinine.

Achieving RAFT polymerization of quinine copolymers not only allowed for the generation of copolymers with varied molecular weight and low dispersity, but RAFT will allow incorporating quinine copolymers into more complex architectures, such as block copolymers. Polymerization with a RAFT CTA agent produces polymer chains that are "dormant" and contain the CTA agent as an end group. These "macro-CTAs" can be polymerized with another monomer to create diblock copolymers. FIG. 16 shows two proposed diblock copolymers where one block is a homopolymer and the other is a statistical copolymer containing quinine. In FIG. 16a, the hydrophilic block consists of poly(HEA-s-quinine) where quinine is protonated and the hydrophobic block consists of poly(styrene). If formed at slightly acidic pH, the quinine will be protonated and the polymer will form into a micelle that can bind nucleic acids. The micelle's hydrophobic core adds structural integrity to the polyplex for enhanced stability and adds the possibility of using the core as a carrier for hydrophobic drugs that could enhance delivery (such as dexamethasone, which helps with nuclear internalization). FIG. 16b shows another diblock copolymer with a hydrophobic block consisting of poly(NIPAm-co-quinine). Since quinine is fairly hydrophobic at a slightly elevated pH (when not protonated), a quinine copolymer could form the hydrophobic core of a micelle. A hydrophilic cationic block such as poly(AEMA) could bind pDNA, and upon entry to the more acidic endosome, protonation of the quinine would allow for solvation of the hydrophobic core. This dissociation of the micelle could release of any stored hydrophobic compounds to help with transfection (such as dexamethasone) and enhance DNA unpacking (an important step in transfection).[73] Polymerization with thermoresponsive polymers such as NIPAm may allow for the formation of micelles that form or break apart with the application of heat. These diblock copolymer micelle systems are just a couple of many potential gene delivery vehicles that could be explored by copolymerizing quinine via RAFT.

In summary, a systematic analysis of the free-radical copolymerization of quinine with a variety of olefin-containing monomers can produce a library of statistical copolymers that can be used in gene delivery applications. After testing these simple copolymers, the more promising polymer compositions can be examined more thoroughly by changing quinine incorporation, molecular mass, and dispersity. More pronounced modifications of the copolymers can be achieved by functionalization of the quinine monomer with an acrylate or methacrylate reactive center and by using controlled polymerization techniques such as RAFT. If successful, RAFT will allow for even more complex block architectures that could be used to form micellar gene delivery systems that utilize quinine's properties to overcome barriers in gene delivery.

Polyplex Formation and Characterization

Once a quinine copolymer is synthesized, and before it is used to transfect cells it can be bound to a nucleic acid (e.g., a genetic component) of interest to form a complex or polyplex. Although many nucleic acids may be utilized, initial results here focused on plasmid (pDNA) for its broad applicability in gene delivery applications. Gel electrophoresis is a common technique used to assess pDNA binding of polycations. The first step in this process is to mix the polymer and pDNA together to form the polyplex. The polyplex is formed according to an established protocol where the polymer and DNA solutions are mixed in a 1:1 v/v ratio by pipetting the polymer solution into the DNA solution (Wu, Y.; Wang, M.; Sprouse, D.; Smith, A. E.; Reineke, T. M. Glucose-containing diblock polycations exhibit molecular weight, charge, and cell-type dependence for pdna delivery. Biomacromolecules 2014, 15 (5), 1716-1726 DOI: 10.1021/bm5001229). Once combined, the solution is left to incubate at room temperature for 1 hour. Polyplexes are formed with varying concentrations of polymer to DNA which are expressed by their N/P ratio. The N/P ratio expresses the molar ratio of cationic amine groups on the polymer (N) over the number of anionic phosphate groups of the DNA backbone (P). Typically, as the N/P ratio is increased, the polyplex transfection is more efficient but also more toxic to the cells. In order to determine the minimum N/P ratio necessary for full complexation of the DNA, polyplexes were formed at roughly ten different N/P ratios (between 1 and 20). These polyplexes are then loaded onto an agarose gel and exposed to an electric field that pulls any negatively charged DNA that is not electrostatically bound to the polymer towards the positively-charged cathode (FIG. 17a). This assay determined whether a quinine copolymer can bind electrostatically to DNA and at what minimum N/P ratio the polymer can completely bind the DNA.

Once gel electrophoresis showed that a quinine copolymer can successfully bind DNA, the polyplexes were analyzed using dynamic light scattering (DLS) to characterize the size and stability of the polyplexes. By shining a laser through the polyplex solution and analyzing the fluctuations in scattering intensity over time, DLS can measure the average size and size distribution of the polyplexes. Polyplexes that are 100 nm or less in hydrodynamic diameter tend to be endocytosed more easily by cells and produce higher transfection efficiencies. DLS will show whether the polyplexes fall near or below this target size of 100 nm (FIG. 17b). Polyplexes must also remain in this size range and resist aggregation for the transfection period. The hydrodynamic diameter of the polyplexes was measured in Opti-MEM (MEM=modified Eagle's medium, a buffered salt solution containing small-molecule nutrients) and Dulbecco's Modified Eagle's Medium (DMEM) with 10% fetal bovine serum (FBS) (a common media used for cell culture) for a period of four hours. A dramatic increase in the hydrodynamic diameter of the polyplexes over this time frame would likely indicate aggregation of the polyplexes which may significantly inhibit transfection. Zeta potential, which measures the electric potential of the polyplex surface, compliments the DLS measurement (example shown on inset on FIG. 17b). If the polyplex is shown to have a net positive charge, the polyplex is less likely to aggregate and more likely to interact with the negatively-charged surface of the cell. Polyplex size, aggregation properties, and zeta potential will all help dictate which medium, N/P ratios, and polymer compositions (including quinine percentage) are most suitable for transfection.

Uptake, Transfection, and Toxicity Assays

Once a library of quinine copolymers was synthesized and their DNA binding properties were analyzed, the copolymers that form stable polyplexes of a suitable size underwent, transfection, and toxicity assays in a model cell line, such as HeLa (human uterine cervical carcinoma). An uptake experiment examined what percentage of living cells have endocytosed detectable levels of pDNA. A standard DNA plasmid used in this experiment is the gWiz-Luc luciferase plasmid which is labelled with a cyanine fluorophore Cy5 in order to be visualized with a helium-neon laser ($\lambda$=633 nm). A polyplex solution with 0.01 μg/μL of DNA was created using the quinine copolymer of interest at several N/P ratios (such as 5, 10, and 20). For each well of 50,000 cells, 300 μL of the polyplex solution was added 600 μL of the transfection media, such as Opti-MEM. After an incubation at 37° C. for four hours, the cells were analyzed using flow cytometry (with excitation at $\lambda$=633 nm) to determine the percentage of cells that have Cy5-positive fluoresce. The cells positive for Cy5 fluorescence have successfully endocytosed the polyplexes. The percentage of Cy5-positive cells obtained using the quinine copolymers will be compared to positive controls, such as commercial transfection agents jetPEI® (linear PEI) and Lipofectamine®, and to negative controls (cells only and cells only exposed to the plasmid DNA). The positive controls helped gauge proper gating for the flow cytometry analysis (FIG. 18a) as well as served as a benchmark for transfection efficiency. This experiment showed whether the quinine copolymers werecapable of inducing endocytosis and transporting the pDNA into the cell at levels comparable to commercial transfection agents.

The quinine copolymers that show positive uptake of Cy5-labelled DNA into HeLa cells were then tested in transfection assays where both luciferase and green fluorescent protein (GFP) expression were assessed. In both of these assays, the polyplexes are created and introduced to the cells in the same manner as the Cy5 uptake assay. After a four-hour exposure to the polyplexes, the cells are incubated for 48 hours in order to express the protein encoded by the pDNA. In the luciferase assay, the transfected cells produce the enzyme luciferase which can be detected by adding the compound luciferin to the lysed cell culture and measuring the intensity of chemifluorescence. The transfection efficiency can be determined by taking the ratio of the chemifluorescence intensity over to total amount of protein produced in the well measured with a Bradford protein assay kit. As a complimentary experiment, the transfection efficiency will also be measured by a GFP-transfection assay where the cells are transfected with a DNA plasmid encoding for GFP. The level of transfection was quantified by measuring the fluorescence of light emitted from cells passing through the flow cytometer's 488 nm laser (FIG. 18b). Although similar to the luciferase assay, the GFP assay is more quantitative because it measures exactly how many cells are expressing GFP along with the mean gene expression per cell. In summary, the luciferase assay was used to quickly ascertain whether a polymer can induce any transfection while the GFP assay will provide a more quantitative measure of transfection efficiency.

Toxicity of the quinine transfection agents was carried out concurrently with the luciferase and GFP assays. When the compound 3-(4,5-dimethylthiazol-2-yl)-2,5-diphenyltetrazolium bromide (MTT) is introduced to the cells in media, the compound is reduced by metabolically-active (viable) cells to form the purple dye formazan. By measuring the absorption of 570 nm light by the cell lysate, the amount of viable cells can be determined and the toxicity of the polymer can be assessed (FIG. 18c). The cytotoxicity of the polymer can also assessed with flow cytometry during GFP analysis. By introducing propidium iodide (PI) into the cell suspension, one can assess the viability of the cells. PI is an intercalating agent that can be detected using the 488 nm laser of the flow cytometer and only permeates the membranes of non-viable cells. Therefore, the percentage of PI-positive cells measured during the GFP analysis is a reflection of the number of viable cells and reflects the toxicity of the polymer. Both MTT and PI assays will be used to determine cytotoxicity of the polymer. If a transfection with a quinine copolymer causes high levels of cytotoxicity, lowering the N/P ratio may be necessary. In order to achieve high transfection efficiency with low toxicity, however, the polymer composition may need to be adjusted in order to find the proper balance of hydrophilic and hydrophobic character and charge density.

Analysis of Polyplexes Using Fluorescence Microscopy

Figures 19A, 19B:
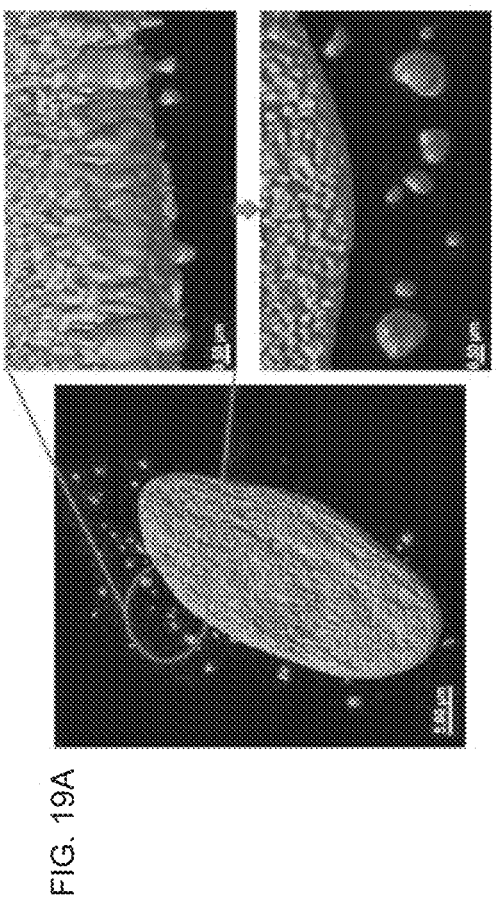
FIGS. 19A and 19B show an example of three-dimensional (3D) volume rendering of polyplexes composed of Tr4$_{55}$ polymer and HeLa cell nucleus 24 h post transfection, 19A and 19B) Confocal fluorescence imaging of HeLa cells transfected with FITC-labelled jetPEI (yellow) and DAPI-labelled nucleus (blue).

Fluorescence microscopy is a powerful diagnostic tool in the analysis of these quinine copolymer transfection agents. By using fluorescence microscopy, one can determine which intracellular barrier may be inhibiting successful transfection. Although flow cytometry can be used to determine whether the polyplexes enter the cell and if protein expression ultimately occurs, these tools cannot determine where the polyplex may get stuck in-between these two stages. By labelling the DNA and polymer with fluorescent tags, the polyplexes can be monitored by fluorescence microscopy. Confocal laser scanning microscopy is a special type of microscopy that has a very precise depth of field that can examine one horizontal slice of the cell at a time. By examining individual layers, one can precisely locate features, such as a polyplex, within the 3D intracellular space. Confocal microscopy has been used to monitor polyplex trafficking during the process of transfection and elucidate the intracellular barriers that inhibit transfection. For example, polycation composition has been correlated with the specific mechanism of endocytosis by using fluorescently-labelled antibodies to monitor clathrin-dependent vs caveolar endocytosis of polyplexes. Also, by labelling the DNA with the fluorescein isothiocyanate (FITC) fluorophore, confocal microscopy revealed how different polymers influenced the speed of internalization and the concentration of polyplexes at the nucleus (FIG. 19a). Another confocal imaging study. monitored the internalization and trafficking of glycopolycations by labelling both the pDNA and the polymer with separate fluorophores, FITC and Cy5, respectively. It was able to show how different polymers showed different capabilities of permeabilizing the nuclear membrane to induce transfection (FIG. 19b). Also, by the separate labelling of the polymer, they were able to study how free polymer was trafficked to the nucleus differently than polyplexes. Similarly to these two studies, confocal fluorescence microscopy will be used to elucidate how the quinine copolymer's composition affects its ability to overcome intracellular barriers to transfection. Also, as mentioned above, due to the selective deactivation of quinine's fluorescence by $Cl^-$, direct monitoring of endosomal buffering may be possible by quantifying the change in fluorescence of a polymer trapped in endosome over time. By using quinine's fluorescence to characterize the polyplex's intracellular trafficking pattern, efforts can then be made to change polymer's composition to overcome intracellular barriers.

Applications in Therapeutic Gene Delivery

Once a quinine copolymer system was developed that could successfully transfect a model cell line, such as HeLa, the next step includes using the polymer to deliver therapeutic genes to cells of interest for the medical community. With improved transfection efficiencies, stem cell therapy for EB patients could become a more viable treatment option. In order to test whether a quinine-copolymer transfection system could be effective in IPSCs, a GFP transfection assay would be carried out. If the transfection efficiencies and cytotoxicity appear better than current techniques (electroporation, lipofectamine transfection, or viral transformation) than a transfection will be carried out with a CRISPR/Cas9 plasmid with a sgRNA that encodes for a common point mutation seen in the COL7A1 gene of EB patients. A Surveyor nuclease assay will be used to determine what percentage of IPSCs have had their COL7A1 gene modified by the CRISPR/Cas9 system. The Surveyor assay works by using an endonuclease that cuts DNA at any point containing a mismatch mutation caused by CRISPR/Cas9 system. A gel of the cleaved DNA is run, and the intensity of the DNA fragments indicates the percentage of cells that contain mutations caused by CRISPR/Cas9. After proving positive CRISPR/Cas9 activity in IPSCs, the donor gene with the correct COL7A1 can be transfected with CRISPR/Cas9 plasmid. If wild-type collagen VII expression has been restored, a western blot was used to detect the corrected protein. To quantify the level of gene-editing, digital polymerase chain reaction (PCR) was used in order to determine the precise percentage of cells that were successfully engineered and produced the corrected collagen protein. If successful, the quinine copolymer transfection agent allowed for more rapid gene-editing of IPSCs which would make stem cell therapy of EB more practical. Once successful in one cell type, the polymer could become more broadly utilized in the gene-editing of many more medically-relevant cell types.

Copolymerization of Quinine

Figures 20A, 20B:
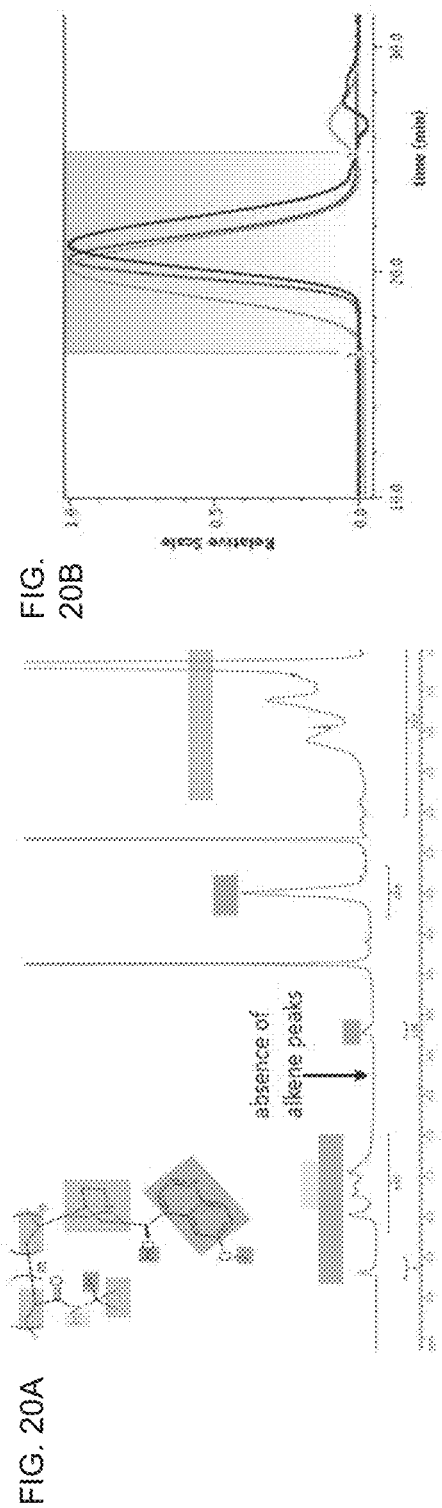
FIGS. 20A and 20B show: 20A) $^1$H-NMR of poly(NIPAm-co-quinine) purified through dialysis. 20B) Aqueous SEC trace of poly(Am-co-quinine), $M_n \sim 10^4$ g/mol, Đ=1.39. (Green=UV, red=light scattering, blue=RI).

The first free-radical copolymerization of quinine was achieved using NIPAm with a 1:1 mole ratio of NIPAm and quinine comonomers. The initiator, AIBN, was present at an 0.01 eq to the total monomer concentration of 0.5 M in DMF, and the reaction was run for 24 hours at 70° C. By measuring the decrease of alkene peaks in the NMR spectrum, this first study showed around 82% of the NIPAm monomer and 13% of the quinine monomer had been consumed which gave a 47% total monomer conversion. Increasing the initiator concentration to 0.1 eq increased the conversion to roughly 60% monomer conversion. By precipitating in 3:1 diethyl ether/hexanes, the polymer could be isolated by filtration, but purification by dialysis in methanol (MeOH) gave a product of higher purity (although yield was initially below 10% for both methods). The $^1$H-NMR of the product shows that quinine is indeed incorporated within the polymer due to the lack of alkene protons in the spectrum (FIG. 20a). By NMR analysis, the dialysis-purified product gave a polymer with roughly 13% quinine by mole fraction.

The NIPAm-quinine copolymer dissolved in the acidic buffer used for aqueous SEC and was run on the instrument to give an approximate Đ=1.05. The dispersity was surprisingly low for a free-radical polymerization, but it is hypothesized that the low dispersity was a result of the low conversion of the reaction. In subsequent reactions brought to higher conversions, the dispersity rose to values between 1.2-1.8, which value mo re in-line for a free-radical polymerization. The molecular weight for the NIPAM-quinine copolymer was approximately $M_n$~10,000 g/mol which was based off of an estimated dn/dc for the homopolymer poly (NIPAm) (dn/dc=0.167). The molecular weight of subsequent polymers, including poly(acrylamide-co-quinine) seen in FIG. 20b, were also estimated using the dn/dc of the homopolymer. Proper calculation of the dn/dc for each copolymer still needs to be carried out for all polymers. The UV detector, as seen in FIG. 20b, detected a broad signal corresponding with the signal of the RI and light scattering detector, proving that quinine is indeed incorporated within the polymer. If free quinine or its homopolymer were simply impurities in the polymer, one would expect to see a separate UV peak corresponding to the quinine impurity.

Copolymerization was carried out with monomers from several other monomer families (as described in FIGS. 12A and 12B). It was found that the percent of quinine in the polymer could be increased using ethanol (EtOH) instead of using DMF. Along with this property, EtOH was used due to advantages in cost, safety, sustainability, and compatibility with dialysis. While performing experiments to optimize the reaction procedure, increase quinine incorporation, and alter polymer structure, the copolymers summarized by Table 1 were synthesized.

TABLE 1

Summary of Quinine Copolymers Synthesized

| Comonomer | Structure | Rxn & Solvent | Initiator & Quinine Eq | Purification | Polymer Structure | % Q in Polym |
|---|---|---|---|---|---|---|
| NIPAm (N-isopropyl acrylamide) | 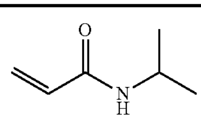 | FR, RAFT EtOH, DMF | 0.1-0.001 eq AIBN 10-90% quinine | Precipitation (Et$_2$O/ Hexanes), Dialysis | $M_n$ = ~14,000 g/mol PDI = 1.23 | ~13% (FR) ~13% (RAFT) |
| DMA (N,N-Dimethyl acrylamide) | 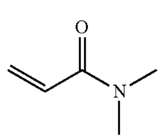 | FR, RAFT EtOH, DMF | 0.1-AIBN, CDTPA 50% quinine | Dialysis | $M_n$ = ~12,000 PDI = 1.21 | ~7% (FR) ~12% (RAFT) |
| Am (Acrylamide) | 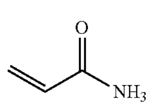 | Free Radical EtOH | 0.01 AIBN, 50% quinine | Filtered | $M_n$ = ~10,000 g/mol PDI = 1.39 | ~14% |
| HEAm (N-(2-hydroxyethyl) acrylamide)) | 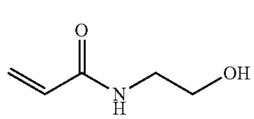 | Free Radical EtOH | 0.1-0.01 AIBN, 50-90% quinine | Precipitation (acetone) | $M_n$ = ~8,000 g/mol PDI = 1.78 | ~10% |

TABLE 1-continued

Summary of Quinine Copolymers Synthesized

| Comonomer | Structure | Rxn & Solvent | Initiator & Quinine Eq | Purification | Polymer Structure | % Q in Polym |
|---|---|---|---|---|---|---|
| MMA (Methyl methacrylate) | 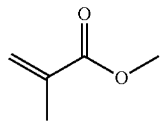 | Free Radical EtOH | 0.01 AIBN, 50% quinine | Precipitation (EtOH) | | ~3% |
| MA (Methyl acrylate) | 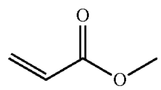 | Free Radical EtOH | 0.01 AIBN, 50% quinine | Did not find suitable solvent | | ~17% |
| HEA (N-(2-hydroxyethyl) acrylate)) | 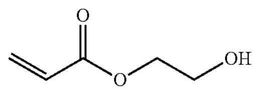 | Free Radical EtOH | 0.01 AIBN, 50-62% quinine | Dialysis, Precipitation (Et$_2$O) | M$_n$ = ~12.000 g/mol PDI = 1.57 | ~22% |
| VAc Vinyl acetate | 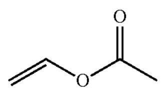 | Free Radical EtOH | 0.01 AIBN, 50% quinine | NA | | ~0% |

An important trend can be gathered from the copolymerizations in Table 1. The comonomers with the highest incorporation of quinine in the copolymer can be arranged in the following order: acrylates (17-20%)>acrylamides (7-14%)>methacrylates (3%)>acetates (0%). At first, it may be surprising that vinyl acetate (VAc) reacts less with quinine than with the other monomers since both of these monomers have fairly electron-rich olefins while the olefins of the other monomers are more electron-poor. Typically, copolymerizations work best with monomers that have similar reactivities. It is thought, but not relied upon that the reactive VAc radical may promote increased proton abstraction of quinine's allylic proton leading to increased degradative chain transfer. A less reactive radical, like MA, may be less prone to abstracting quinine's allylic proton (which would decrease k$_{tr}$), and the more reactive MA monomer may be more easily attacked by a quinine radical (increasing k$_p$ of the cross-propagation). Both of these would lead to higher incorporation of quinine in the MA polymer. The observation that acrylamide (Am) monomers incorporate less quinine than acrylates correlates with the order of monomer reactivity since amide substituents are less electron-withdrawing than ester substituents.[88] Methyl methacrylate is a fairly reactive monomer due to the stabilization of a tertiary radical, but, surprisingly, very little quinine was incorporated in the polymer. This could potentially be explained by steric hindrance between the bulky quinine substituent and the methyl on the β carbon of the methyl methacrylate radical.

Figure 21B:
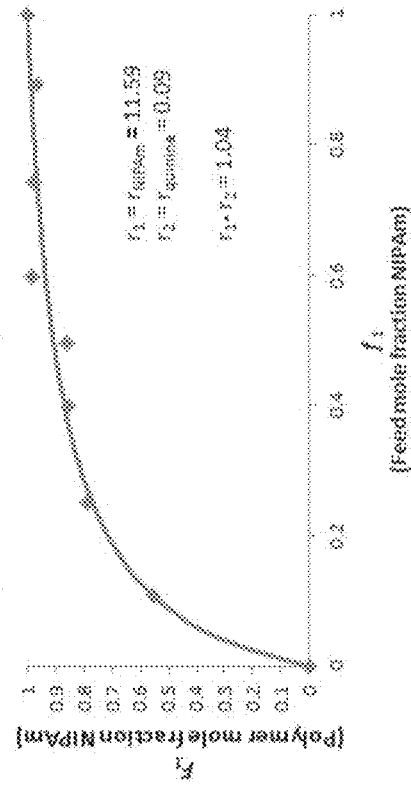
FIGS. 21A and 21B show a comparison of monomer and radical (21A) reactivities of methyl acrylate vs vinyl acetate. 21B) Monomer feed vs polymer composition for the copolymerization of NIPAm and quinine and calculated reactivity ratios using Mayo-Lewis equation.
Figure 21A:
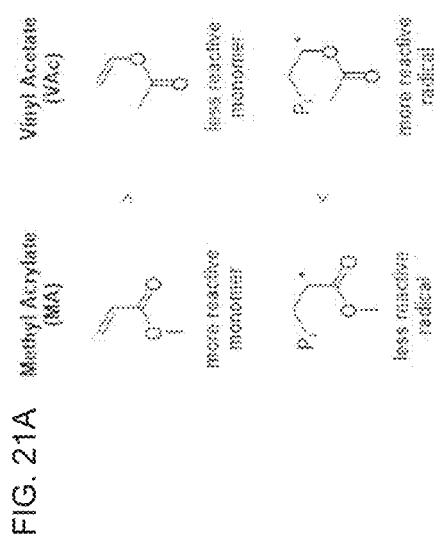

The reactivity ratio for one of the copolymerizations, between NIPAm and quinine, was obtained by monitoring the copolymerization via NMR spectrometry. The monomer consumption was tracked over time and the values for r$_1$ and r$_2$ were calculated with the Mayo-Lewis equation. The non-linear fit gave an r$_1$=r$_{NIPAm}$=11.59, r$_2$=r$_{quinine}$=0.09, and r$_1$r$_2$=1.04 (FIG. 21b). Since r$_1$r$_2$≈1, the copolymerization of quinine and NIPAm is nearly ideal, therefore the copolymer will have quinine distributed statistically along the polymer chain. If larger percentages of quinine in the copolymer are desired for biological applications (such as >20% for an acrylate copolymer), alternative methods, such as the functionalization of the quinine vinyl group could be utilized.

Testing Quinine Copolymers In Vitro

Figure 22B:
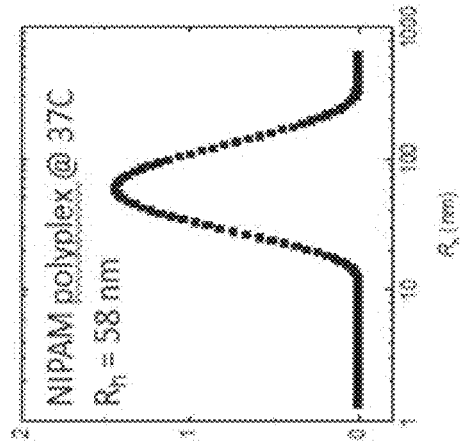
FIGS. 22A and 22B show: 22A) Gel electrophoresis of poly(NIPAM-co-quinine) stained with ethidium bromide and visualized under 366 nm UV light. Shows complete binding of pDNA at N/P=1. 22B) DLS of polyplex made from poly(NIPAm-co-quinine) in $H_2O$ at 37° C. with $D_h$=116 nm.
Figure 22A:
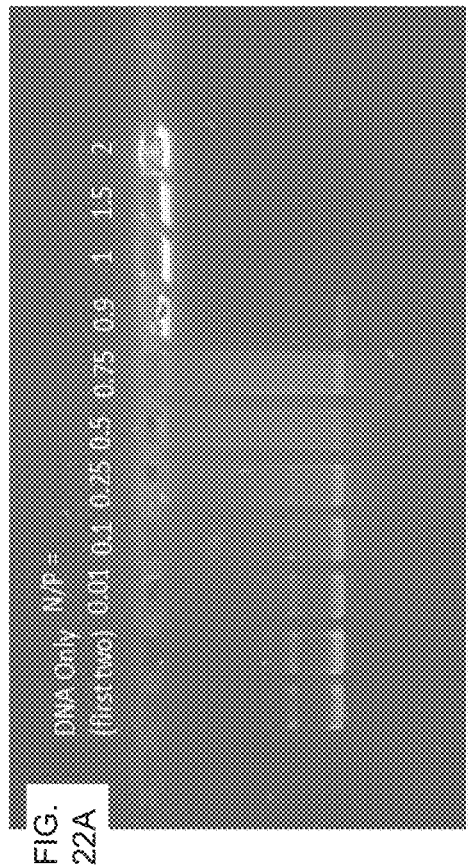

The ability of several quinine copolymers to bind pDNA have been analyzed using the gel electrophoresis assay. As shown by FIG. 22a, poly(NIPAm-co-quinine) completely binds pDNA (stained red with ethidium bromide) at an N/P ratio of 1. Most quinine copolymers show complete binding of pDNA at an N/P ratio between 1-2. FIG. 22a also shows that at N/P ratios>0.75, the blue fluorescence of the quinine copolymer can be seen with excitation by UV light (λ=366 nm). At higher concentrations of polymer, the blue fluorescence allows for visualization of the quinine copolymer actually running in the opposite direction of the DNA, towards the negative electrode. The size of several polyplexes were analyzed in H$_2$O using multi-angle DLS. For example, polyplexes formed by poly(DMA-co-quinine) and poly(NIPAm-co-quinine) (N/P=10) were found to be stable complexes in water with diameters of 150 and 116 nm, respectively. Although this is slightly larger than the goal polyplex size of 100 nm, the size of the polyplexes are significantly smaller than other effective polyplexes utilized.

Several quinine copolymers were tested in vitro in the transfection of HeLa cells with luciferase. No transfection was achieved for NIPAm and DMA copolymers at low N/P ratios (<10), but mild transfection efficiency was seen for HEAm and Am at higher N/P ratios (25-50). Although transfection was mild with the Am copolymer, near 100% of cells had uptake of Cy5-labelled pDNA. In fact, analysis of the HeLa cells 48 hours post-transfection with the wide-field fluorescence microscope showed that the polymer could indeed be visualized by fluorescence (FIG. 23a). The red Cy5 fluorescence appeared colocalized with the blue quinine fluorescence. This experiment shows promise for using quinine in confocal microscopy experiments.

Transfection with the acrylate copolymer poly(HEA-co-acrylate), however, provided more promising results. The HEA copolymer (N/P=7.6) achieved even better transfection efficiency than the Am copolymer with an N/P ratio at 15% that of the Am copolymer. Although the toxicity had not yet been quantified for the HEA copolymer, after qualitative inspection, the polymer appears to be much less toxic than either the Am copolymer or PEI. Transfection studies with the HEA copolymer will continue at higher N/P ratios in hope of achieving transfection efficiency similar to that of PEI while maintaining limited toxicity.

Prophetic Example 2

Synthetic polymer-based transfection reagents may provide a safe, inexpensive, and scalable method to deliver the complex payload necessary for gene editing in target HSPC. In this aim polyplex-mediated delivery of CRISPR/Cpf1 nucleases and ssODN with be systematically evaluated for reporter gene addition in CD34+CD45RA-CD90+ cells from healthy donors. We will compare polyplex-mediated delivery to the current state-of-the-art delivery method (i.e. electroporation). The ideal delivery protocol will maximize reporter gene insertion at the target GSH locus with minimal off-target effects and limit cell death. Performance should be equivalent to, if not better than electroporation.

Although electroporation has been shown to be an effective method for the gene transfer in HSPCs, the method shows significant cytotoxicity (i.e., up to 70% death). Viral vectors can help supplement electroporation for delivery of multiple genetic cargos, but have well-known limitations including genotoxicity due to random integration and limits to scalability for mass production. Polymeric transfection reagents offer several benefits over viruses and electroporation, including improved storage stability, low cytotoxicity and immunogenicity, a significantly reduced cost and ease of mass-production on kg scales. In one scalable synthetic step, the naturally-derived anti-malarial agent quinine has been copolymerized with 2-hydroxyethyl acrylate (HEA), a hydrophilic commoner used for biocompatible materials, to afford a polymer with enhanced transfection efficiency in a variety of cell types (FIG. 2). This new polymer achieves high transfection efficiencies with limited toxicity, likely due to the incorporation of quinine, which promotes endosomal escape and effective intracellular delivery of gene editing cargo. The design of this new polymer has been inspired by previous work demonstrating that addition of quinoline-containing anti-malarials to culture media, such as chloroquine, are known to be lysosomotropic, buffering the pH of the endosomes, which inhibits nuclease degradation and promotes endosomal escape. These small molecule compounds enhance transfection in mesenchymal stem cells and K562 cells. Quinine, which likely works through a similar mechanism, also has well-characterized fluorescent properties (excitation max $\lambda=350$ nm, emission max $\lambda=450$ nm) and endows the polyplexes with fluorescent properties that permit both intracellular trafficking and ex vivo engraftment. This novel polymer will allow for a scalable, tunable, safe, and efficient polymer-based transfection of genetic cargo. Along with transient delivery of plasmids, polymers are now being utilized as vectors in nuclease-based gene editing systems, such as CRISPR-Cas9. Several polymers have been designed for encapsulating and delivering the Cas9-sgRNA complex (ribonucleoprotein) to cells. Co-delivery of the guide RNA (sgRNA), Cas9 protein, and template DNA into the target cell is necessary for successful editing. The most commonly used vehicles in CRISPR-Cas9 editing, such as viral vectors and cationic lipids, must deliver the cargo separately due to limits in their cargo-size capacity [64]. Polymer-based vehicles need not adhere to these size limits and may be utilized to encapsulate both the ribonucleoprotein and template DNA into one package, a "multiplex" (FIGS. 3A, 3B, and 3C). By packaging the material into a single particle, a polymer-based vector may achieve transfection efficiencies comparable to electroporation with or without subsequent viral vector transduction while increasing shelf-life and accessibility, and decreasing the cost of the technology. Here we propose to complex the crRNA, hAsCpf1, and ssODN into one payload with a novel polymer that will enhance the delivery of the components for GSH gene editing and transgene insertion. Complex formation and gene editing will be tested with both crRNA, hAsCpf1 RNA and ssODN combinations and pre-assembled ribonucleoproteins (crRNA and hAsCpf1 protein complexes); the polymer vehicle described herein permits tunable packaging of all editing components.

It is thought, but not relied upon, that disclosed polyplexes carrying all of the required machinery for GSH gene editing and transgene insertion will result in equivalent if not superior performance to electroporation in HSPCs.

Figure 24A:
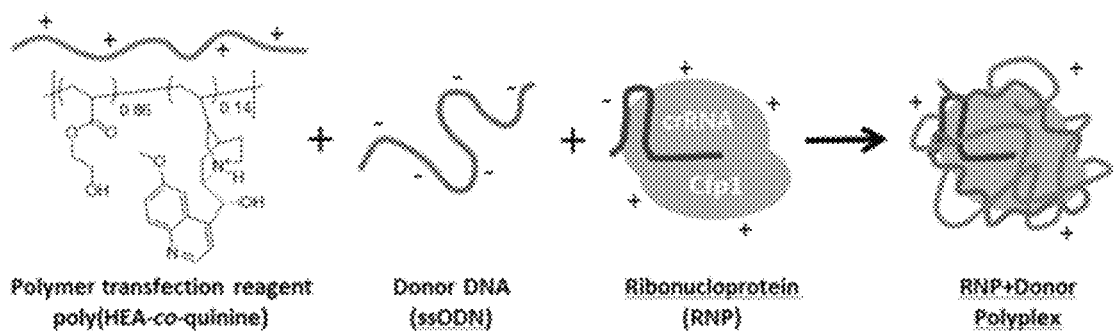
FIGS. 24A, 24B and 24C show: 24A) The chemical structure of the HEA-Q14 copolymer transfection reagent is shown alongside a schematic representing the binding of the RNP and donor DNA together by the cationic polymer to form a polyplex containing all gene editing components. 24B) Delivery of GFP plasmid by the HEA-Q14 polymer to K562 cells shows a statistically significant increase in transfection efficiency from commercial transfection reagents jPEI and Lipofectamine 2000 (p<0.05). 24C) Inset shows wide-field fluorescence microscopy image (20x, DAPI filter) of HEA-Q14 polyplexes (unlabelled) in HeLa cells.
Figure 24B:
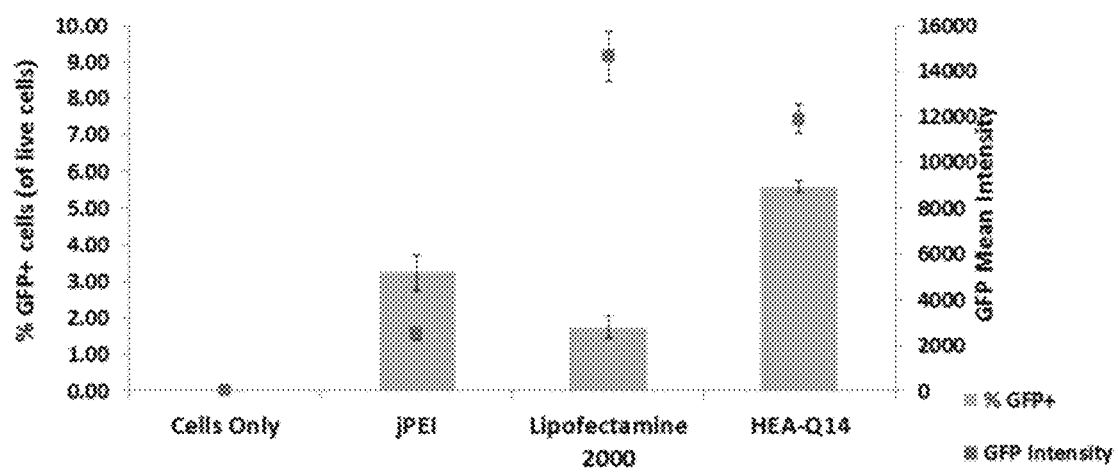
Figure 24C:
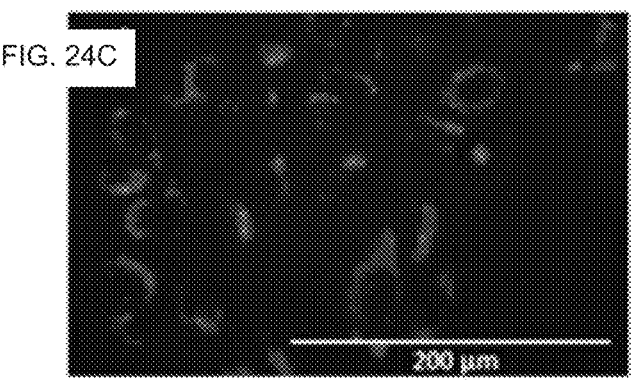

Novel polymer design for improved scalability and transfection efficiency. Our novel polymeric transfection reagent was synthesized via thermally-initiated free-radical copolymerization of HEA with quinine in ethanol. The product, poly(HEA-co-quinine), was isolated and purified by dialysis in a methanol and tetrahydrofuran mixture. Characterization by proton nuclear magnetic resonance spectroscopy (1H-NMR) showed the copolymer contains HEA and quinine in an 86:14 ratio, respectively and is free of residual monomer. The number-average molar mass (Mn) was determined by aqueous gel permeation chromatography (GPC) and was shown to be roughly 12 kg/mol with a dispersity (Đ) of 1.6. The ability of the HEA-quinine copolymer (HEA-Q14) to transfect a variety of cell types with GFP plasmid (4.7 kb) was assessed. By mixing an aqueous plasmid solution (0.02 µg/µL) with an aqueous polymer solution (0.48 µg/µL) at an equal volume ratio, polymer-DNA complexes self-assemble as polyplexes. The size of the polyplexes in water were determined to be 100 nm in diameter by dynamic light scattering (DLS). The polyplex solution is mixed with a serum-free media such as Iscove's Modified Dublecco's Medium (IMDM), added to cells, and left to incubate for 4 hours. Flow cytometry analysis was used to determine the percentage of cells positive for GFP expression and average intensity. A MTT viability assay was performed concurrently to assess toxicity of polyplex formulation. Preliminary transfection studies in HeLa cells and primary dermal fibroblasts (HDFn) showed HEA-Q14 transfected these cells at efficiencies higher than the commercial reagent jetPEI and similarly to Lipofectamine 2000. The uptake of the polymer could be directly imaged with a blue DAPI filter (FIGS. 24A, 24B and 24C). HEA-Q14 was tested in the K562 cell line that models HSPC, which are known to be resistant to nonviral transfection methods. The HEA-Q14 polymer promoted successful transfection two-fold of that found with the commercial vehicle controls, jetPEI and Lipofectamine (FIGS. 24A, 24B and 24C). With minimal optimization, the HEA-Q14 polymer performed equal to or better than formulated commercial reagents.

Formation and optimization of polyplex for gene editing in K562 cells. The gene editing constructs used for the formation of polyplexes are described herein and include crRNA, hAsCpf1, and ssODN. When mixed in according to the procedure described previously, the anionic nucleic acids can complex to the cationic HEA-Q14 polymer to form polyplexes. The relative binding of the polymer to the editing constructs will first be qualitatively determined by gel electrophoresis and visualized by a relevant dye to determine the minimum concentrations needed. The hydrodynamic radii (Rh) of the particles in water and IMDM will be assessed in a highly quantitative manner via DLS on a Brookhaven Instruments BI-200SM multiangle light-scattering instrument according to our published procedures.

Cryogenic transmission electron microscopy (CryoTEM) by a FEI Tecnai G2 Spirit BioTWIN CryoTEM will be used to further characterize morphology of the polyplexes. Zeta potential analysis will be carried out with a Zetasizer Nano ZS from Malvern Instruments to determine surface charge of the particles. This analysis will give insight to the particles size and stability when introduced to cells during transfection. Fluorescent labelling of the components and analysis via flow cytometry and co-localization measurements via confocal fluorescence microscopy will be used to confirm whether all four components are indeed contained within the same multiplex package. Mixing procedure will be optimized to achieve a complexation of all four components. Initial transfection studies will be performed in K562 cells with a Traffic Light Reporter system. Using this system, cells that undergo double-strand break (DSB) repair by nonhomologous end-joining (NHEJ) will express the fluorophore mCherry while cells that undergo homology directed repair (HDR) will express GFP. This system allows for rapid analysis of a variety of transfection conditions using flow cytometry, and will allow for streamlined optimization of the polyplex delivery vehicle for the editing of K562 cells.

Comparing hAsCpf1 RNA vs crRNA/hAsCpf1 RNP delivery in K562 cells. Due to the range of cargo that polymeric vehicles can bind to and deliver, gene editing will be carried out with both hAsCpf1 RNA as well as the hAsCpf1 protein itself. It has been found that nanoparticle-mediated gene editing can be enhanced by delivery of a ribonucleoprotein (RNP: Cpf1 protein pre-complexed with crRNA) versus RNA components. Complexation of RNPs will be performed first, and then both editing components (hAsCpf1:crRNA RNP and ssODN) will be complexed with polymer. Complexes of both compositions will be characterized as described herein. Editing efficiencies will be quantified by the TLR assay as described herein. By fluorescently labeling each construct, and with the inherent fluorescence of the HEA-Q14 polymer, the polyplexes can be tracked within the cell using confocal microscopy. This will allow the determination which intracellular barriers may be limiting gene editing efficiency. Using the information, the polyplex composition can be modified in order to overcome these specific cellular barriers and determine which composition provides the best editing performance with minimal toxicity.

Editing CD34+CD90+CD45RA-HSPC cells with optimized polyplex formulation. Using the crRNAs identified herein and the polyplex formulation found herein, editing on primary CD34+CD90+CD45RA-HSPC from at least three donors of each source tissue (BM and mAPH) type was performed. The transfection efficiency was determined by using GFP expression, Surveyor assay, and BLISS. The toxicity will be determined by MTT assay. The efficiency and toxicity of this method will be compared to the benchmark set by electroporation.

Statistical Analysis and Considerations. IMP Design of Experiments software was used to analyze the relationships between all of the factors in our experiments. Multivariate ANOVA statistical analysis was performed on data for all polyplex formulations as a function of dose, toxicity, editing efficiency. The optimal crRNA, hAsCpf1 and ssODN combination was determined using the methods described herein.

A line of K562 cells have been modified with this system and were used for efficient optimization of polymer complexes for both the RNA and RNP variants. If the benchmark set by electroporation for editing efficiency and toxicity were not met with the HEA-Q14 polymer, other polymers used by our lab for editing, including galactose and trehalose-based polycations, will be tested in the nonviral transfection of the HSPC subgroup. In addition, our group has experience using confocal microscopy to monitor intracellular trafficking of polyplexes in order to identify intracellular barriers and have used novel microfluidic devices to enhance the transfection of stem cells in suspension.

Example 3

Several novel copolymers containing the anti-malarial drug quinine have been directly copolymerized with acrylamide (Am), (2-hydroxyethyl)acrylamide (HEAm), and (2-hydroxyethyl) acrylate (HEA) as well as other monomers through free-radical copolymerization. Of particular importance, the copolymer of (2-hydroxyethyl) acrylate (HEA) showed significant promise as a delivery vehicle of plasmids for transient gene transfection. In addition, our results demonstrates that these polymers are able to simultaneous delivery of three components used for the gene editing with the CRISPR-Cas9 system: Cas9 protein, sgRNA, and plasmid donor.

The quinine copolymers (poly(Am-co-quinine, poly (HEAm-co-quinine, and poly(HEA-co-quinine)) were tested for in vitro for the delivery of GFP (Green Fluorescent Protein) plasmids as a reporter gene for a variety of cell types including HeLa, HEK-293T, K562, and primary dermal fibroblasts (HDFn) and have achieved promising gene expression data in all cell types. We have shown promising gene editing data in the delivery of plasmids and Cas9 protein in an engineered HEK-293T cell line. This cell line has been modified with a Traffic Light Reporter (TLR) system to express either reporter proteins mCherry or GFP depending on whether the cell has undergone nonhomologous end-joining (NHEJ) (expression of mCherry) or homology-directed recombination (HDR) (expression of GFP) with a GFP donor plasmid. Poly(HEA-co-quinine) has shown promising in vitro gene-editing data with this system as analyzed by flow cytometry. The polymer showed increased levels of gene editing while limiting toxicity and cell death to the target cell. K562 cells have been engineered with the same TLR system.

Quinine copolymers, such as poly(HEA-co-quinine), and other potential anti-malarial copolymers, could become broadly used transfection agents for many possible applications. This could be in the delivery of plasmids for transient gene expression to delivery of CRISPR-Cas9 components for gene editing. This could be for non-clinical as well as clinical applications. Our work has been, so far, for in vitro cell modification but the polymer could easily be adapted for ex vivo and in vivo gene delivery for gene therapy applications. In short, this technology could be used very broadly used in many fields of research and for clinical cell and gene therapy.

Figure 25A:
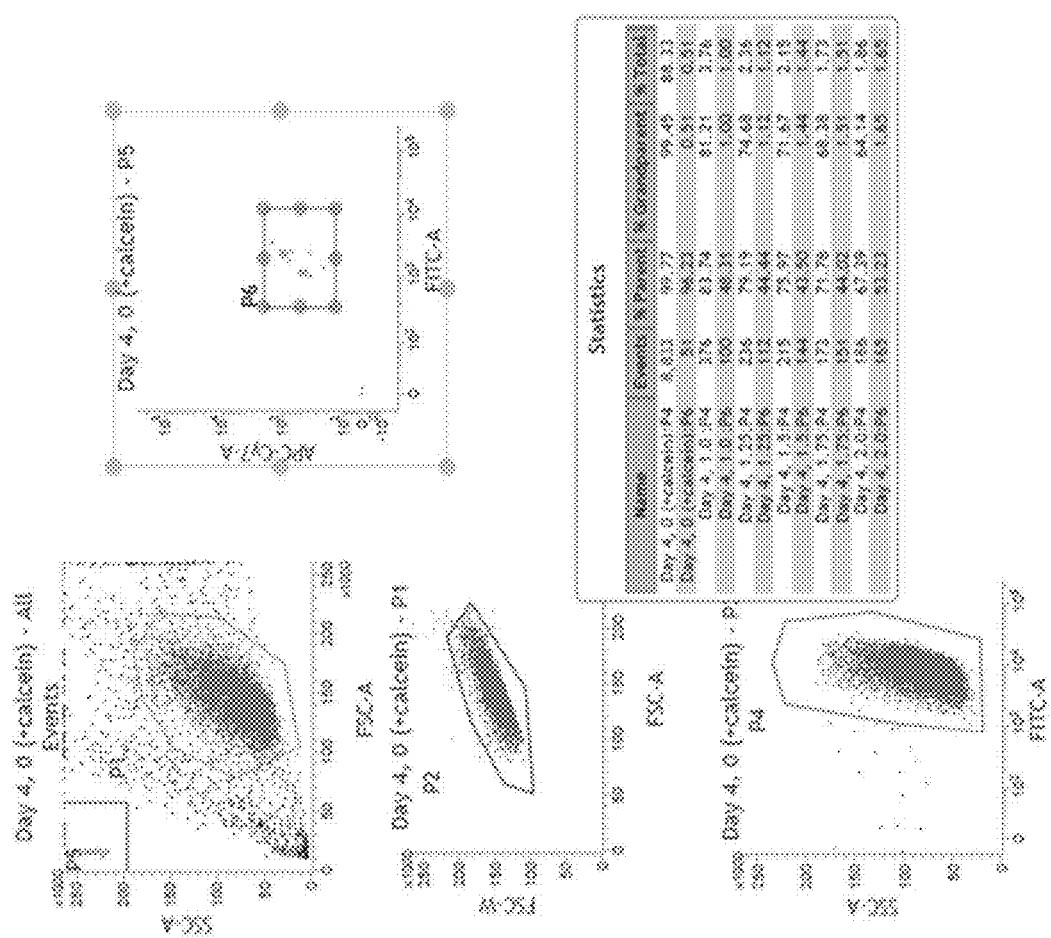
FIGS. 25a and 25b show the results of modifying a K562 cell line with the Traffic Light Reporter system.
Figure 25B:
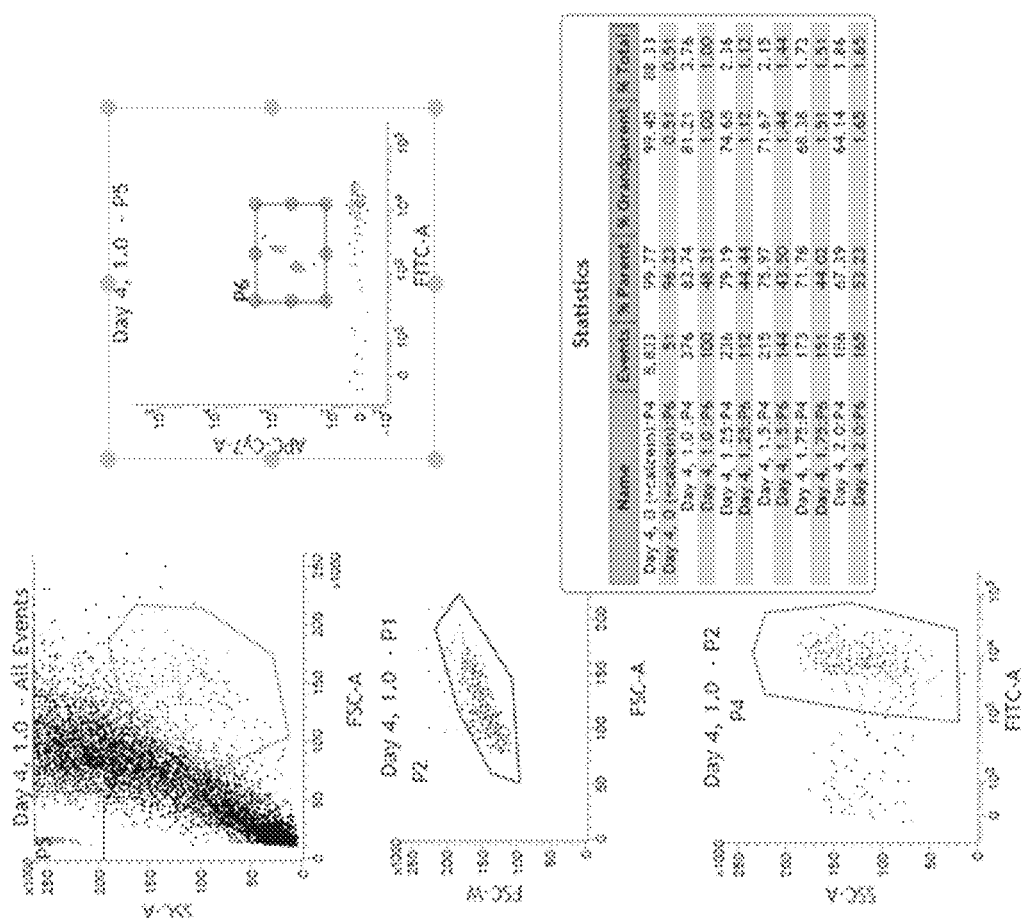

A K562 cell line was modified with the Traffic Light Reporter system. The dose of puromycin necessary to kill most cells within 4-5 days was determined. K562 cells were cultured in gradation of puromycin concentrations of 0, 1.0, 1.25, 1.5, 1.75, 2.0 µg/mL. A calcein viability stain, counting beads, and FACS were utilized to determine % enrichment. The results are shown in FIGS. 25a and 25b.

Figure 26A:
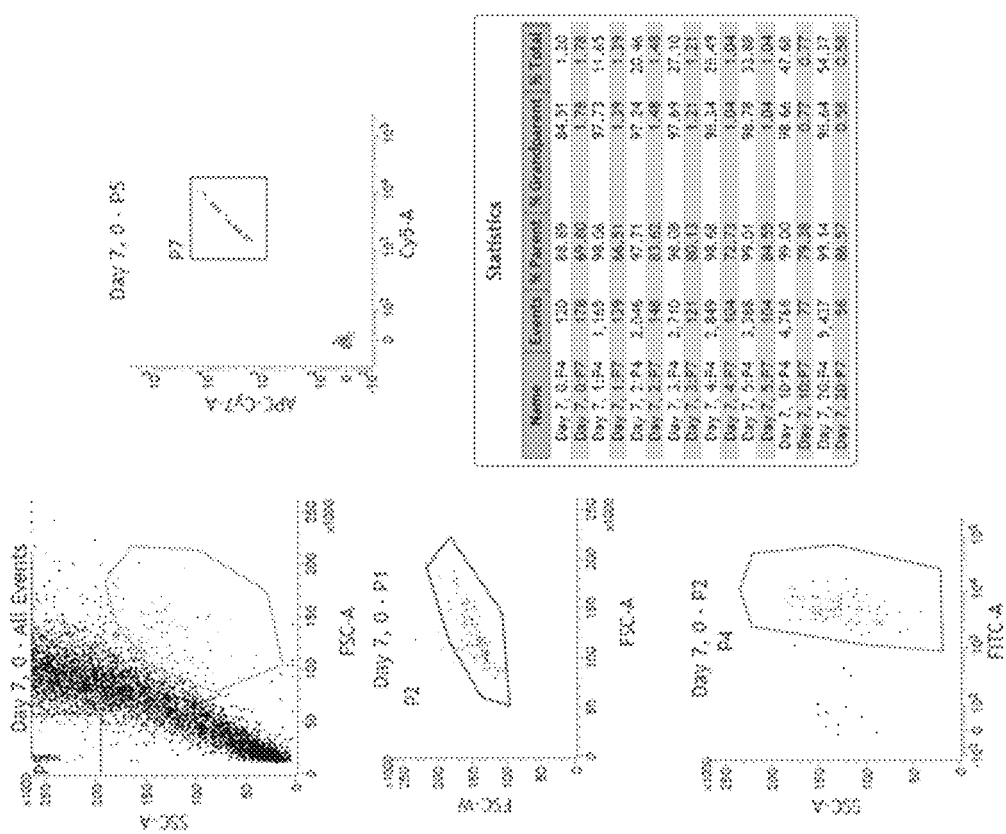
FIGS. 26a and 26b show 7 day, puromycin selection of TLR cells at 0 μL (FIG. 26a) and 1 μL (FIG. 26b) lentivirus plots.
Figure 26B:
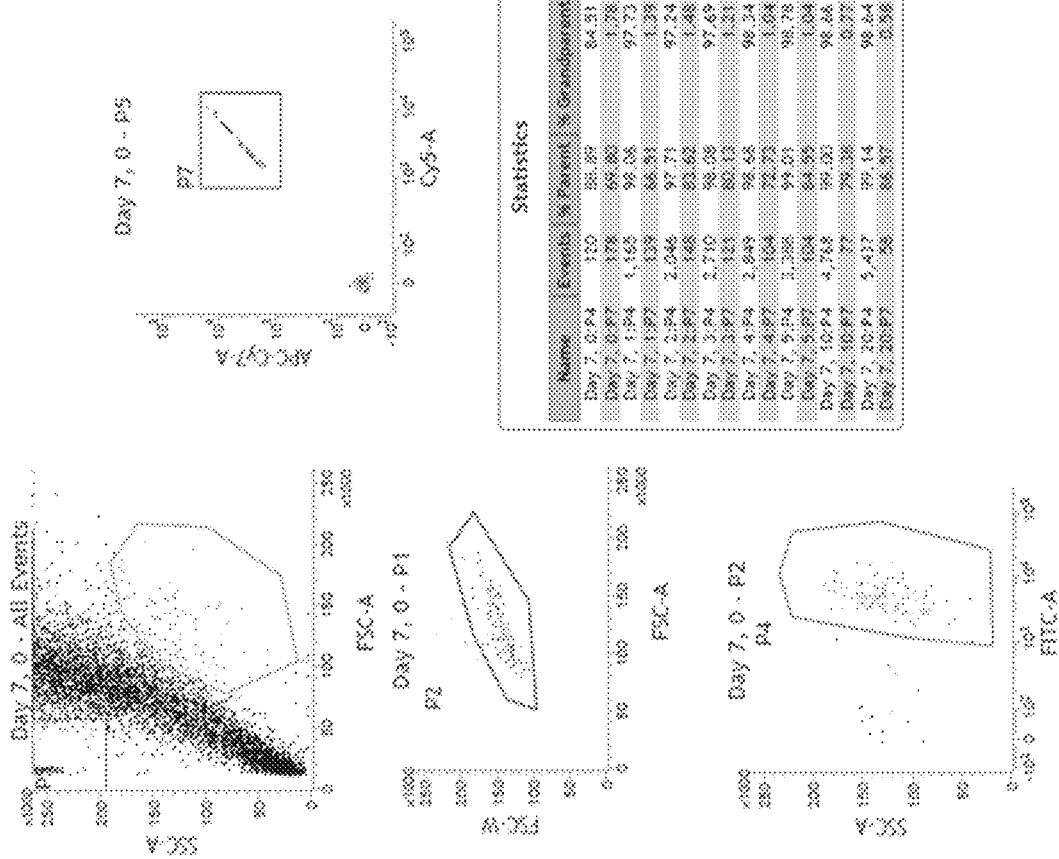

A range (1, 2, 3, 4, 5, 10, 20) of TLR lentivirus to 1.5 million cells/well were added. After 1 week, used calcein viability stain, counting beads, and FACS analysis to determine % enrichment. 12× enrichment of TLR cells between 0 and 1 µL lentivirus after 7 days in 1 µg/mL puromycin. Continued culture 1 more week in 1 ug/mL puromycin for further enrichment (by roughly 1000×) before cryostoring stock. FIGS. 26a and 26b shows the 7 day, puromycin selection of TLR cells at 0 µL and 1 µL lentivirus plots.

GFP Plasmid Transfection in HEK-293T

Figure 27:
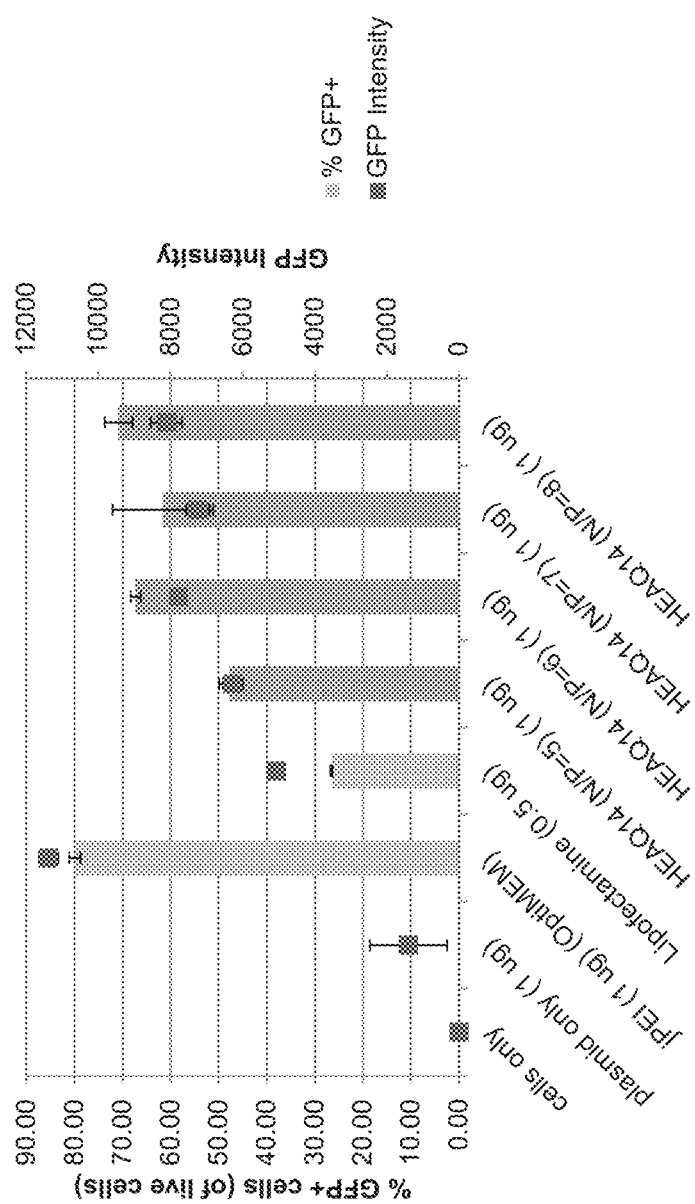
FIG. 27 shows the results of baseline transfection rates for GFP plasmid in HEK-293T cells with HEA-Q14 system.

Baseline transfection rates for GFP plasmid in HEK-293T cells with HEA-Q14 system needed to be established before performing RNP transfection. Controls: Cells only, plasmid only, jPEI, and Lipofectamine 2000. Variables: A-Q14 with N/P ratios of 5, 6, 7, and 8. FIG. 27 shows the results.

RNP Editing with HEAQ14

Figure 28:
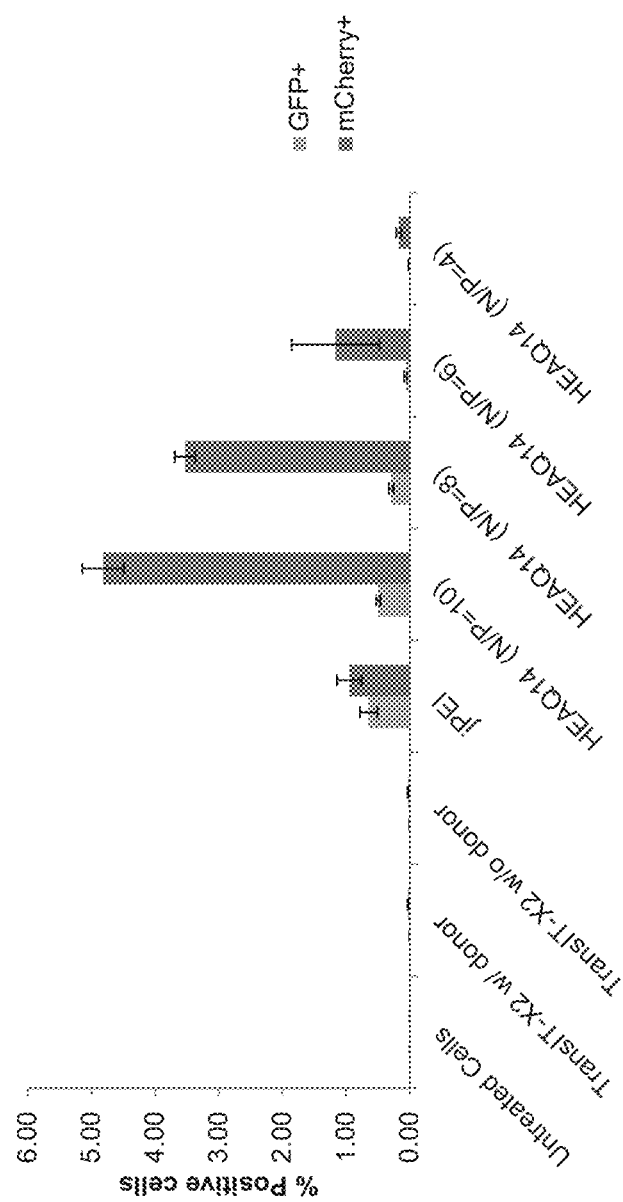
FIG. 28 shows the results of RNP Editing with HEAQ14.

Positive Controls: TransIT-X2 w/ donor (ssDNA); TransIT-X2 w/o donor→to just have mCherry+ cells for compensation; JetPEI Experimental Samples: HEA Q14: N/P=10, 8, 6, 4; Ratio of Cas9:sgRNA:ssDNA; Mass ratio→1:0.25:1; Molar ratio→1:3:1; Dose: Total nucleic acid concentration in nucleic acid/RNP solution equal to 20 µg/µL; Same concentration as transient plasmid transfections. FIG. 28 shows the results and Table 2 shows the tabulated results

TABLE 2

Estimated Total Level of Editing

| Sample | HDR | NHEJ | Total |
|---|---|---|---|
| Untreated Cells | 0.0 | 0.0 | 0.0 |
| *TransIT-X2 w/donor | 0.0 | 0.1 | 0.1 |
| *TransIT-X2 w/o donor | 0.0 | 0.1 | 0.1 |
| jPEI | 0.6 | 2.9 | 3.5 |
| HEAQ14 (N/P = 10) | 0.5 | 14.5 | 14.9 |
| HEAQ14 (N/P = 8) | 0.3 | 10.6 | 10.9 |
| HEAQ14 (N/P = 6) | 0.1 | 3.5 | 3.6 |
| HEAQ14 (N/P = 4) | 0.0 | 0.5 | 0.5 |

The level of edited cells could be approximated by assuming the mCherry+ cells only represent ⅓ of indel formation events. This is a rough estimate though and the true number can only be actually determined through high-throughput sequencing Overall, saw higher levels of total editing with HEAQ14 compared to jPEI. The level of HDR, however, for HEAQ14 was low—This may be due to incompatibilities of the ssDNA donor with the HEAQ14 polymer; This is consistent with what was seen with mRNA and what has been previously observed with other cationic polymers.

Editing efficiencies correlate with N/P ratio. Although no toxicity assay was performed, a qualitative examination showed that both jPEI and HEAQ10 had comparably high toxicities—HEAQ14 N/P=6 appeared to be much less toxic; Need to perform toxicity assay in future experiments.

Plasmid Editing with HEAQ14

The amount of editing that could be achieved by using plasmids for Cas9, sgRNA, and donor was desired to be known. Better compensation controls were needed for proper analysis—Untreated→Untreated; Calcein Violet→Calcein Violet+; jPEI w/pZsGreen→GFP+; HEAQ14 w/ LacZ→HEAQ14+; jPEI w/o donor→mCherry.

Experimental samples: Lipofectamine; jPEI; HEAQ14 (N/P=6) (at three different doses) Ratio of Plasmids→Cas9: sgRNA:Donor—Mass ratio→1:1:1

Plasmid concentration: Total plasmid concentration equal to 20 µg/µL—Same concentration as transient plasmid transfections and same nucleic acid concentration as RNP transfection Dose of jetPEI=0.667 µg of each plasmid—Total plasmid dose=3*0.667 µg per well; this was chose because it had been determined previously that this was the optimal dose for jPEI; HEAQ14 dose ranges between 3*1 µg, 3*0.667 µg, and 3*0.333 µg.

Formulation—Mixed all three plasmid together before mixing with transfection reagent; Formulated complexes in Opti-MEM for lipofectamine; and Formulated complexes in water for jPEI and HEAQ14

Figure 29:
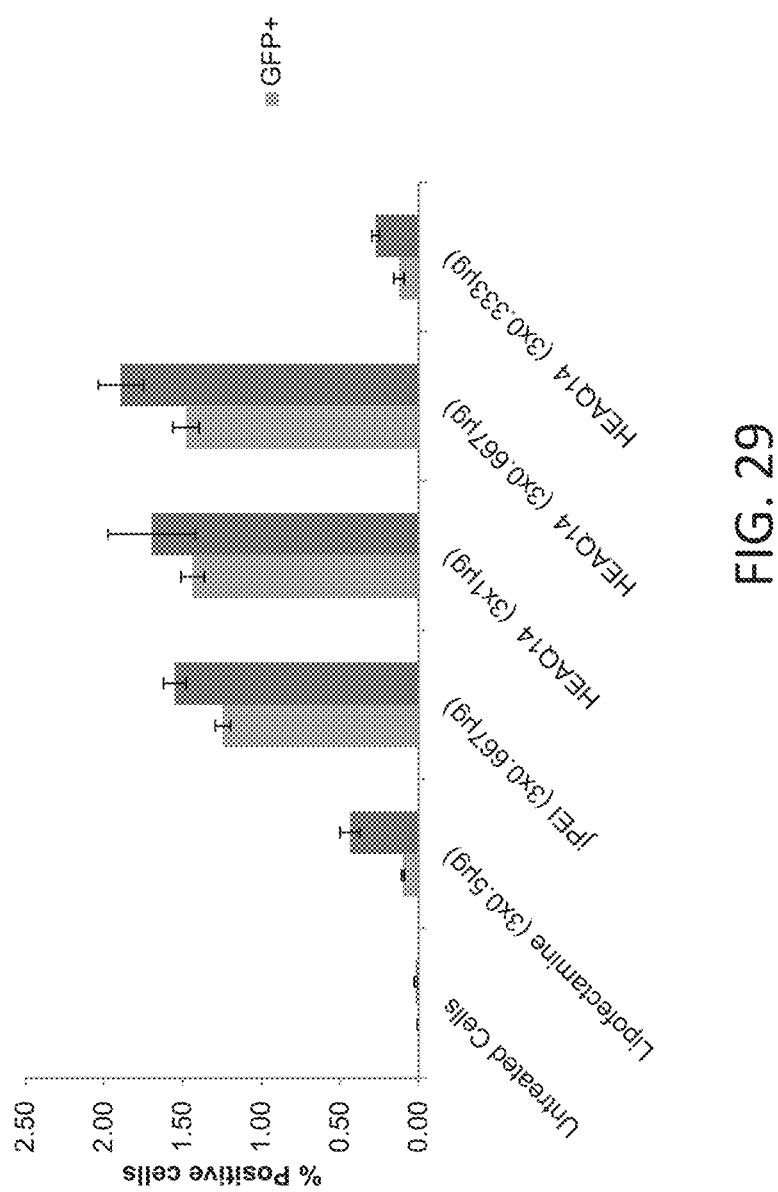
FIG. 29 shows the results of Plasmid Editing with HEAQ14.

A 4 hour transfection period was utilized and the samples were analyzed after 72 hours. The results are shown in FIG. 29 and Table 3.

TABLE 3

Estimated Total Percent Edited Cells

| Sample | HDR | NHEJ | Total |
|---|---|---|---|
| Untreated Cells | 0.0 | 0.0 | 0.1 |
| Lipofectamine (3 × 0.5 µg) | 0.1 | 1.3 | 1.4 |
| jPEI (3 × 0.667 µg) | 1.2 | 4.7 | 5.9 |
| HEAQ14 (3 × 1 µg) | 1.4 | 5.1 | 6.5 |
| HEAQ14 (3 × 0.667 µg) | 1.5 | 5.7 | 7.2 |
| HEAQ14 (3 × 0.333 µg) | 0.1 | 0.8 | 0.9 |

The results were similar to those above—the level of edited cells could be approximated by assuming the mCherry+ cells only represent ⅓ of indel formation events. This is a rough estimate though and the true number can only be actually determined through high-throughput sequencing.

Achieved a statistically significant increase in HDR from jPEI to HEAQ14 with the same dose. No toxicity assay was performed, but toxicity seemed fairly low for HEAQ14 complexes compared to JetPEI and lipofectamine. An MTT assay will be done concurrently.

Example 4

Figure 30A:
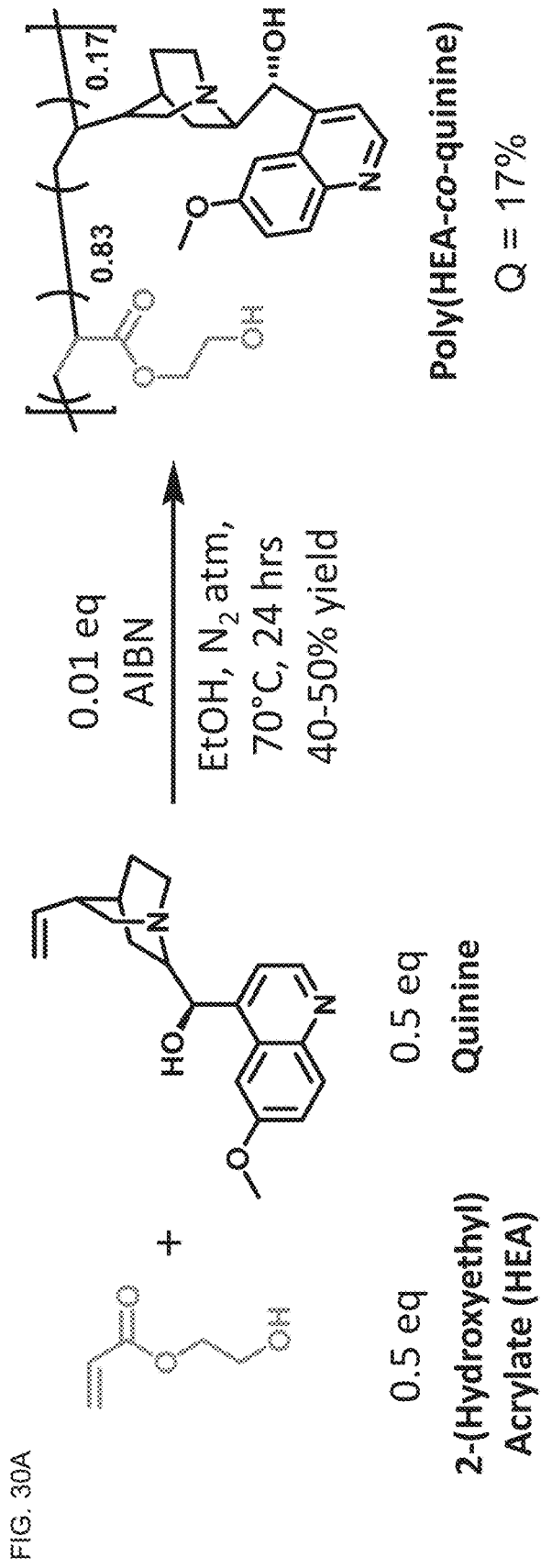
FIGS. 30A and 30B show: 30A) Reaction scheme showing the conditions used for the free radical copolymerization of HEA and quinine with a 50/50 monomer feed ratio. 30B) Other acrylates and acrylamides were reacted at 50/50 feed ratios and showed a range of quinine incorporation (%) in the final isolated polymer as determined by H-NMR.
Figure 30B:
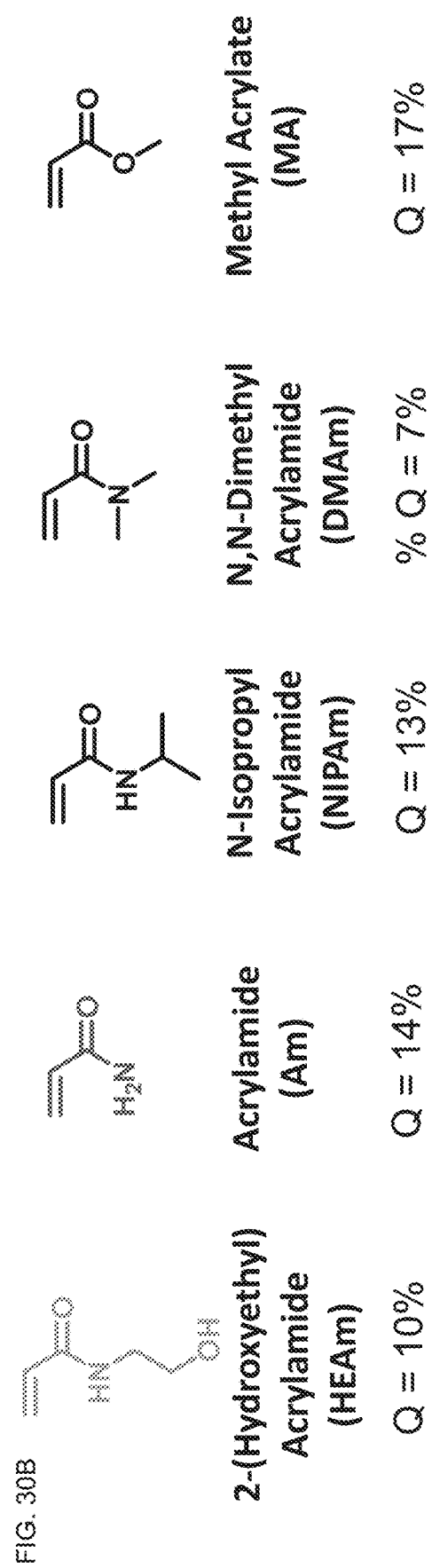

It has been shown, that quinine will undergo copolymerization with acrylonitrile and n-vinylpyrrolidone when reacted with AIBN. This simple, one-step, industrially-friendly method was used to copolymerize quinine with a variety of acrylamides and acrylates (FIG. 30) with purification performed by either dialysis or precipitation. Depending on the comonomer, when quinine constituted 50% of the monomer feedstock, roughly 7-17% incorporation of quinine as quantified by $^1$H-NMR was observed. The molar masses ($M_n$) of the polymers ranged between 8-22 kDa as measured by SEC (Table 4). One can see that quinine was indeed incorporated within the copolymer (and not present as a homopolymer mixture) by observing that the single peak observed by refractive index and light scattering detectors of the SEC was also UV active ($\lambda$=311 nm) due to the incorporation of quinine (FIG. 35). Although significant incorporation of quinine was achieved with acrylamides and acrylates, incorporation of quinine in the copolymerization with vinyl acetate or methyl methacrylate was negligible. Possible explanations include increased allylic hydrogen abstraction by the more reactive vinyl acetate propagating radical and perhaps steric hindrance caused by the β-methyl of the methyl methacrylate.

TABLE 4

Properties of Quinine Copolymers and Analogues

| Polymer | ID | % Cationic Repeat Unit in Polymer | % Cationic Monomer in Feed | Mn (kg/mol) | Đ |
|---|---|---|---|---|---|
| poly(HEA-co-quinine) | HEAQ14 | 13.7 | 40 | 22 | 1.76 |
| poly(Am-co-quinine) | AmQ14 | 14.3 | 50 | 9.2 | 1.39 |
| poly(HEAm-co-quinine) | HEAmQ14 | 13.6 | 60 | 8.8 | 1.38 |
| poly(HEA) | poly(HEA) | 0 | 0 | 25 | 2.47 |
| poly(Am) | poly(Am) | 0 | 0 | 5.8 | 1.85 |
| poly(HEAm) | poly(HEAm) | 0 | 0 | 8.9 | 1.39 |
| poly(HEA-co-DMAEMA) | HEA-DMAEMA13 | 13.0 | 14 | 19 | 2.17 |
| poly(HEA-co-DMAEAm) | HEA-DMAEAm14 | 14.3 | 12 | 38 | 2.05 |
| poly(DMAEMA)* | P(DMAEMA) | 100 | 100 | 11.3 | 1.02 |

Figure 36:
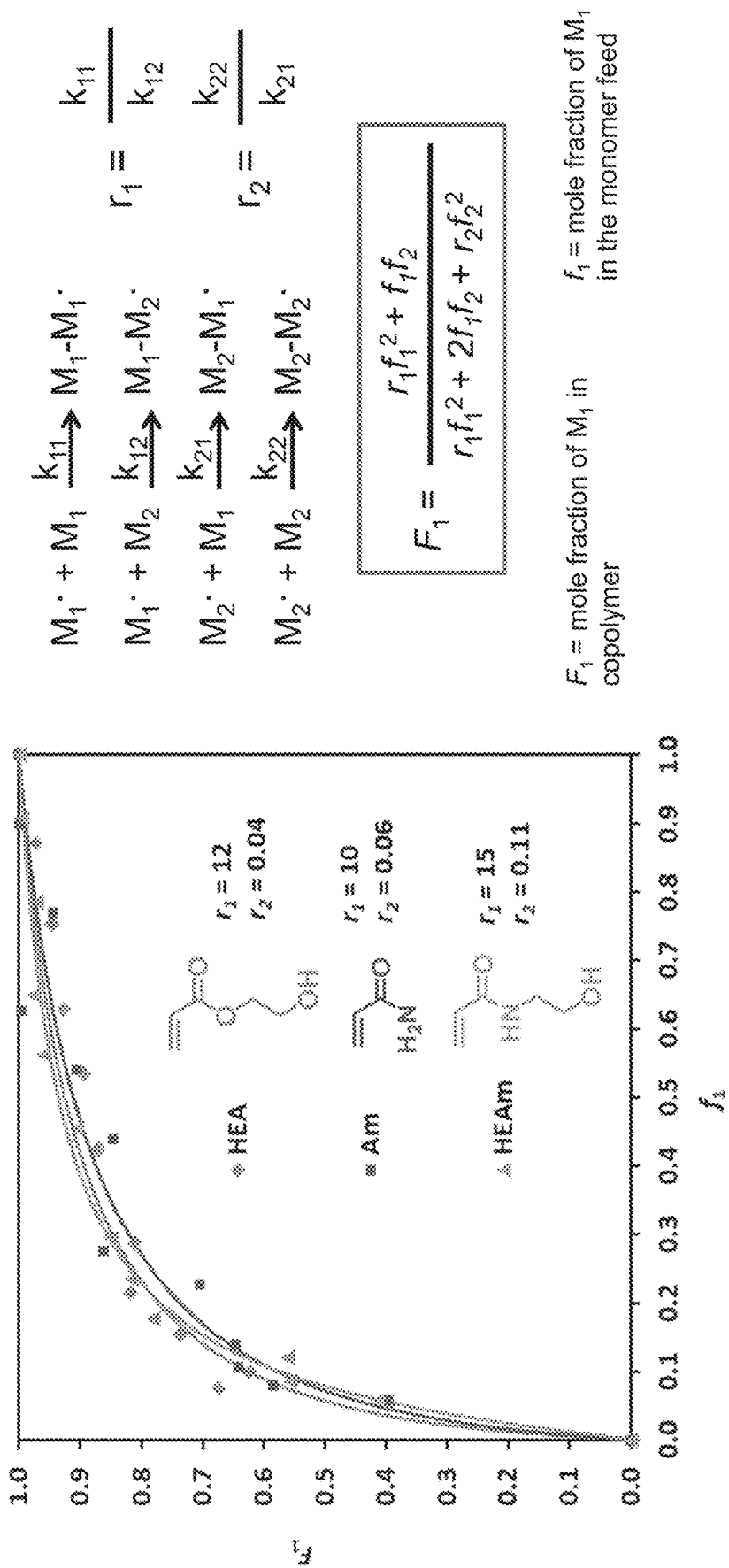
FIG. 36 shows a reactivity ratio plot of the free-radical copolymerization of quinine and three hydrophilic comonomers (HEA, Am, and HEAm). The copolymerization for each comonomer was performed at 70° C. in deuterated DMSO by variable temp (VT) H-NMR. The fraction of hydrophilic comonomer in the copolymer ($F_1$) was determined by the amount of conversion of the hydrophilic comonomer and quinine. The monomer conversion was determined by monitoring the reduction in each monomer's corresponding alkene proton peaks. The conversion of each comonomer was determined for when the total monomer conversion reached 8%. The fraction of hydrophilic comonomer in the starting monomer feed ($f_1$) was determined by taking ratio of comonomers' alkene proton peaks at t=0. The points for each reaction were fitted with the Mayo-Lewis copolymerization equation in order to determine $r_1$ and $r_2$ for each comonomer pair (where $M_1$ is the hydrophilic comonomer and $M_2$ is quinine).

In order to determine the microarchitecture of the acrylate- and acrylamide-quinine copolymers, the reactivity ratios between quinine and three different comonomers were determined by H-NMR analysis. The three comonomers examined were 2-hydroxyethyl acrylate (HEA), 2-hydroxyethyl acrylamide (HEAm), an acrylamide (Am) due to their initial success in biological screenings as well as their similarities in structure (Table 4). By comparing HEA with HEAm, the role of the activating group (ie acrylate vs acrylamide) could be determined in its reactivity with quinine. By comparing HEAm with Am, the role of the pendant group could be determined. For the free radical copolymerization of each comonomer with quinine, fitting with the Mayo-Lewis method to give reactivity ratios where $r_1$=10-15 and $r_2$=0.04-0.11 (FIG. 36). These numbers show that for each hydrophilic comonomer (HEA, HEAm, and Am), propagating radical chain-ends consisting of either the comonomer and quinine greatly prefer to react with alkene of the hydrophilic comonomer over the alkene of quinine. This result showed that quinine will only be incorporated sparingly throughout the polymer in a statistical fashion at these low conversions. Any differences in reactivity attributed to activating groups or the pendant hydroxyl group was indiscernible at this extreme reactivity disparity. The reactions to form disclosed polymers can run over the course of 24 hr, though, to obtain near full conversion of the hydrophilic comonomer. As the reaction consumes more of the reactive comonomer, a shift in comonomer feed occurs that allows for greater quinine incorporation in the later stages of the reaction. This monomer feed drift inevitably leads to a gradient between chains, and the final quinine percentage in the isolated product is represented as the average incorporation amongst all chains.

A series of HEA-quinine copolymers were synthesized with varying monomer feed ratios (0-50% quinine) that yielded copolymers with percentages between 0-17%. The resulting percentage in the purified product had a linear dependence on the percentage of quinine in the monomer feed (FIG. 37). A series of polymers containing the tertiary amine monomers, 2-(dimethylamino)ethyl methacrylate (DMAEMA) and 2-(dimethylamino)ethyl acrylamide (DMAEAm), were synthesized in order to serve as controls in biological studies (Table 4). DMAEMA has been widely used in the field for making cationic polymers capable of binding and delivering DNA. Tertiary amines were utilized since quinine also contains a tertiary amine. Attempts to synthesize the acrylate analogue, 2-(dimethylamino)ethyl acrylate (DMAEA), yielded polymers too prone to degradation due to self-catalyzed hydrolysis. Both DMAEMA and DMAEAm were copolymerized with HEA by free-radical copolymerization to afford polymers with roughly the same percentage of tertiary amines and similar molar masses and dispersities as HEAQ14. A homopolymer of DMAEMA (Table 4), which is a commonly-used block structure of this cationic amine moiety, was also synthesized to serve as a control. Poly(DMAEMA) was synthesized via radical addition-fragmentation chain-transfer (RAFT) polymerization with the chain-transfer agent 4-cyano-4-[(dodecylsulfanylthiocarbonyl)sulfanyl]pentanoic acid (CDP) to form a monodisperse sample that is similar to other DMAEMA blocks used in polymeric transfection reagents. By comparing the performance of these simple tertiary amine polymers to the HEAQ14 polymer, the effect of replacing a standard tertiary amine with quinine in a polymer to enhance transfection could be assessed.

Although it is unusual to perform free radical copolymerization between monomers of such significant differences in reactivity, this disclosure shows that it is possible to yield significant incorporation of an unreactive monomer into a polymer that is not amenable towards free radical homopolymerization. It is a mild and scalable synthesis with cheap, commercially-available reagents. Although the overall yield of the polymer is limited to due to the unreactivity of the quinine, alternatives to the batch reactor utilized here (such as a continuous process reactor) could greatly increase the yield. Among the limitations of any free radical polymerization, however, is the lack of control of the molar mass and dispersity. For purposes of this disclosure, though, free radical copolymerization yielded polymers that were able to bind strongly with DNA with distributions similar to other polymeric gene delivery vectors.

DNA Binding and Polyplex Formation

Figure 31:
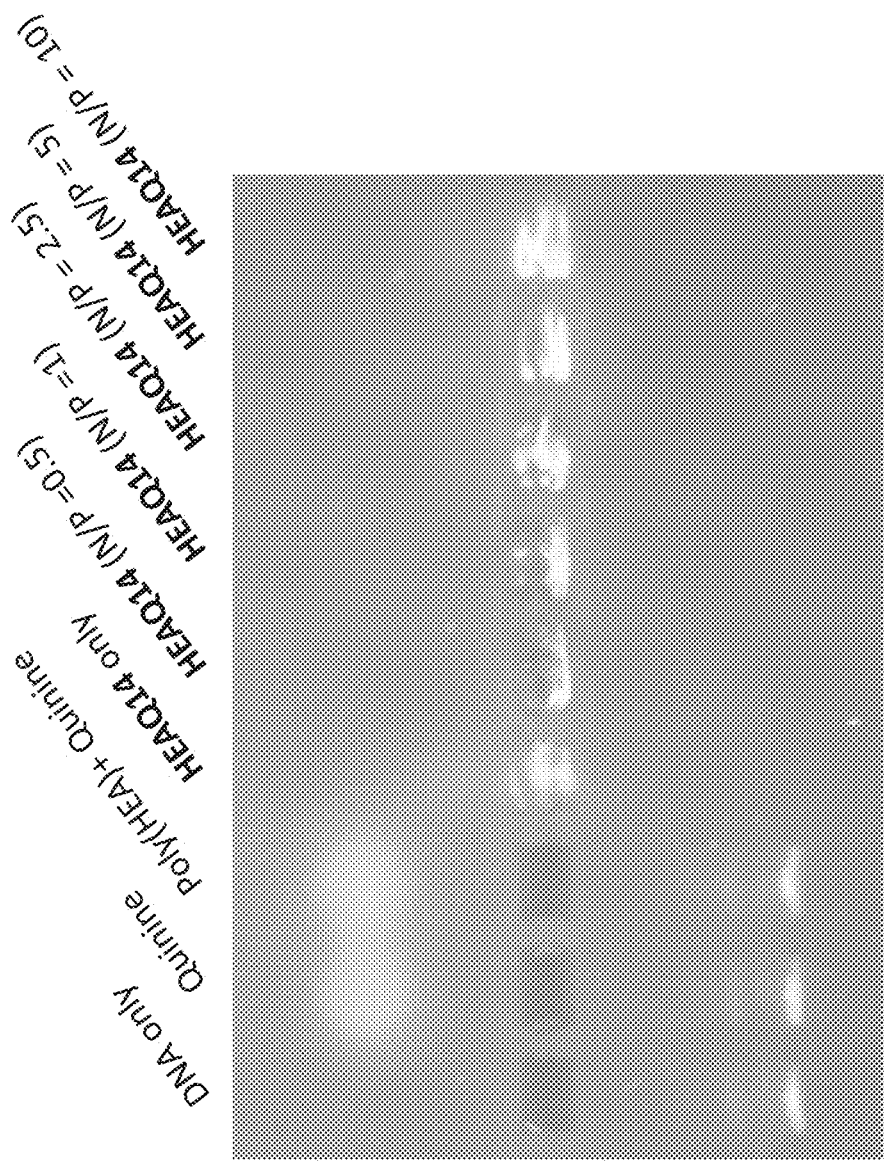
FIG. 31 shows a gel shift assay showing binding ability plasmid DNA (4.7 kb) to be bound by free quinine, HEA homopolymer w/ free quinine, and HEA-quinine copolymer (HEAQ14) at a range of N/P ratios to bind. The agarose gel formed with Tris-acetate-EDTA buffer (pH=8) is stained with ethidium bromide and illuminated with near-UV light.

Upon a slow addition of an aqueous polymer solution to an aqueous DNA solution (0.02 µg/µL) at a 1:1 v/v ratio, the polymer and DNA self-assemble to form polyplexes. The target concentration of the polymer in the polyplex solution was determined by the target N/P ratio which is the molar ratio of cationic amine groups on the polymer (N) to anionic phosphate groups of the DNA backbone (P). For the disclosed system, only quinine's tertiary amine was considered in the N/P calculation since it is the only amine with significant protonation at neutral pH. The HEA-quinine copolymer showed limited solubility at a neutral pH, however, so the solution was acidified with acetic acid (0.509M, pH~4) to solubilize the polymer. Therefore, the polymer/DNA solution (at 0.01 µg/µL) was also acidic until diluted by a buffered media before introduction to cells. In order to gauge the polymer's binding affinity with plasmid DNA, a gel shift assay was performed with the HEA-quinine copolymer with 14% quinine (named HEAQ14). Upon successful binding and charge neutralization of the DNA, the migration of the DNA with the electrophoretic field was inhibited. HEAQ14 fully bound the plasmid at an N/P=1. The first three lanes in FIG. 31 shows inability of the homopolymer p(HEA), quinine, and a mixture of quinine and p(HEA) (at equivalent molar ratios to HEA-quinine copolymer) to bind DNA. Strong binding is only present when quinine is incorporated within the polymer. Since the cationic components of this gel are UV-fluorescent, we have the unique ability to visualize unbound quinine and quinine copolymer migrating towards the positive electrode. At higher N/Ps for the quinine copolymer and polymer only samples, a blue smear shows the migration of unbound polymer that is present in excess at N/P ratios greater than one.

Figure 38:
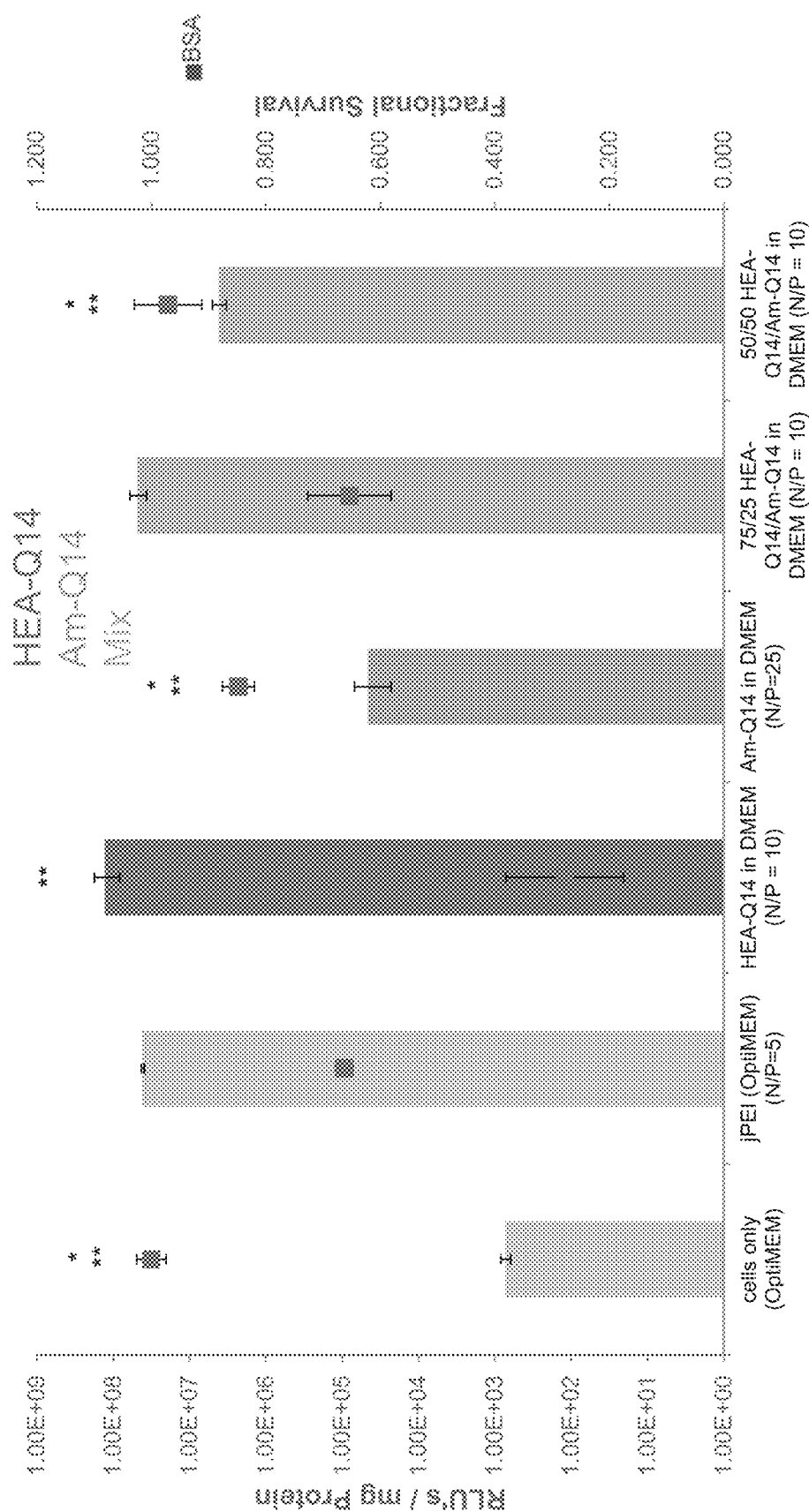
FIG. 38 shows luciferase transfection with HeLa cells comparing HEA-, Am-, and HEAm-quinine copolymers.

The HEAm-quinine copolymer (10% quinine) and Am-quinine copolymer (14% quinine) also showed binding of plasmid DNA at an N/P=1 and 2, respectively. Preliminary transfection screenings were performed in order to determine which copolymer showed the most promise as a transfection vehicle. Using a luciferase reporter plasmid, transfection in HeLa cells showed that the HEA-quinine copolymer showed significantly higher expression of luciferase (FIG. 38). We, therefore, focused on the HEA-quinine copolymer for optimization studies. In order to determine which percentage of quinine in the copolymer was optimal for transfection, a series of HEA-quinine copolymers ranging in quinine composition (between 0-17%) were brought through a luciferase transfection assay in HeLa cells (FIG. 39). The copolymer with 14% quinine showed the highest level of expression and was, therefore, the focus of our optimization and analysis.

The sizes of the HEAQ14 polyplexes in aqueous media were analyzed via dynamic light scattering (DLS). At an N/P ratio=1, the particles had a hydrodynamic diameter of 200 nm (FIG. 40). As the N/P ratio increased, we saw a general decrease in the hydrodynamic diameter with a minimum diameter of 80 nm at N/P=6. This shows that increasing the N/P ratio allows for increased compaction of the particles containing DNA. Zeta potential measurements showed at the N/P ratio of 6 (chosen for is optimal transfection properties), the particles had a positive surface charge (+30 mV) and were colloidally stable. Upon dilution (3×) in a buffered cell media such as Dulbecco's Modified Eagle Medium (DMEM) without serum, however, significant aggregation of the particles occurred. The particles became large enough to quickly settle on the well bottom and be visualized directly by widefield microscopy (FIG. 41). At all N/P ratios, with or without DNA, particles formed that were between 1-2 μm in diameter and showed a propensity for increased aggregation over time. When DMEM is supplemented with protein, by the addition of fetal bovine serum (FBS) at 10% v/v, however, aggregation is inhibited and particle sizes remain under 250 nm (FIG. 40). Even media that contains small concentrations of protein such as OptiMEM (which contains some insulin and transferrin) shows reduced aggregation (FIG. 42). The more aggregation is reduced by the presence of protein, the less able the polymer is to promote transfection (FIG. 43).

When DMEM (without FBS) is used to dilute the polyplexes prior to transfection, aggregation occurs can occur even without DNA present. The DNA, however, remains bound within the aggregates as shown by a dye exclusion assay with ethidium bromide (FIG. 44). In the presence of free DNA, ethidium bromide intercalates within the DNA its fluorescence is greatly increased. When the DNA is bound by a cationic polymer, a fraction of the dye is excluded from intercalating with DNA leading to a decrease in fluorescence. Therefore, the amount of dye excluded can give insight to how much of the DNA is bound by polymer. At an N/P=5, a significant fraction of DNA is bound by polymer. This N/P corresponds to minimum N/P necessary to see significant levels of transfection in the transfection assays. This shows that DNA is indeed bound in the aggregates that form in the presence of DMEM (without FBS) at N/P ratios of 5 or higher.

Upon dilution in buffered cell media, the fraction of protonated quinoline nitrogens and tertiary amines in the solvated HEA-quinine copolymer are significantly reduced. As the surface potential of the polyplexes is reduced, aggregation occurs rapidly due to the presence of hydrophobic quinine pendant groups. Despite the decrease in electrostatic potential between the DNA and polymer, a significant fraction of DNA remains bound to the polymer at N/P ratios of 5 or higher. Although the zeta potential of these particles are near 0 for these particles, the DNA remains bound potentially due to the DNA-binding properties shown in our previous work. This intercalation-based DNA binding in a hydrophobic particle is unique among polymeric transfection agents. A disadvantage of this type of DNA binding is the lack of stability to protein in cell media if protein is required during the transfection protocol. The ability of protein to bind and disassemble the polyplex may facilitate unpackaging of the DNA by the intracellular milieu which may allow for the copolymer to overcome this critical barrier for facile expression of genetic cargo.

Transient Transfection

Figure 32A:
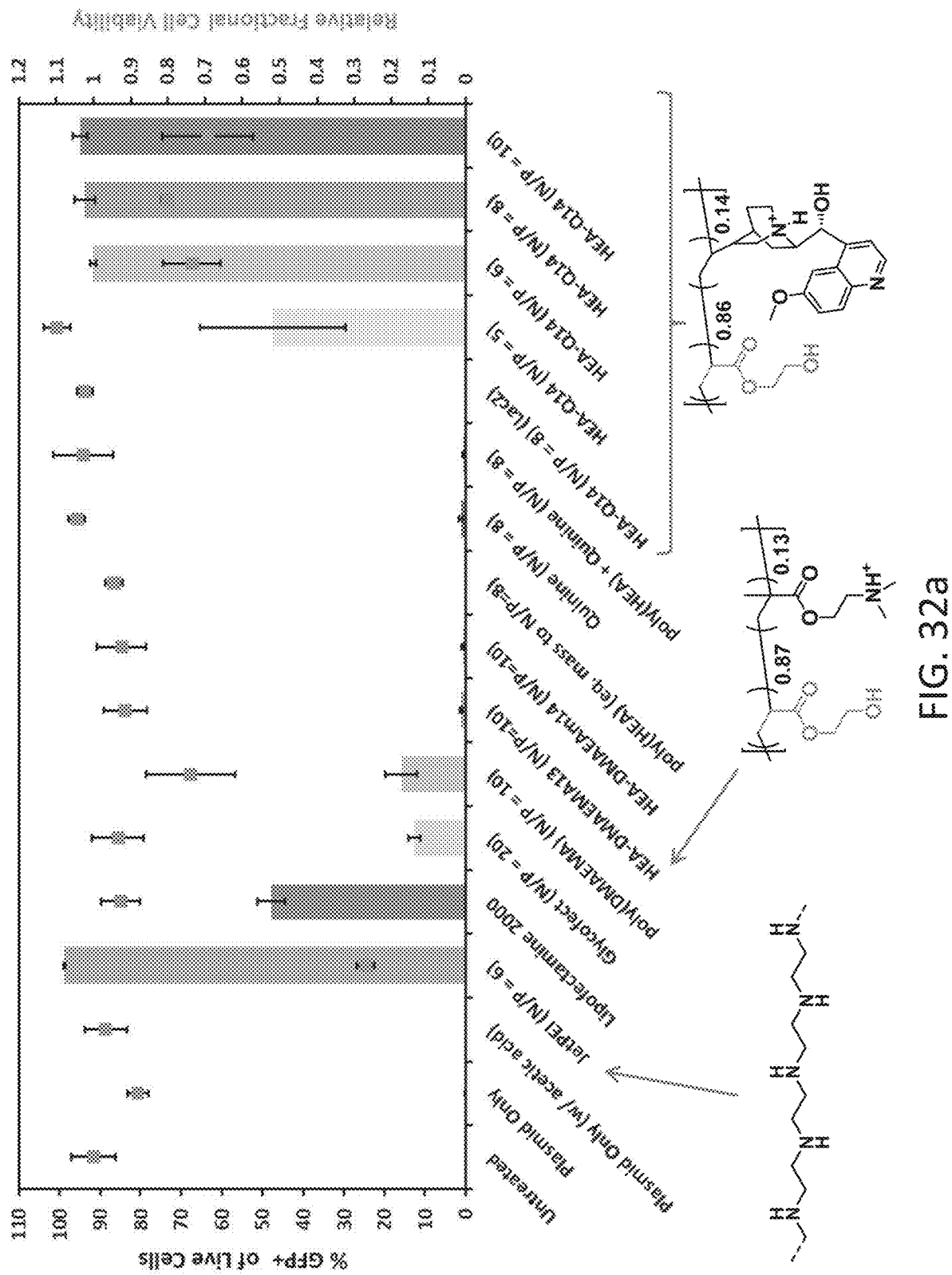
FIG. 32a shows a transient transfection of HEK-293T cells with GFP (ZsGreen) after 48 hrs as quantified by flow cytometry. Bars (left y-axis) show percentage of live cells expressing GFP that were also negative for cell death marker, propidium iodide. Dots (right y-axis) correspond to relative fraction of viable cells in sample as compared to the untreated sample as determined by the CCK-8 viability assay.
Figure 32B:
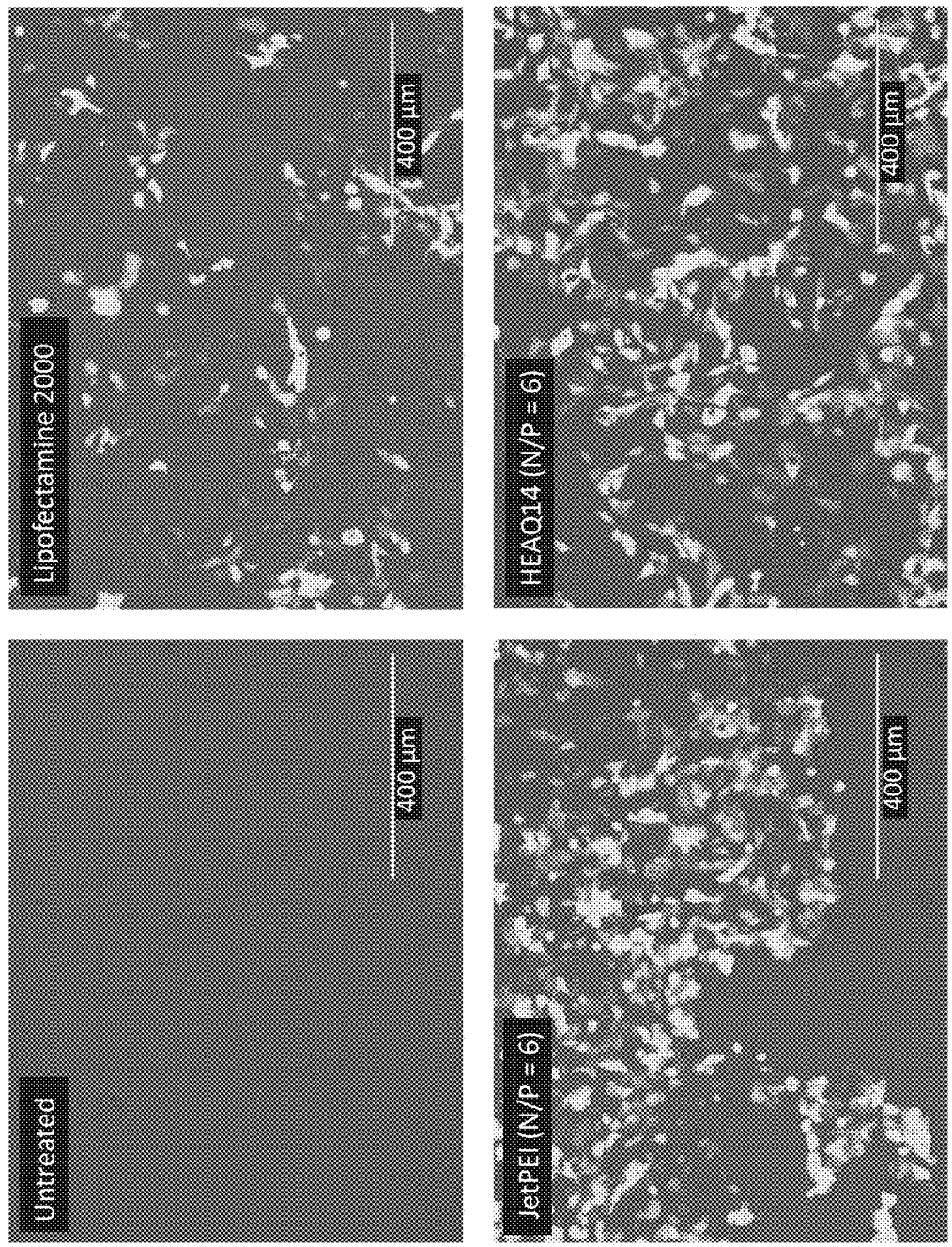
FIG. 32b shows a live-cell widefield fluorescence microscopy of HEK-293T cells, transfected with GFP (Zs-Green) plasmid in DMEM (without serum). Visualized 48 hours since start of transfection at 10× magnification with transmission view overlayed with GFP channel.

Initial screenings of the quinine copolymers was performed with a luciferase assay which is amenable to the identification of "hits" in large screens. In order to gain more detail about the percent of cells expressing the genetic cargo, a reporter plasmid (4.7 kb) encoding for a GFP-derivative (ZsGreen) with CMV promoter was delivered using the HEAQ14 polymer to human embryonic kidney cells (HEK-293T). The polyplexes were diluted (3×) in DMEM (without FBS) prior to addition to the cells. The cells were left to incubate with the polyplex/media solution for 4 hours followed by dilution with DMEM (with FBS). Cells were analyzed by flow cytometry after 48 hrs since the start of the transfection, and the percentage of cells live cells expressing GFP is shown in FIGS. 32a and 32b. The toxicity of the transfection was measured by using the colorimetric CCK-8 assay which can be used to determine the number of viable cells relative to the untreated control. For a typical transfection, one would want a maximum number of cells expressing the reporter protein with as minimal cell death as possible.

Along with the untreated and plasmid only controls, the assay included JetPEI (linear PEI) and Lipofectamine 2000 optimized for the transfection conditions. Expectedly with this cell type, JetPEI gave very high levels of transfection with 99% of cells expressing GFP. Also unsurprisingly, JetPEI was quite toxic, with the sample containing only 27% of live cells relative to the untreated. In comparison, the transfection of Lipofectamine was more modest at 48%, but the number of viable cells was far higher than JetPEI with the sample containing 93% of live cells relative to the untreated. The DMAEMA- and DMAEAm-HEA copolymers showed a very low levels of GFP+ cells (1.1 and 0.8%, respectively). In comparison to these commercial controls, the transfection efficiency of the DMAEMA homopolymer (16%) is quite low. The DMAEMA-HEA copolymer shows the effect of decreasing the density of positive charge within the polymer, and it appears to decrease the transfection efficiency even lower (1.1%). Changing the methacrylate to an acrylamide, in the case of DMAEAm-HEA copolymer, decreases the transfection efficiency even further still (0.8%). By replacing this tertiary amine monomer with quinine, however, drastically increases the transfection efficiency. FIGS. 32a and 32b show the transfection efficiencies of HEAQ14 at a range of N/P ratios. A small increase from an N/P=5 to 6 gives a dramatic increase in the percentage of GFP+ cells (48 to 92%) while further increases in the N/P ratio gave slight increases in transfection efficiency (up to 95%). In considering the balance of minimizing toxicity with maximizing transfection efficiency, however, the N/P ratio of 8 achieved a great balance in high transfection efficiency (94%) and relatively low toxicity (80% viable cells). This balance gives an overall higher number of GFP+ cells compared to the gold standards in polymer- and lipid-based transfection, JetPEI and Lipofectamine, respectively.

Efficient transfection was not limited to HEK-293T cells. Other adherent cell lines including HeLa (cervical carcinoma) and HDFn (primary dermal fibroblasts) were successfully transfected (FIGS. 45 and 46) using HEAQ14. In order to determine whether HEAQ14 could be used to transfect cell lines that are more difficult to transfect, we tried the HEAQ14 reagent with the K562 cell line, a lymphoblast derived from chronic myelogenous leukemia (CML). This cell line serves as a model for targeting clinically relevant blood targets including hematopoietic stem cells (HSCs). Typically, transfections in suspension cells require a higher cell densities and DNA doses compared to adherent cell types, and the transfection protocol was optimized accordingly. Although the percentages still remained fairly low for this cell type, HEAQ14 showed improvements over the commercial reagents (FIGS. 47a and 47b) in terms of transfection efficiency and cytotoxicity. Similarly to these other transfection reagents, the transfection efficiency vs cytotoxicity can be tuned by simple adjusting of the N/P ratio.

These studies showed that the HEAQ14 polymer was not only capable of compacting, delivering, and promoting the expression of plasmid DNA into a variety of cell types, but that it was able to outperform the gold standards in polymeric- and lipid-based delivery systems. The results could not be replicated by replacing quinine with a different tertiary amine-containing monomer such as DMAEMA or DMAEAm showing that difference in quinine's structure provides an advantage for promoting the expression of DNA cargo.

Gene Editing

The delivery of a GFP-expressing plasmid into a cell is known as a transient transfection. Over time, as the cells divide, the expression of GFP will diminish until it disappears. In order to make lasting changes to the genome of a cell that will be carried on through subsequent generations, editing systems such as CRISPR/Cas9 can be used. In order to edit a specific sequence of the genome, a Cas9 protein is needed that is complexed with a guide RNA (sgRNA) that contains the target DNA sequence. The Cas9 protein can then complex to the target DNA sequence and leave a double-stranded break (DSB) in the precise location to be edited. The cell has mechanisms to repair the DSB that can lead to the desired editing. The cleaved ends of the DNA can be rejoined in a process called nonhomologous end-joining (NHEJ) which can lead to an insertion or deletion (indel) at the repaired site. This indel will lead to a frameshift that can knock out the gene. If an exogenous piece of DNA, known as a donor, is present in the nucleus that has a similar sequence to the target gene, homology-directed repair (HDR) can take place where the exogenous piece of DNA essentially replaces the native gene. If efficient HDR is achieved, mutations that lead to genetic disorders could potentially be fixed or new genes could be introduced that provide a therapeutic benefit.

To achieve HDR, three exogenous components must be present simultaneously in the nucleus: the Cas9 protein, sgRNA, and donor plasmid. The Cas9 protein and sgRNA can be encoded by a plasmid and later expressed in the cell. To achieve editing using a three plasmid system, a transfection vector is needed to shuttle all three plasmids within a cell simultaneously. Depending on the size of the donor DNA, the large amount of genetic material needed to be transferred is often not amenable to the small cargo capacities of viral vectors. Currently, the most efficient non-viral method for transfecting cells with nucleic acid cargo for editing in vitro is through electroporation. This method, however, can be quite toxic to some sensitive cell types Our goal was to use a reporter system to exemplify HEAQ14's ability to perform efficient gene editing via CRISPR/Cas9 encoded by plasmid DNA.

Developed Certo et al., the Traffic Light Reporter (TLR) system allows for facile flow-cytometric monitoring of NHEJ and HDR events caused by Cas9-induced DSB repair. If a cell undergoes HDR with the truncated GFP donor template, the cell expresses GFP. If a cell undergoes NHEJ which leads to an indel formation, a frameshift event leads to the expression of a mCherry protein formerly out of frame (FIG. 48). It should be noted that only third of mutagenic NHEJ events cause expression of mCherry.[56] Therefore, the number of cells that have had gene knockouts are 3× the number of mCherry+ cells. HEK-293T cells were modified to contain the TLR system in their genome (see Methods for details).

The three plasmids encoding the Cas9 protein, sgRNA, and donor GFP template were mixed at equal weight ratios prior to mixing with the polymer. Optimization studies showed that to reach maximum levels of editing, higher doses of total plasmid compared to the transient transfection studies were required (FIG. 49). A range of doses and N/P ratios tested for each control. When only one N/P ratio or dose is shown, those are the optimized conditions for that reagent. It should be noted that generally, for most transfection conditions, Lipofectamine performs optimally at one half the dose compared to polymeric transfection vectors.

Figure 33:
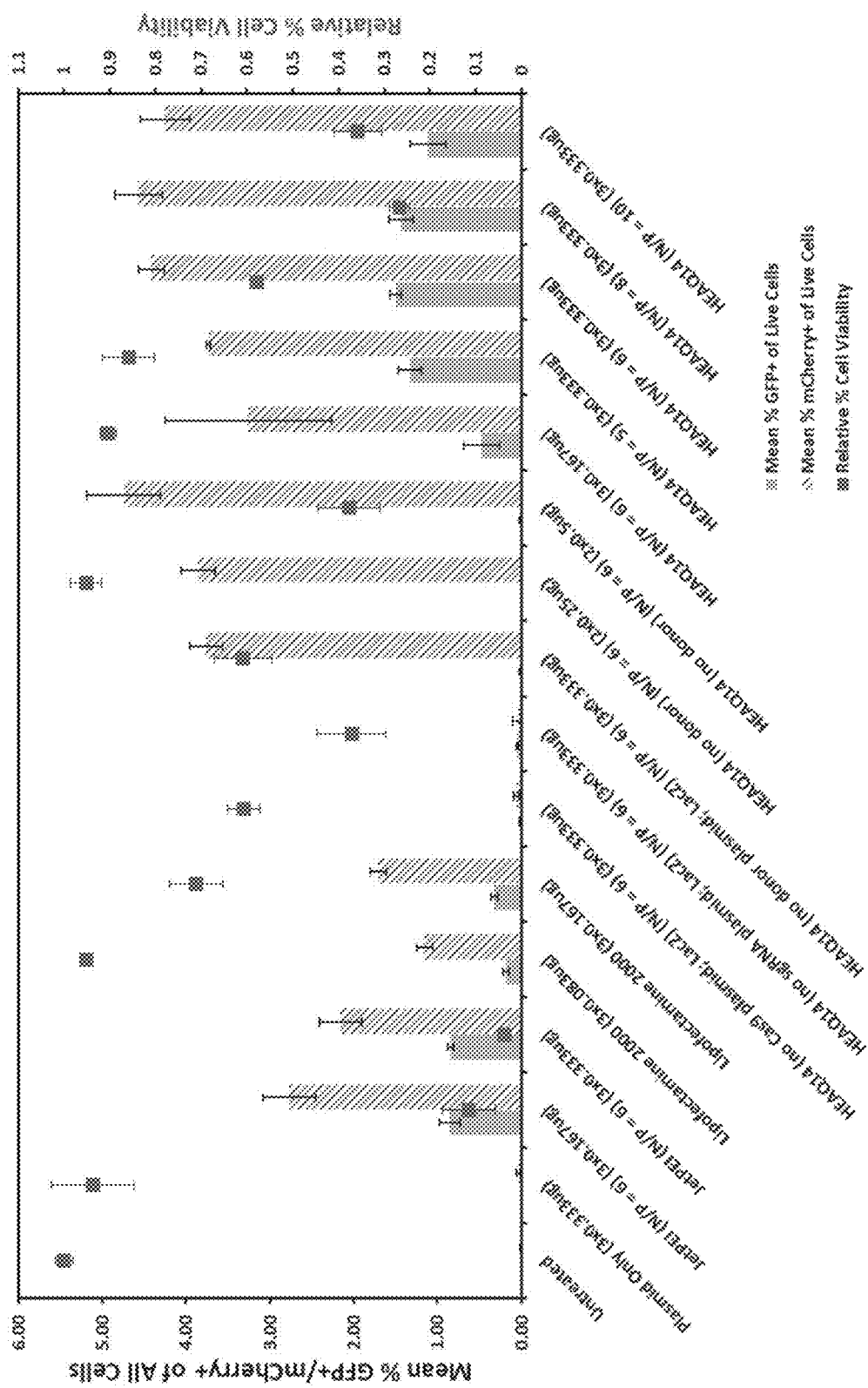
FIG. 33 shows gene editing in HEK-293T TLR cells via CRISPR/Cas9 system delivered by plasmids as quantified by flow cytometry. Bars (left y-axis) show percentage of cells expressing either GFP (green) or mCherry (red). Dots (right y-axis) correspond to relative fraction of viable cells in sample as compared to the untreated sample as determined by the CCK-8 viability assay.

The cells were analyzed by flow cytometry six days after transfection after a couple passages. This time period allowed for edited cells made non-viable from the transfection conditions to be excluded from analysis. Control samples were included that plasmid payloads where one of the three components (Cas9, sgRNA, and donor) was replaced with an equivalent amount of a LacZ plasmid (gene encoding for β-galactosidase) that served as a control that should not contribute to the editing. When either the Cas9 or sgRNA was replaced with LacZ, no editing was observed (FIG. 33). When the donor plasmid was replaced with LacZ, no GFP expression (from HDR events) were observed. These controls validated the functional role of each plasmid in the prescribed editing.

At the higher doses needed for editing, the toxicity of JetPEI was magnified. With a total dose of 1 μg, only 4% of the cells relative to the untreated remained. Also despite having the highest transfection efficiencies in the transient transfection studies, JetPEI did not give the highest editing results. The 0.5 μg sample had an average GFP+ population of 0.86% and average mCherry+ population of 2.76%. Considering that mCherry+ cells represent approximately one third of mutagenic NHEJ events, the total NHEJ editing in this sample is approximately 8.3%. Combining the total amount of HDR and NHEJ, JetPEI (at 0.5 µg of DNA) edited a total of 9.14% of cells. As mentioned, the optimal dose for Lipofectamine tends to be half that of the polymeric reagents, and at 0.5 µg, Lipofectamine yielded less editing than JetPEI (GFP=0.33%, mCherry=1.71%), but was significantly less toxic (71% of viable cells relative to untreated) yielding a higher number of overall edited cells than JetPEI. For HEAQ14, a range of N/P ratios and doses were assessed. Almost all samples gave higher percentages of editing events and lower toxicities compared to JetPEI. The best performing HEAQ14 sample (N/P=5, 1 µg) gave statistically significant higher editing numbers for both GFP and mCherry (1.33 and 3.73%, respectively) and a greater number of viable cells (86% relative to untreated) than JetPEI and Lipofectamine. This means that the HEAQ14 sample at this dose and N/P ratio yields a higher total number of edited cells than the controls. It is important to note that, increasing the N/P ratio beyond 5 did little to improve the percent of edited cells while drastically increasing the cytotoxicity of the transfection. As with every transfection reagent, optimization of the N/P ratio and dose are important to maximize results. Also, if one is only interested in knocking out a gene, the donor plasmid can be excluded. For HEAQ14, the same levels of NHEJ were achieved as the N/P=5 sample, but with only half the dose (0.5 µg). This allowed the toxicity to be quite minimal (95% cell viability relative to untreated) while achieving relatively high knockout rates (11.6%) compared to commercial controls.

Editing with RNP

Transfections with plasmids are a well-established technique to achieve high expression of a therapeutic protein within a cell. To achieve gene editing via Cas9, however, maximizing the levels of expression of Cas9 within the cell is not necessarily beneficial. Too much Cas9 could potentially lead to increased off-target cutting events. Some groups have found that delivering the Cas9 protein and sgRNA directly gives better editing results than by expression through plasmids. Also, given the fact that the HEAQ14 polyplexes showed sensitivity to the presence of protein in the transfection media, it is possible that the polymer may be able to bind Cas9 protein as well. This is supported by the fact that quinine is known to be strongly protein bound, mostly to alpha-1 acid glycoprotein, while in circulation. Although the Cas9 protein has an overall positive charge, complexation with the negatively charge sgRNA gives the ribonucleoprotein (RNP) complex an overall negative charge. This overall negative charge makes it amenable to potential complexation to cationic polymers. Also considering the fact that HEAQ14 was able to deliver multiple plasmids at once, it was thought that HEAQ14 may allow for simultaneous delivery of the RNP complex with a plasmid donor. In order to test this hypothesis, Cas9 protein with three nuclear localization sequences (NLS) tags (see Methods for details) was complexed with sgRNA at an approximate 1:3 molar ratio (1:0.25 mass ratio). Upon complexation, this RNP was mixed with the same plasmid donor used in the preceding TLR study at an approximate 1:1 molar ratio (1:1 mass ratio) to the Cas9 protein. This RNP/plasmid mixture was then mixed with HEAQ14 at a given N/P ratio (where only quinine's tertiary amines and total phosphodiester bonds were included in the calculation). The polyplex solution was introduced to HEK-293T modified with the TLR system, and editing was monitored by flow cytometry after 6 days (FIG. 50). The procedure was also done with JetPEI (N/P=5), but the number of live cells were so low for the JetPEI samples, statistically relevant data could not be acquired. For HEAQ14, however, editing levels were comparable to those obtained for plasmid editing. The RNP samples with the plasmid donor performed slightly worse than for the "all plasmid" sample, but interestingly, NHEJ levels by the RNP were recovered on when the donor plasmid was replaced with LacZ. Although limited, this initial study showed that HEAQ14 does indeed deliver RNP and can promote simultaneous delivery of RNP with a donor plasmid and achieve editing. More work is needed to characterize the complexation of the RNP with the HEAQ14 polymer and to optimize editing via this route.

Using HEK-293T cells modified with a Traffic Light Reporter system, we have shown that the HEAQ14 polymer's ability to transfect this cell line with plasmid-based cargo at high rates with low cytotoxicity could be utilized for genome editing. The HEAQ14 managed to achieve higher levels of gene repair (HDR) and gene knockout (NHEJ) and kill less cells than the gold standards in non-viral nanoparticle-based gene delivery systems, JetPEI and Lipofectamine), leading to overall more edited cells. (Possibly include sentence on showing potential for using protein-based cargo for editing).

Fluorescence

Once a new polymeric transfection vector is made and shown to be efficacious, it is often labelled with a fluorophore so that it can be tracked within the cell via fluorescence microscopy. It may be difficult to quantify the exact amount of fluorophore added and if the addition of the fluorophore affects the polymer's properties. Since quinine-copolymers are inherently fluorescent, there is no need to worry about labelling the polymer with an exogenous fluorophore. Using HEAQ14's fluorescent properties, we aim to examine the polymer's mechanism of action. Quinine's well-established fluorescent properties are due to its methoxy-substituted quinoline ring. Quinine has excitation maximums in the UV at 250 and 350 nm, and its emission max is at 450 nm (blue light). It is strongly fluorescent and is often used a quantum yield standard. Like many fluorophores, quinine's fluorescence is dependent upon the pH, and quinine shows increased fluorescence with decreasing pH. This dependence also exists for the polymer. It is also known that quinine is quenched by the presence of halide anions in solution. This property is present in the polymer as well as shown over a range of $Cl^-$ concentrations (FIG. 51). At intracellular chloride ion concentration (4 mM), the fluorescence of the polymer is reduced by nearly 60%. The fluorescence, however, is still visible at these concentrations. At extracellular concentrations (110 mM), the fluorescence is reduced by 93%. Therefore, only the polymer endocytosed by the cell is clearly visible by fluorescence. In addition, at high concentrations in solution, free quinine can exhibit self-quenching similarly to other fluorophores. This self-quenching behavior is enhanced in situations where quinines are forced together in close proximity by tethering to a polymer chain. This self-quenching by incorporation into a polymer chain is also exhibited by our quinine copolymers (FIG. 52). This self-quenching behavior also gives insight into the aggregation behavior of the quinine copolymers. In comparison to the Am and HEAm copolymers, the HEA-quinine copolymer shows a stronger tendency to aggregate upon addition to a buffer at physiological pH. This aggregation behavior is likely due to stronger pi-pi stacking between quinoline rings in the HEA-quinine copolymer. Strong interactions between the quinoline rings should also lead to more self-quenching in fluorescence spectrum. At equal molar concentrations, quinine fluorescence in HEAQ14 is only 7% that of free quinine. Quinine fluorescence in the HEAm and Am copolymers is almost 4× higher (~25%). The comonomer likely modulates how well quinine moieties interact to cause differences in self-quenching. These differences in aggregation behavior may contribute to the differences in the copolymers' ability to bind and deliver DNA and promote transfection. This is an example of having a fluorescent component in the polymer that also is responsible for its functional properties helps elucidate the mechanisms underlying those properties.

Figure 34:
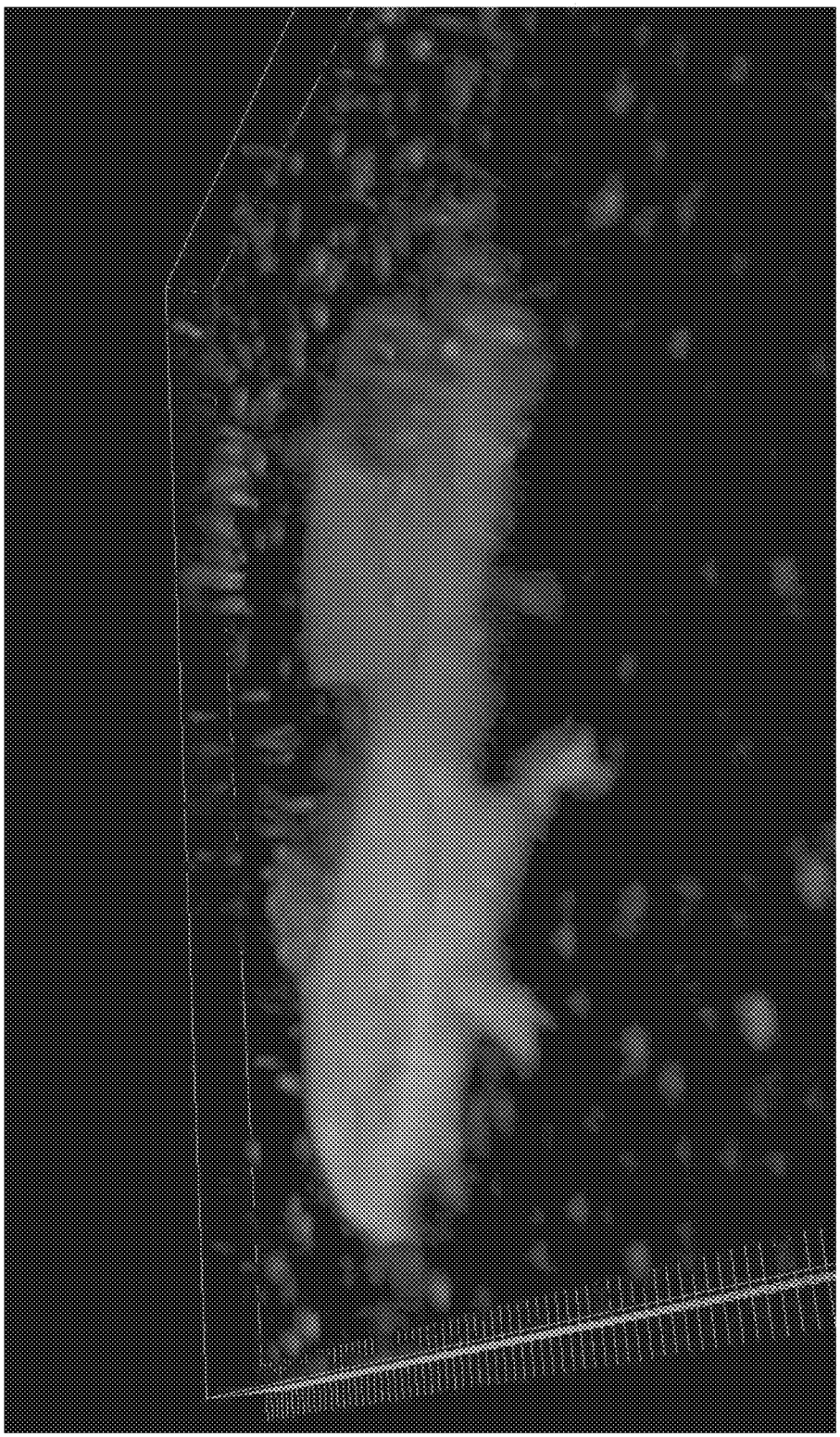
FIG. 34 shows a three-dimensional image of live HEK-293T cells expressing GFP with internalized HEAQ14 polyplexes with labelled plasmid DNA. The image was obtained at 24 hrs since start of transfection at 100× magnification with a widefield microscope and deconvolved. Dimensions: 81.92 μm×81.92 μm×3.84 μm. Red: Cy5-labelled plasmid (Ex: 650 nm, Em: 673 nm), Green: ZsGreen (GFP) (Ex: 488 nm, Em: 509 nm), Blue: HEAQ14 (Ex: 250 nm, Em: 460 nm).

Using the quinine copolymer's fluorescent properties, we were able to probe our hypothesis about HEAQ14 promoting transfection by enhancing endosomal escape. Although, we could visualize the polymer without an exogenous fluorophore, labelling of the ZsGreen plasmid with a fluorophore (Cy5) was necessary in order to visualize the plasmid as well. Wide-field microscopy with deconvolution was used to develop a three-dimensional image of an internal slice of HEK-293T cells transfected with HEAQ14 polyplexes containing Cy-5 labelled plasmid. Images were taken at time points of 4 hours and 24 hours since the start of transfection. We were interested in determining at what time point DNA made it inside and how much of the DNA inside the cell was bound by the quinine copolymer. In addition, the cells were dyed with Lysotracker Red which accumulates in acidic vesicles, such as endosomes and lysosomes. This dye was used to determine what fraction of plasmids that were colocalized with (and trapped within) acidic vesicles. We could compare the amount of plasmid trapped in the acidic endosomes when transfected with HEAQ14 compared to JetPEI, a polymer previously mentioned for being known to induce endosomal escape. FIG. 34 shows the side-view of a three-dimensional internal slice of a HEK-293T monolayer. The center of the image shows two GFP-positive cells while the background shows adjacent cells not expressing GPF since the time-point of maximum gene expression (48 hrs) has not been reached. The foreground contains no cells and show red spots where polyplexes containing DNA and show Cy5+ (red) fluorescence are adhered to the bottom of the well. These spots do not show HEAQ14 (blue) fluorescence due to quenching by the high Cl⁻ concentration in the cell media (~110 mM). The polyplexes internalized by the GFP+ cells and GFP-non expressing cells in the background show colocalized Cy5 and HEAQ14 fluorescence to give a magenta color. The HEAQ14 is easily visible within the cell due to the relatively low intracellular Cl⁻ concentration (4 mM). This image shows that the polymer and DNA have been uptaken by the cell and have a significant degree of colocalization within the cell as suggested by the Mander's Coefficient ($M_1$) of Cy5 colocalized with HEAQ14 ($M_1$=0.53+/−0.04) (FIG. 53g). The $M_1$ value decrease slightly (22%) from 4 hr to 24 hrs (SI FIG. 18b,d) possibly due to progressive unpackaging of plasmid DNA from HEAQ14. Some motion of the particles in the cell within the timescale of image acquisition, however, contributes to a slight blurring of blue and red fluorescence. Also, the pH dependence and Cl⁻ quenching of HEAQ14 makes quantification of the polymer concentration in any specific location difficult. It is clear in these images, however, that these rather large HEAQ14 polyplex aggregates are endocytosed by the cells in large quantities.

In order to compare the endosomal entrapment of plasmid in cells transfected with HEAQ14 vs cells transfected with JetPEI, the colocalization of Cy5-labelled plasmid with Lysotracker was quantified throughout the three-dimensional image. The Manders Coefficient ($M_1$) of Cy5-DNA colocalized with Lysotracker was slightly lower for JetPEI (0.58+/−0.02) than for HEAQ14 (0.69+/−0.11) (FIG. 42), although the discrepancy was not statistically significant. This suggests that JetPEI still has higher level of endosomal escape than HEAQ14 which leads to its high rate of expression. This high rate of endosomal escape is accompanied by significant toxicity. The HEAQ14 polymer seems to promote slightly less endosomal escape but is still capable of a significant amount of escape. This less intense disruption of endosomes perhaps contributes to HEAQ14's balanced transfection properties with relatively high levels of expression without being overly toxic to the cell.

TABLE 5

Comparison of solubilities between homopolymers, quinine, and quinine-copolymers in aqueous solution with 0.1M NaSO₄ and 1% acetic acid (pH~4)

| Polymer/Compound | Approx max concentration (mg/ml) |
| --- | --- |
| poly(HEA) | >100 |
| poly(Am) | >100 |
| poly(HEAm) | >100 |
| quinine | 3.6-4.0 |
| poly(HEA-co-quinine) | <0.8 |
| poly(Am-co-quinine) | 13-20 |
| poly(HEAm-co-quinine) | 20-40 |

Quinine, an anti-malarial with a broad range of properties useful in a variety of fields within chemistry and medicine, was copolymerized with several acrylate and methacrylate comonomers via an industrially friendly, one step free radical copolymerization in order to create an effective polymer-based transfection reagent. The reactivity of quinine's vinyl group with these comonomers were examined and a small library of statistical copolymers containing quinine were synthesized and characterized. These copolymers were screened for their ability to bind DNA, form polyplexes, and efficiently transfect several human cell lines in vitro. A copolymer of 2-hydroxyethyl acrylate (HEA) and quinine, poly(HEA-co-quinine), showed an exceptional ability to transfect both adherent and suspension human cell types with a GFP plasmid at levels comparable to commercial reagents, such as Lipofectamine or JetPEI, with limited cytotoxicity. Genome editing of HEK-293T cells in vitro with CRISPR/Cas9-encoding plasmids was enhanced when using poly(HEA-co-quinine) as a transfection reagent compared to commercial reagents. Also, extracellular protein in solution has a dramatic detrimental effect on the transfection efficiency of this system. It has been shown that this tendency to bind to protein, however, could potentially be useful in delivering ribonucleoproteins for CRISPR/Cas9 editing. Incorporating quinine into polymeric structures that have enhanced colloidal stability is underway so that quinine's ability to promote transfection could be used for polymeric-based transfection for in vivo. This system is being investigated for the gene editing of more clinically relevant cell types for potential use in cell-based therapies.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The disclosure is not limited to the exact details shown and described, for variations obvious to one skilled in the art will be included within the disclosure defined by the claims.

The invention claimed is:

1. A copolymer polymerized from at least:
one or more cinchona alkaloid containing compounds; and
(2-hydroxyethyl) acrylate (HEA), N-methyl aminoethylmethacrylate, ethyl methacrylate, 2-(dimethylamino) ethyl methacrylate, or combinations thereof.

2. The copolymer according to claim 1, wherein the cinchona alkaloid containing compound is selected from quinine, cinchonidine, quinidine, quiniline, derivatives thereof, or combinations thereof.

3. The copolymer according to claim 1, wherein the copolymer comprises poly(HEA-co-quinine).

4. A method of forming a copolymer-genetic component complex comprising combining the copolymer of claim 1 with at least one genetic component to form a copolymer—genetic component complex.

5. The method according to claim 4, wherein the cinchona alkaloid containing compound is selected from quinine, cinchonidine, quinidine, quiniline, derivatives thereof, or combinations thereof.

6. A method of delivering a genetic component to a cell, the method comprising combining the copolymer of claim 1 with at least one genetic component to form a copolymer—genetic component complex; and delivering the copolymer—genetic component complex to at least one cell.

7. The method according to claim 6, wherein the cinchona alkaloid containing compound is selected from quinine, cinchonidine, quinidine, quiniline, derivatives thereof, or combinations thereof.

8. The method according to claim 6, wherein the genetic component comprises DNA, RNA, proteins, or combinations thereof.

9. The method according to claim 8, wherein the DNA is selected from: plasmids, synthetic DNA, circular DNA fragments, linear DNA fragments, modified DNA and combinations thereof.

10. The method according to claim 8, wherein the RNA is selected from the group consisting of messenger RNA, doubled stranded RNA, guide RNA, methylated RNA, modified RNA, synthetic RNA, and combinations thereof.

11. The method according to claim 8, wherein the proteins are selected from the group consisting of modified proteins, synthetic proteins, and combinations thereof.

12. A copolymer polymerized from at least:
one or more cinchona alkaloid containing compounds; and
(2-hydroxyethyl)acrylamide (HEAm), N-isopropyl acrylamide (NIPAm), N,N-Dimethyl acrylamide (DMAm), or combinations thereof.

13. The copolymer according to claim 12, wherein the cinchona alkaloid containing compound is selected from quinine, cinchonidine, quinidine, quiniline, derivatives thereof, or combinations thereof.

14. The copolymer according to claim 1, wherein the copolymer comprises poly(HEAm-co-quinine).

* * * * *